United States Patent [19]
Ping et al.

[11] Patent Number: 5,585,373
[45] Date of Patent: Dec. 17, 1996

[54] 3-(7'-OXO-1'-AZA-4'-OXABICYCLO[3.2.0]-HEPT-3'-YL)PROPIONIC ACID DERIVATIVE AS ANTITUMOR AGENT

[75] Inventors: Zhang Z. Ping; Zhen J. Sheng; Zhang Q. Rong; Zhang J. Liang, all of Beijing, China; Singh Rajeshwar, Edmonton, Canada; Tomohiro Yamashita, Hidaka, Japan; Toshiyuki Toko; Hiroshi Matsumoto, both of Tokushima-ken, Japan

[73] Assignee: Taiho Pharmaceutical Co., Ltd, Tokyo-to, Japan

[21] Appl. No.: 341,177

[22] Filed: Nov. 18, 1994

[51] Int. Cl.⁶ .................. C07D 498/047; C07D 205/08; A61K 31/42

[52] U.S. Cl. .................. 514/210; 540/349; 540/360; 549/435; 549/454; 549/477; 549/476; 564/27; 564/107; 564/186

[58] Field of Search ................ 540/349; 514/210

[56] References Cited

PUBLICATIONS

King et al, Chem Abs 105, 38852 (1986).
Zhang, Chem Abs 115, 269958 (1991).

Zhang et al, Institute of Medicinal Biotechnology, Chinese Academy of Medical Sciences, Beijing, 100050, "Studies on the Total Synthesis of Clavaserine", Acta Chimica Sinica 51, 1125 (1993) and Translation.

*Primary Examiner*—Mark L. Berch
*Attorney, Agent, or Firm*—Nikaido Marmelstein Murray & Oram LLP

[57] ABSTRACT

A derivative of 3-(7'-oxo-1'-aza-4'-oxabicyclo[3.2.0]hept-3'-yl)propionic acid represented by the formula

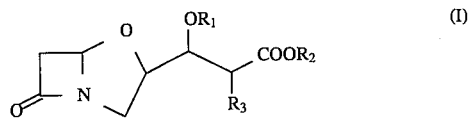

(I)

wherein $R_1$ is a hydrogen atom, a lower alkyl group optionally having one or more cycloalkyl groups, a lower acyl group, a benzoyl group optionally having one or more substituents or a benzyl group optionally having one or more substituents, $R_2$ is a hydrogen atom or a carboxyl-protecting group, $R_3$ is a hydroxyl group, an azido group, a benzenesulfonyloxy group optionally having one or more substituents, a lower alkylsulfonyloxy group optionally having one or more substituents, a tri-substituted silyloxy group or an amino group optionally having one or more substituents, provided that when $R_1$ and $R_2$ are hydrogen atoms, $R_3$ is not an amino group, and a salt thereof.

12 Claims, No Drawings

3-(7'-OXO-1'-AZA-4'-OXABICYCLO[3.2.0]-HEPT-3'-YL)PROPIONIC ACID DERIVATIVE AS ANTITUMOR AGENT

The present invention relates to a novel derivative of 3-(7'-oxo-1'-aza-4'-oxabicyclo[3.2.0]hept-3'-yl)propionic acid and a salt thereof. The compound of the present invention has excellent anticancer activity and is useful as an antitumor agent.

Since clavulanic acid, β-lactamase inhibitor, was isolated as the metabolite of Streptomyces clavuligerus and was structurally identified [Antimicrobial Agents and Chemotherapy, 11, 852 (1977)], great exploring efforts have been extended to isolate other clavam-type (7-oxo-1-aza-4-oxabicyclo[3.2.0]heptane) antibiotics. On the other hand, various researches have been conducted on the synthesis of β-lactam compounds having a clavam skeleton [DE-A-2702091, EP-A-57664, DE-A-2725690, GB-A-1585661, J. Chem. Soc. Parkin Trans. I, 2222 (1980), J. Antibiotics, 26, 217 (1983), J. Org. Chem., 50, 3457 (1985), J. Antibiotics, 29, 510 (1986), ibid., 29, 516 (1986), Chem. Pharm. Bull., 39, 2813 (1991)].

However, in most cases, attention has been directed only to the high antibacterial, antifungal and β-lactamase inhibitory activities of these compounds.

The present inventors investigated G0069A [JP-A-61-212587], G0069C [JP-A-61-268685] and Tü1718 [DE-A-3427651] produced from the Streptomyces genus, paying attention to their cytotoxicity, and found that these compounds are obtained as the metabolites of microorganisms and frequently entail difficulties in scaled-up manufacture. For example, in case of G0069A, only 20 mg thereof can be isolated from 10 L of a culture solution even if an excellent fermentation technique and an optimum isolation technology are employed. Moreover, G0069A, which is chemically unstable, involves a complicated isolation procedure and requires specific isolation techniques, e.g. for low-temperature treatment in the dark. Fermentation entails difficulty in isolation, and furthermore, the compound has five asymmetric centers including dipeptide side chains and chemical synthesis necessitates numerous steps, consequently encountering difficulties.

An object of the present invention is to provide a more easily producible, chemically stabler, lower toxicity compound having higher antitumor activity than G0069A and the like.

The present inventors conducted extensive research to overcome the foregoing problems and discovered a more easily producible, chemically stabler, less toxic compound having higher antitumor activity than G0069A.

According to the present invention, there is provided a derivative of 3-(7'-oxo-1'-aza-4'-oxabicyclo[3.2.0]hept-3'-yl)propionic acid represented by the formula

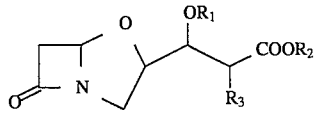

(I)

wherein $R_1$ is a hydrogen atom, a lower alkyl group optionally having one or more cycloalkyl groups, a lower acyl group, a benzoyl group optionally having one or more substituents or a benzyl group optionally having one or more substituents, $R_2$ is a hydrogen atom or a carboxyl-protecting group, $R_3$ is a hydroxy group, an azido group, a benzenesulfonyloxy group optionally having one or more substituents, a lower alkylsulfonyloxy group optionally having one or more substituents, a tri-substituted silyloxy group or an amino group optionally having one or more substituents, provided that when $R_1$ and $R_2$ are hydrogen atoms, $R_3$ is not an amino group, and a salt thereof.

The compound of the formula (I) according to the present invention has anticancer activity and is useful as an antitumor agent. The compound of this invention can be easily synthesized as compared with conventional analogous compounds and has the features of possessing chemical stability, low toxicity and high antitumor activity.

The compound of the formula (I) according to the present invention has four optically active carbon atoms, and optical isomers exist. The present invention includes all of these optical isomers. Among the optical isomers, preferred is an optically active form of [3'R,5'S] or [3'R,5'R], and more preferred is an optically active form of [3'R,5'S].

Given below are specific examples of the groups represented by $R_1$, $R_2$ and $R_3$ in the formula (I).

Examples of the lower alkyl group optionally having one or more cycloalkyl groups represented by $R_1$ are straight- or branched-chain alkyl groups of 1 to 6 carbon atoms such as methyl, ethyl, propyl, isopropyl, butyl, 1-methylpropyl, 2-methylpropyl, 1,1-dimethylethyl, pentyl, 1-methylbutyl, 2-methylbutyl, 3-methylbutyl, 2,2-dimethylpropyl, hexyl, 1-methylpentyl, 2-methylpentyl, 3-methylpentyl, 4-methylpentyl, 3,3-dimethylbutyl and the like or the above lower alkyl groups substituted by cycloalkyl groups of 3 to 6 carbon atoms such as cyclopropyl, cyclobutyl, cyclopentyl, cyclohexyl, cyclopropylmethyl, cyclobutylmethyl, cyclopentylmethyl, cyclohexylmethyl, 1-cyclopropylethyl, 2-cyclohexylethyl, 2-cyclobutylpropyl, 4-cyclopentylbutyl, 3-cyclopropyl-2,2-bis(cyclopropylmethyl)propyl and the like.

Examples of the lower acyl group represented by $R_1$ are straight- or branched-chain acyl groups of 1 to 6 carbon atoms such as formyl, acetyl, propionyl, butyryl, 2-methylpropionyl, pentanoyl, 3-methylbutyryl, 2,2-dimethylpropionyl, hexanoyl and the like.

Examples of substituents in the benzoyl group optionally having one or more substituents represented by $R_1$ are straight- or branched-chain lower alkyl groups of 1 to 6 carbon atoms optionally having 1 to 3 halogen atoms such as methyl, ethyl, propyl, isopropyl, butyl, t-butyl, pentyl, hexyl, trifluoromethyl, etc., straight- or branched-chain lower alkoxy groups of 1 to 6 carbon atoms such as methoxy, ethoxy, propoxy, isopropoxy, butoxy, t-butoxy, pentyloxy, hexyloxy, etc., halogen atoms such as fluorine, chlorine, bromine and iodine, a nitro group, a cyano group and lower alkoxycarbonyl groups substituted by the lower alkoxy groups described above.

Examples of substituents in the benzyl group optionally having one or more substituents represented by $R_1$ are straight- or branched-chain lower alkyl groups of 1 to 6 carbon atoms optionally having 1 to 3 halogen atoms such as methyl, ethyl, propyl, isopropyl, butyl, t-butyl, pentyl, hexyl, trifluoromethyl, etc., straight- or branched-chain lower alkoxy groups of 1 to 6 carbon atoms such as methoxy, ethoxy, propoxy, isopropoxy, butoxy, t-butoxy, pentyloxy, hexyloxy, etc., halogen atoms such as fluorine, chlorine, bromine and iodine, a nitro group, a cyano group, and lower alkoxycarbonyl groups substituted by the lower alkoxy groups described above.

Examples of the carboxyl-protecting group represented by $R_2$ are straight- or branched-chain lower alkyl groups of 1 to 6 carbon atoms optionally having 1 to 3 halogen atoms such as methyl, ethyl, propyl, isopropyl, butyl, t-butyl, trifluoromethyl, trichloroethyl, etc., substituted or unsubstituted aralkyl groups such as benzyl, benzhydryl, triphenylmethyl, o-methoxybenzyl, p-methoxybenzyl, p-nitrobenzyl, etc., acyloxyalkyl groups such as acetoxymethyl, acetoxyethyl, propionyloxyethyl, pivaloyloxyethyl, benzoyloxymethyl, benzoyloxyethyl, benzylcarbonyloxymethyl, cyclohexylcarbonyloxymethyl, etc., alkoxyalkyl groups such as methoxymethyl, ethoxymethyl, benzyloxymethyl, etc., a tetrahydropyranyl group, a dimethylaminoethyl group, a dimethyltrichlorosilyl group, trichlorosilyl group and the like.

Examples of substituents in the benzenesulfonyloxy group optionally having one or more substituents represented by $R_3$ are straight- or branched-chain lower alkyl groups of 1 to 6 carbon atoms optionally having 1 to 3 halogen atoms such as methyl, ethyl, propyl, isopropyl, butyl, t-butyl, pentyl, hexyl, trifluoromethyl, etc., straight- or branched-chain lower alkoxy groups of 1 to 6 carbon atoms such as methoxy, ethoxy, propoxy, isopropoxy, butoxy, t-butoxy, pentyloxy hexyloxy, etc., halogen atoms such as fluorine, chlorine, bromine and iodine, a nitro group, a cyano group and lower alkoxycarbonyl groups substituted by the lower alkoxy groups described above. Examples of benzenesulfonyloxy group optionally having one or more substituents are benzenesulfonyloxy, 4-chlorobenzenesulfonyloxy, 3-iodobenzenesulfonyloxy, 2-bromobenzenesulfonyloxy, p-toluenesulfonyloxy, 4-(trifluoromethyl)benzenesulfonyloxy, 4-methoxybenzenesulfonyloxy, 4-nitrobenzensulfonyloxy, 3-(methoxycarbonyl)benzenesulfonyloxy, 4-methoxy-2 nitrobenzenesulfonyloxy, 4-chloro-2-cyanobenzenesulfonyloxy and the like.

Examples of substituents in the lower alkylsulfonyloxy group optionally having one or more substituents represented by $R_3$ are straight- or branched-chain lower alkoxy groups of 1 to 6 carbon atoms such as methoxy, ethoxy, propoxy, butoxy, t-butoxy, pentyloxy, hexyloxy, etc., halogen atoms such as fluorine, chlorine, bromine and iodine, etc., a nitro group, a cyano group, a phenyl group and lower alkoxycarbonyl groups substituted by the lower alkoxy groups described above. Examples of the lower alkylsulfonyloxy group optionally having one or more substituents are methanesulfonyloxy, chloromethanesulfonyloxy, trifluoromethanesulfonyloxy, 2,2,2-trifluoroethanesulfonyloxy, 2-methoxyethanesulfonyloxy, 3-nitropropanesulfonyloxy, benzylsulfonyloxy and the like.

Examples of substituents in the tri-substituted silyloxy group represented by $R_3$ are straight- or branched-chain lower alkyl groups of 1 to 6 carbon atoms such as methyl, ethyl, propyl, isopropyl, butyl, 1,1-dimethylethyl, hexyl, etc., or a phenyl group. Examples of trisubstituted silyloxy groups are trimethylsilyloxy, triethylsilyloxy, 1,1-dimethylethyldimethylsilyloxy, diethylphenylsilyloxy and the like.

Substituents in the amino group optionally having one or more substituents represented by $R_3$ are not specifically limited insofar as they can be easily removed by catalytic reduction or the like. Examples of such substituents are 4-methoxybenzyl, 4-chlorobenzyl, benzyl, benzyloxycarbonyl, etc. Examples of amino groups optionally having one or more substituents are amino, N-benzyloxycarbonylamino, N,N-dibenzylamino, N,N-bis(benzyloxycarbonyl)amino, N-benzyl-N-benzyloxycarbonylamino, etc.

Salts of the compounds of the formula (I) include acid addition salts and/or base salts prepared by causing a pharmaceutically acceptable acid or base compound to act on the compound. Examples of the acid addition salt are salts of the compound with an inorganic acid such as hydrochloric acid, sulfuric acid, phosphoric acid, hydrobromic acid, etc., or with an organic acid such as oxalic acid, maleic acid, fumaric acid, malic acid, tartaric acid, citric acid, benzoic acid, acetic acid, p-toluenesulfonic acid, methanesulfonic acid, etc. Examples of the base salt are salts of the compound with an alkali metal or alkaline earth metal such as sodium, potassium, magnesium, calcium, etc. and organic salts of the compound with an amine such as ammonia, methylamine, triethylamine, piperidine, pyridine, etc.

Among the compounds of the formula (I), preferred are compounds wherein $R_1$ is a hydrogen atom, a lower alkyl group optionally having one or more cycloalkyl groups, a lower acyl group, a benzoyl group optionally having one or more substituents or a benzyl group optionally having one or more substituents, and when $R_1$ is a hydrogen atom, a lower acyl group or a benzoyl group optionally having one or more substituents, $R_2$ represents a hydrogen atom or a benzyl group and $R_3$ represents a hydroxyl group, an azido group, a benzenesulfonyloxy group optionally having one or more substituents or an amino group, or when $R_1$ is a lower alkyl group optionally having one or more cycloalkyl groups or a benzyl group optionally having one or more substituents, $R_2$ represents a hydrogen atom or a benzhydryl group and $R_3$ represents a hydroxyl group, an azido group, a lower alkylsulfonyloxy group optionally having one or more substituents, a tri-substituted silyloxy group or an amino group optionally having one or more substituents.

Preferred compounds of the present invention are those of formula (I) wherein $R_1$ is a lower acyl group, a benzoyl group, a lower alkyl group optionally having one or more cycloalkyl groups or a benzyl group optionally having one or more halogen atoms or lower alkoxy groups, $R_2$ is a hydrogen atom and $R_3$ is an amino group.

More preferred compounds are those of the formula (I) wherein $R_1$ is an acetyl group, a benzoyl group, a methyl group, a cyclopropylmethyl group, a benzyl group, a 4-fluorobenzyl group or a 4-methoxybenzyl group, $R_2$ is a hydrogen atom and $R_3$ is an amino group.

Preferred compounds are 3-[(3'R,5'S)-7'-oxo-1'-aza-4'-oxabicyclo[3.2.0]hept-3'-yl]-2(R)-amino-3(R)-acetoxypropionic acid, 3-[(3'R,5'S)-7'-oxo-1'-aza-4'-oxabicyclo[3.2.0]hept-3'-yl]-2(R)-amino-3(R)-benzoyloxypropionic acid, 3-[(3'R,5'S)-7'-oxo-1'-aza-4'-oxabicyclo[3.2.0]hept-3'-yl]-2(S)-amino-3(R)-methoxypropionic acid, 3-[(3'R,5'S)-7'-oxo-1'-aza-4'-oxabicyclo[3.2.0]hept-3'-yl]-2(S)-amino-3(R)-(cyclopropylmethyloxy)propionic acid, 3-[(3'R,5'S)-7'-oxo-1'-aza-4'-oxabicyclo[3.2.0]hept-3'-yl]-2(S)-amino-3(R)-benzyloxypropionic acid, 3-[(3'R,5'R)-7'-oxo-1'-aza-4'-oxabicyclo[3.2.0]hept-3'-yl]-2(S)-amino-3(R)-benzyloxypropionic acid, 3-[(3'R,5'S)-7'-oxo-1'-aza-4'-oxabicyclo[3.2.0]hept-3'-yl]-2(S)-amino-3(R)-(4-fluorobenzyloxy)propionic acid, 3-[(3'R,5'S)-7'-oxo-1'-aza-4'-oxabicyclo[3.2.0]hept-3'-yl]-2(S)-amino-3(R)-(4-methoxybenzyloxy)propionic acid and the like.

According to the present invention, there is also provided a process, described below, for preparing 3-(7'-oxo-1'-aza-4'-oxabicyclo[3.2.0]hept-3'-yl)propionic acid derivative represented by the formula (I).

A process for preparing a compound represented by the formula

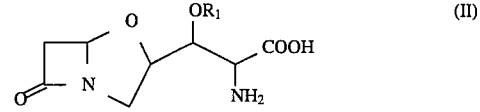

(II)

wherein $R_1$ is a lower alkyl group optionally having one or more cycloalkyl groups, a lower acyl group, a benzoyl group optionally having one or more substituents or a benzyl group optionally having one or more substituents, characterized by a catalytic hydrogenation in the presence of a catalyst of the compound represented by the formula (I), wherein $R_1$ is as defined above, $R_2$ is a hydrogen atom or a carboxyl-protecting group and $R_3$ is an azido group or an amino group optionally having one or more substituents, provided that a compound wherein $R_2$ is a hydrogen atom and $R_3$ is an amino group is excluded.

The 3-(7'-oxo-1'-aza-4'-oxabicyclo[3.2.0]hept-3'-yl)propionic acid derivative of the formula (I) according to the invention can be prepared by a process using various compounds as the starting materials, for example, by the process A described below for the compound wherein $R_1$ is a hydrogen atom, a lower acyl group or a benzoyl group optionally having one or more substituents, by the process B described below for the compound wherein $R_1$ is a lower alkyl group optionally having one or more cycloalkyl groups or a benzyl group optionally having one or more substituents, or especially, by the process C described below for the compound wherein $R_1$ is a benzyl group.

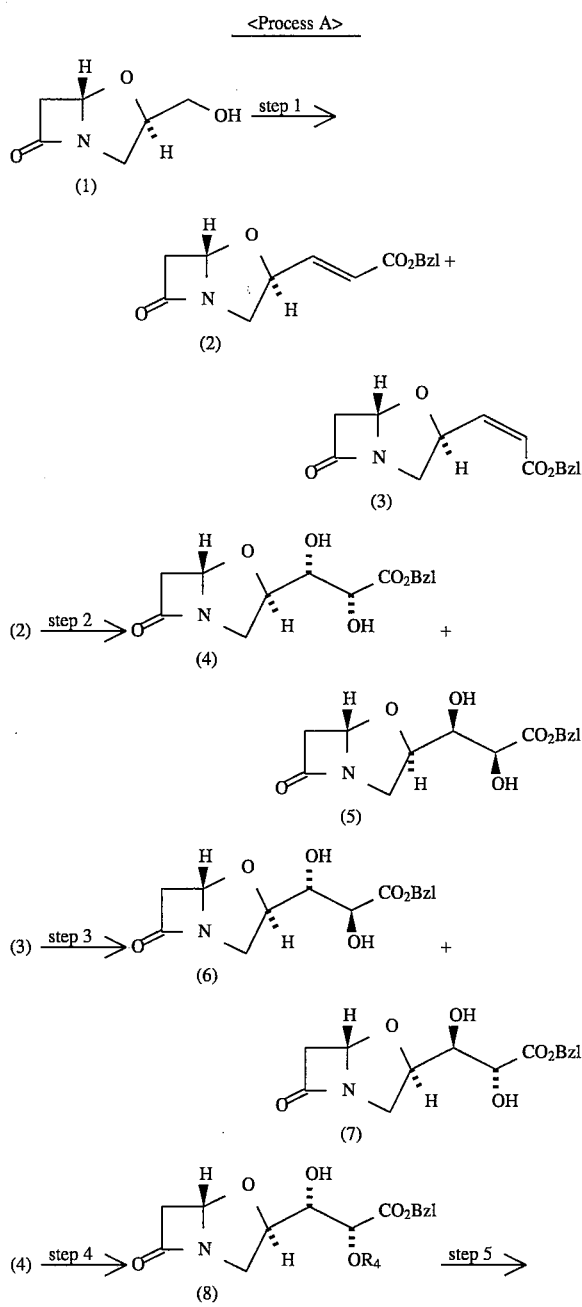

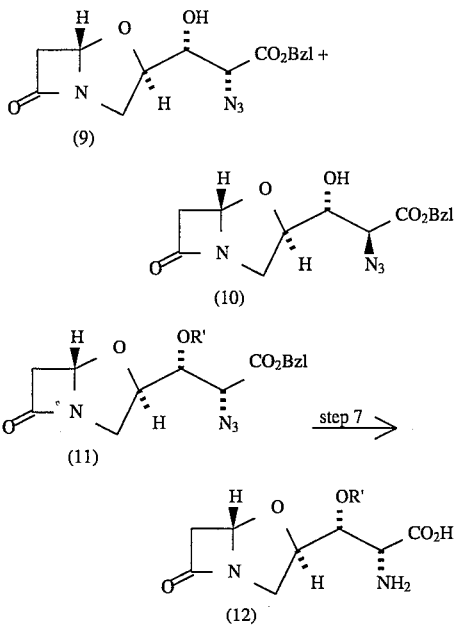

wherein R' is a lower acyl group or a benzoyl group optionally having one or more substituents, $R_4$ is a sulfonyl residue, and Bzl is a benzyl group.

Examples of the sulfonyl residue $R_4$ are lower alkanesulfonyl groups which may be substituted with a halogen atom such as methanesulfonyl, trifluoromethanesulfonyl, etc., and benzenesulfonyl groups which may be substituted such as 4-chlorobenzenesulfonyl, p-toluenesulfonyl, etc.

The steps in the Reaction Scheme illustrated above are executed as described below in detail.

<Step 1>

A known compound (1) (Chem. Pharm. Bull., 39, 2212 (1991)) is reacted with an oxidizing agent in a suitable solvent in the presence of a basic compound. The obtained reaction mixture is reacted with benzyl (triphenylphosphoranylidene)acetate without isolation, giving a compound (2) and a compound (3).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., esters such as ethyl acetate, etc. and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic amines such as triethylamine, pyridine, piperidine, diisopropylethylamine, 1,8-diazabicyclo[5.4.0]undec-7-ene, 4-dimethylaminopyridine, etc.

Examples of useful oxidizing agents are dimethylsulfoxide/reactive derivatives of acids such as dimethylsulfoxide/trifluoroacetic anhydride, dimethylsulfoxide/oxalyl chloride, etc.

As to the proportions of the compounds used in the reaction with the oxidizing agent, it is suitable to use 1 to 5 mole equivalents of dimethylsulfoxide, 1 to 3 mole equivalents of the reactive derivative of acid and 2 to 10 mole equivalents of the basic compound, per mole of the compound (1). The reaction advantageously proceeds if the reaction temperature is in the range of approximately −100° C. to room temperature, preferably −100° C. to 0° C. and the reaction time is in the range of 5 minutes to 3 hours, preferably 5 minutes to 1 hour.

In the reaction with benzyl (triphenylphosphoranylidene) acetate, it is suitable to use 1 to 3 mole equivalents of benzyl (triphenylphosphoranylidene)acetate per mole of the oxidation reaction mixture. The reaction advantageously proceeds if the reaction temperature is in the range of approximately −100° C. to room temperature, preferably −100° C. to 0° C. and the reaction time is in the range of 10 minutes to 5 hours, preferably 0.5 to 3 hours.

When required, the compounds (2) and (3) prepared by the reaction is isolated from the reaction product before use in the next step.

<Step 2 and Step 3>

The compounds (2) and (3) obtained in the step 1 are reacted with an oxidizing agent in a suitable solvent, giving compounds (4) to (7).

Solvents useful in the reaction are not critical and can be suitably selected from solvents which do not participate in the reaction. Useful solvents include, for example, alkyl ketones such as acetone, methyl ethyl ketone, etc., alcohols such as methanol, ethanol, t-butanol, etc., aprotic polar solvents such as acetonitrile, N,N-dimethylformamide, dimethylsulfoxide, hexamethylphosphoric triamide, etc., pyridine, water and so on. These solvents can be used singly or in mixture with one another.

Useful oxidizing agents include osmium tetroxide, N-methylmorpholine-N-oxide, potassium permanganate, t-butylperoxide, etc. These agents can be used alone or in combination.

As to the proportions of the compounds used in the reaction, it is suitable to use 0.002 to 5 mole equivalents of the oxidizing agent per mole of the compound (2) or (3). The reaction advantageously proceeds if the reaction temperature is in the range of approximately −100° C. to 50° C., preferably −80° C. to room temperature and the reaction time is in the range of 5 minutes to 48 hours, preferably 0.5 to 24 hours.

When required, the compounds (4) to (7) prepared by the reaction are isolated from the reaction product before use in the next step.

<Step 4>

The compound (4) prepared in the step 2 is reacted with a reactive derivative of sulfonic acid in a suitable solvent in the presence of a basic compound, giving a compound (8).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., aprotic polar solvents such as acetonitrile, N,N-dimethylformamide, dimethylsulfoxide, hexamethylphosphoric triamide, etc. and organic amines such as pyridine, triethylamine, etc. These solvents can be used singly or in mixture with one another.

Examples of useful basic compounds are organic basic compounds including tertiary amines such as triethylamine, pyridine, etc. and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc., alkali metals such as sodium, potassium, etc., and hydrides of alkali metals such as sodium hydride, etc.

Examples of useful reactive derivatives of sulfonic acids are methanesulfonyl chloride, methanesulfonic anhydride, trifluoromethanesulfonic anhydride, 4-chlorobenzenesulfonyl chloride, p-toluenesulfonyl chloride, p-toluenesulfonic anhydride, etc.

As to the proportions of the compounds used in the reaction, it is suitable to use 0.5 to 5 mole equivalents of the basic compound and 0.5 to 4 mole equivalents of the reactive derivative of sulfonic acid, per mole of the compound (4). The reaction advantageously proceeds if the reaction temperature is in the range of approximately −20° C. to the boiling point of the solvent, preferably −10° C. to 50° C. and the reaction time is in the range of 0.5 to 24 hours.

When required, the compound (8) prepared by the reaction is isolated from the reaction product before use in the next step.

<Step 5>

The compound (8) obtained in the step 4 is reacted with a reagent for azidation in a suitable solvent, giving a compound (9) and a compound (10).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., and aprotic polar solvents such as acetonitrile, N,N-dimethylformamide, dimethylsulfoxide, hexamethylphosphoric triamide, etc. These solvents can be used singly or in mixture with one another.

Examples of useful reagents for azidation are alkali metal azides such as sodium azide, lithium azide, potassium azide, etc., and silyl azide derivative such as trimethylsilyl azide, etc.

As to the proportions of the compounds used in the reaction, it is suitable to use 1 to 10 mole equivalents, preferably 1 to 5 mole equivalents, of the reagent for azidation per mole of the compound (8). The reaction advantageously proceeds if the reaction temperature is in the range of approximately 0° C. to the boiling point of the solvent, preferably room temperature to 100° C. and the reaction time is in the range of 0.5 to 24 hours, preferably 1 to 10 hours.

When required, the compounds (9) and (10) prepared by the reaction are isolated from the reaction product before use in the next step.

<Step 6>

The compound (9) obtained in the step 5 is reacted with a reactive derivative of carboxylic acid in a suitable solvent in the presence of a basic compound, giving a compound (11).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., aprotic polar solvents such as acetonitrile, N,N-dimethylformamide, dimethylsulfoxide, hexamethylphosphoric triamide, etc., and organic amines such as pyridine, triethylamine, etc. These solvents can be used singly or in mixture with one another.

Examples of useful basic compounds are organic basic compounds such as pyridine, 4-dimethylaminopyridine, triethylamine, diisopropylethylamine, piperidine, 1,8-diazabicyclo[5.4.0]undec-7-ene, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc. and hydrides of alkali metals such as sodium hydride, etc.

Examples of reactive derivatives of carboxylic acid are acetic anhydride, acetyl chloride, acetyl bromide, propionic anhydride, propionyl chloride, butyryl chloride, pivaloyl chloride, pivalic anhydride, valeroyl chloride, benzoic anhydride, benzoyl chloride, benzoyl bromide, 2-methylbenzoyl chloride, 3-chlorobenzoyl chloride, 4-methoxybenzoyl chloride, 4-cyanobenzoyl chloride, 4-(trifluoromethyl)benzoyl chloride, 3-chloro-2-nitrobenzoyl chloride and other halogenated acyls or acid anhydrides.

As to the proportions of the compounds used in the reaction, it is suitable to use 1 to 5 mole equivalents of the basic compound and 1 to 4 mole equivalents of the reactive derivative of carboxylic acid, per mole of the compound (9). The reaction advantageously proceeds if the reaction temperature is in the range of approximately −20° C. to the boiling point of the solvent, preferably 0° C. to room temperature, and the reaction time is in the range of 0.5 to 12 hours.

The compound (11) prepared by the reaction can be used in the next step after isolation, when so required.

<Step 7>

The compound (11) obtained in the step 6 is subjected to catalytic reduction in a suitable solvent in the presence of a catalyst, giving a compound (12).

Solvents useful in the reaction are not critical and can be suitably selected from solvents which do not participate in the reaction. Useful solvents include, for example, tetrahydrofuran, dioxane, methanol, ethanol, ethyl acetate, N,N-dimethylformamide, acetic acid, water, etc. These solvents can be used singly or in mixture with one another.

Useful catalysts include, for example, metals of the VIII group supported by various carriers, such as palladium-carbon, palladium-alumina, palladium-asbestos, palladium-barium carbonate, palladium-barium sulfate, palladium black, palladium-calcium carbonate, platinum-carbon, platinum black, platinum-calcium carbonate, etc. and oxides of the VIII group metals such as palladium oxide, platinum oxide, etc.

As to the proportions of the compounds used in the reaction, it is suitable to use 0.1 to 10 mole equivalents of the catalyst per mole of the compound (11). The reaction advantageously proceeds if the hydrogen pressure is in the range of atmospheric pressure to 100 atm., preferably atmospheric pressure to 10 atm., the reaction temperature is in the range of approximately 0° to 100° C., preferably room temperature to 50° C., and the reaction time is in the range of 10 minutes to 48 hours, preferably 0.5 to 24 hours.

The process A gives compounds with the confirmed configurations in the 3'- and 5'-positions, namely forms of [3'R,5'S]. Asymmetric carbons are in the 2- and 3-positions and thus 4 types of optically active compounds can exist. All of 4 types of optically active compounds can be produced by reacting the compounds (5), (6) and (7) in the same manner in the step 4 and subsequent steps.

Twelve types of optically active compounds can be produced using as the starting material (1) [3'S, 5'R] form, [3'R, 5'R] form or [3'S, 5'S] form in place of [3'R, 5'S] form, and all of 16 types of optically active compounds can be prepared.

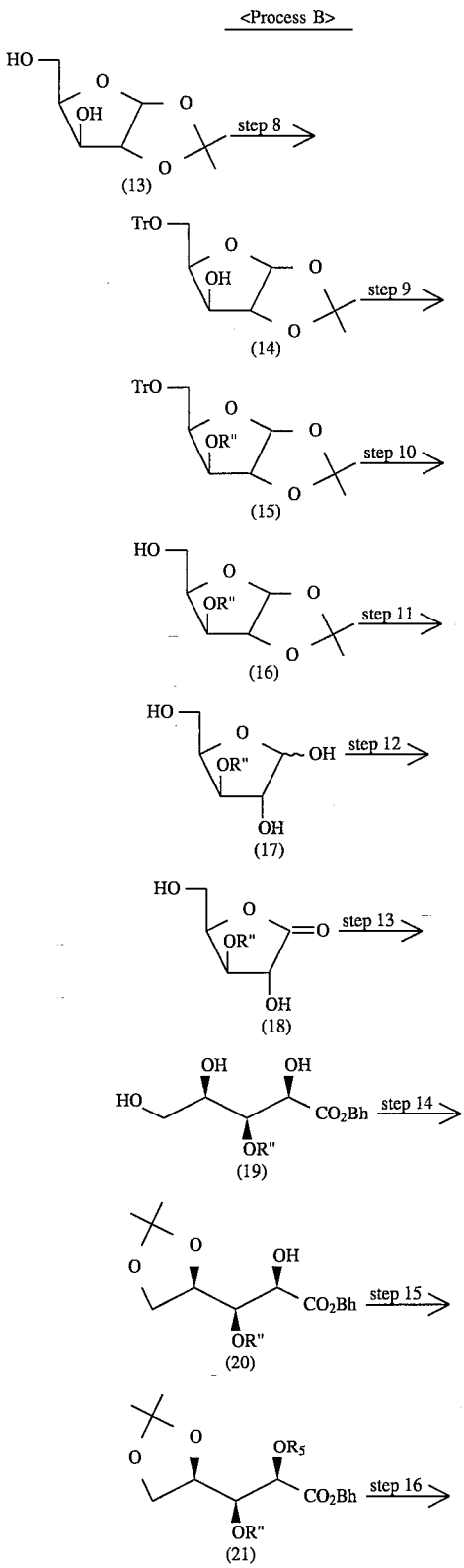

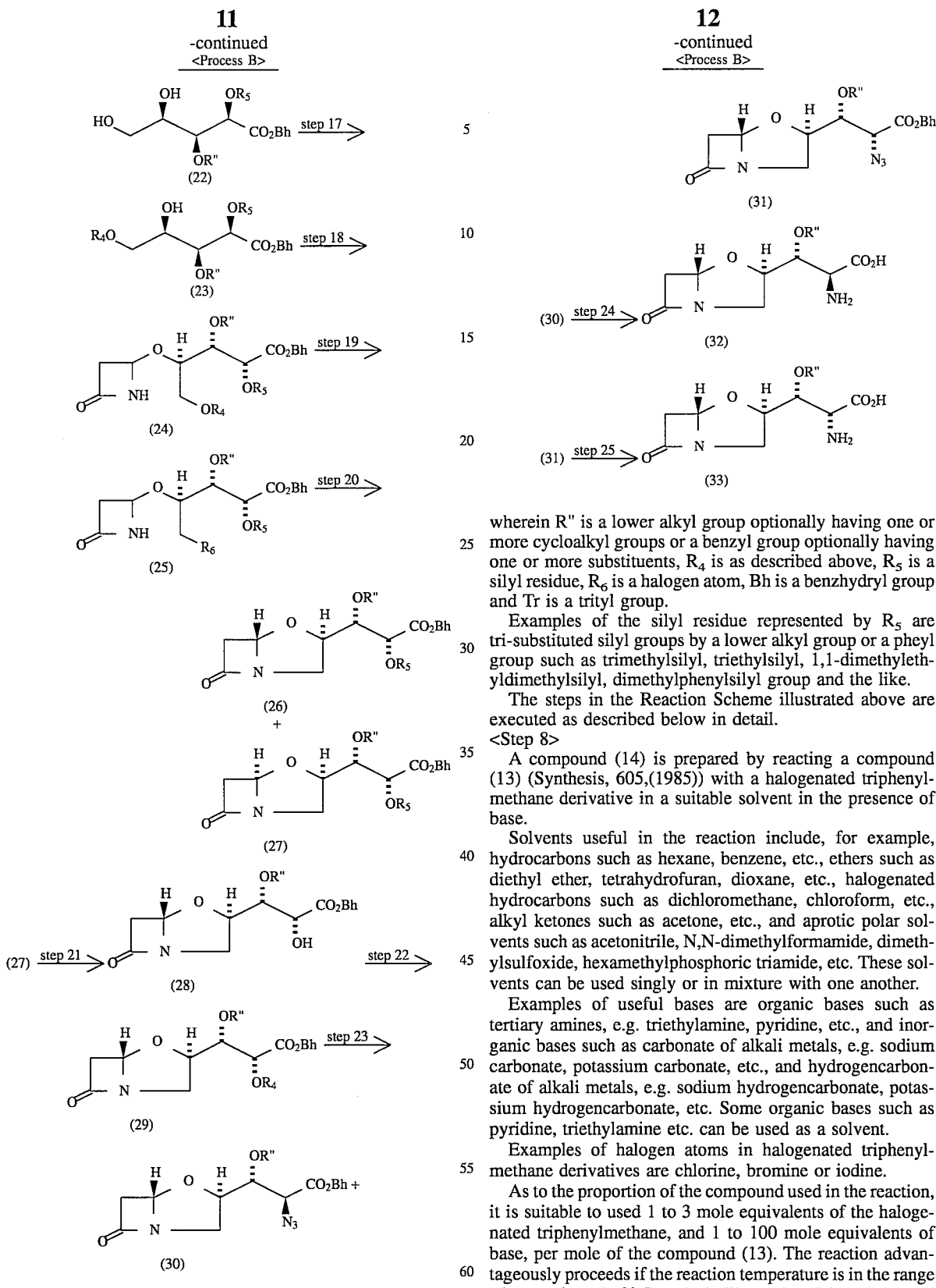

wherein R" is a lower alkyl group optionally having one or more cycloalkyl groups or a benzyl group optionally having one or more substituents, $R_4$ is as described above, $R_5$ is a silyl residue, $R_6$ is a halogen atom, Bh is a benzhydryl group and Tr is a trityl group.

Examples of the silyl residue represented by $R_5$ are tri-substituted silyl groups by a lower alkyl group or a pheyl group such as trimethylsilyl, triethylsilyl, 1,1-dimethylethyldimethylsilyl, dimethylphenylsilyl group and the like.

The steps in the Reaction Scheme illustrated above are executed as described below in detail.

<Step 8>

A compound (14) is prepared by reacting a compound (13) (Synthesis, 605,(1985)) with a halogenated triphenylmethane derivative in a suitable solvent in the presence of base.

Solvents useful in the reaction include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., and aprotic polar solvents such as acetonitrile, N,N-dimethylformamide, dimethylsulfoxide, hexamethylphosphoric triamide, etc. These solvents can be used singly or in mixture with one another.

Examples of useful bases are organic bases such as tertiary amines, e.g. triethylamine, pyridine, etc., and inorganic bases such as carbonate of alkali metals, e.g. sodium carbonate, potassium carbonate, etc., and hydrogencarbonate of alkali metals, e.g. sodium hydrogencarbonate, potassium hydrogencarbonate, etc. Some organic bases such as pyridine, triethylamine etc. can be used as a solvent.

Examples of halogen atoms in halogenated triphenylmethane derivatives are chlorine, bromine or iodine.

As to the proportion of the compound used in the reaction, it is suitable to used 1 to 3 mole equivalents of the halogenated triphenylmethane, and 1 to 100 mole equivalents of base, per mole of the compound (13). The reaction advantageously proceeds if the reaction temperature is in the range of approximately 0° C. to the boiling point of the solvent and the reaction time is in the range of 0.5 to 24 hours, preferably 0.5 to 5 hours.

The compound (14) prepared by the reaction can be used in the next step after isolation, when so required.

<Step 9>

The compound (14) obtained in the step 8 is reacted with a base in a suitable solvent under inert gas atmosphere and the obtained reaction mixture is reacted with appropriate organic halides without isolation, giving a compound (15).

Solvents useful in the reaction include, for example, hydrocarbons such as hexane, benzene. etc., ethers such as diethyl ether, tetrahydrofuran, dioxane, etc., halogenated hydrocarbons such as dichloromethane, chloroform, etc., and aprotic polar solvents such as acetonitrile, N,N-dimethylformamide, dimethylsulfoxide, hexamethylphosphoric triamide, etc. These solvents can be used singly or in mixture with one another.

Useful bases include, for example, hydroxides of alkali metals such as sodium hydroxide, potassium hydroxide, etc., alkali hydrides such as sodium hydride, potassium hydride etc., or organometallic compounds such as methyl lithium, butyl lithium, lithium diisopropylamide, lithium hexamethyldisilazanate, methyl magnesium bromide, ethyl magnesium bromide etc.

The organic halide is represented by R"X wherein R" is as defined above and X is a halogen atom. The groups R" include, for example, straight- or branched-chain alkyl groups optionally substituted by cycloalkyl groups such as methyl, ethyl, propyl, isopropyl, butyl, 2,2-dimethylpropyl, hexyl, cyclopropylmethyl, cyclopentylmethyl, cyclohexylmethyl, 1-cyclopropylethyl, 3-cyclopropyl-2,2-bis(cyclopropylmethyl)propyl, etc., optionally substituted benzyl groups such as benzyl, 4-fluorobenzyl, 4-methoxybenzyl, 2-cyanobenzyl, 3,4-dimethoxybenzyl, 2,4-di-chlorobenzyl, 3-methylbenzyl, 2-(methyoxycarbonyl)benzyl, etc., and the halogen atoms include chlorine, bromine, iodine, etc.

In the reaction of compound (14) with base, 0.5 to 2 mole equivalents of the base is used per mole of the compound (14). The reaction advantageously proceeds if the reaction temperature is in the range of approximately −78° C. to boiling point of the solvent, preferably 0° C. to 50° C. and the reaction time is in the range of 0.5 to 72 hours, preferably 0.5 to 24 hours.

In the reaction of the reaction mixture with organic halide, 1 to 2 mole equivalents of the organic halide is used per mole of the reaction mixture. The reaction advantageously proceeds if the reaction temperature is in the range of 0° to 50° C., preferably 0° C. to room temperature and the reaction time is in the range of 0.5 to 24 hours.

The compound (15) prepared by the reaction can be used in the next step after isolation, when so required.

<Step 10>

The compound (15) prepared in step 9 is reacted with an acid, giving a compound (16).

Solvents useful in the reaction include, for example, ethers such as tetrahydrofuran, dioxane, etc., alcohols such as methanol, ethanol etc., aprotic polar solvents such as acetonitrile etc., and water. These solvents can be used singly or in mixture with one another.

Acids useful in the reaction are organic acids such as p-toluenesulfonic acid, methanesulfonic acid, acetic acid, trifluoroacetic acid etc., and inorganic acids such as hydrochloric acid, sulfuric acid, nitric acid etc.

In the reaction of compound (15) with an acid, 0.001 to 1 mole equivalent, preferably 0.005 to 0.1 mole equivalent of the acid is used per mole of the compound (15). The reaction advantageously proceeds if the reaction temperature is in the range of −78° C. to the boiling point of the solvent, preferably 0° C. to room temperature and the reaction time is in the range of 0.1 to 20 hours, preferably 0.5 to 10 hours.

The compound (16) prepared by the reaction can be used in the next step after isolation, when so required.

<Step 11>

The compound (16) prepared in step 10 is reacted with an acid, giving a compound (17).

Solvents useful in the reaction include, for example, ethers such as tetrahydrofuran, dioxane, etc., alcohols such as methanol, ethanol etc., aprotic polar solvents such as acetonitrile etc., and water. These solvents can be used singly or in mixture with one another.

Acids useful in the reaction are organic acids such as p-toluenesulfonic acid, methanesulfonic acid, acetic acid, trifluoroacetic acid etc., and inorganic acids such as hydrochloric acid, sulfuric acid, nitric acid etc.

In the reaction of compound (16) with an acid, 1 to 100 mole equivalents, preferably 1 to 10 mole equivalents of the acid is used per mole of the compound (16). The reaction advantageously proceeds if the reaction temperature is in the range of −78° C. to the boiling point of the solvent, preferably 0° to 100° C. and the reaction time is in the range of 0.1 to 20 hours, preferably 0.5 to 10 hours.

The compound (17) prepared by the reaction can be used in the next step after isolation, when so required.

<Step 12>

The compound (17) obtained in the step 11 is reacted with halogen in a suitable solvent or without a solvent in the presence of a basic compound.

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds such as tertiary amines, e.g. triethylamine, pyridine, etc., and inorganic basic compounds such as carbonates of alkali metals, e.g. sodium carbonate, potassium carbonate, etc., and hydrogencarbonate of alkali metals, e.g. sodium hydrogencarbonate, potassium hydrogencarbonate, etc.

Examples of useful halogens are chlorine, bromine, iodine, etc. among which bromine is preferred.

As to the proportions of the compounds used in the reaction, it is suitable to use 1 to 3 mole equivalents of the halogen and 1 to 10 mole equivalents, preferably 1 to 5 mole equivalents, of the basic compound, per mole of the compound (17). The reaction advantageously proceeds if the reaction temperature is in the range of approximately 0° C. to the boiling point of the solvent, preferably 0 to 50° C. and the reaction time is in the range of 1 to 72 hours, preferably 1 to 40 hours.

The compounds (18) prepared by the reaction can be used in the next step after isolation, when so required.

<Step 13>

The compound (18) obtained in the step 12 is reacted with an alkali in a suitable solvent, and the obtained reaction mixture is reacted with diphenyldiazomethane after neutralization without isolation, giving a compound (19).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Useful alkalis include, for example, hydroxides of alkali metals such as sodium hydroxide, potassium hydroxide, etc., and are used preferably as dissolved in water or an alcohol such as methanol.

Examples of the reagent useful for the neutralization reaction are inorganic mineral acids such as hydrochloric acid, sulfuric acid, etc., acidic cation exchange resins such as Dowex 50W, Dowex CCR-2 (trademarks, products of The Dow Chemical, Co., Ltd.), etc.

In the reaction of the compound (18) with the alkali, 0.1 to 2 mole equivalents of the alkali is used per mole of the compound (18). The reaction advantageously proceeds if the reaction temperature is in the range of approximately 0° C. to the boiling point of the solvent, preferably room temperature to 80° C. and the reaction time is in the range of 0.1 to 10 hours, preferably 0.5 to 5 hours. In the reaction of the reaction mixture with the diphenyldiazomethane, 1 to 2 mole equivalents of the diphenyldiazomethane is used per mole of the reaction mixture. The reaction advantageously proceeds if the temperature is in the range of approximately 0° C. to 50° C., preferably 0° C. to room temperature and the reaction time is in the range of 0.5 to 48 hours, preferably 1 to 40 hours.

The compound (19) prepared by the reaction can be used in the next step after isolation, when so required.

<Step 14>

The compound (19) prepared in the step 13 is reacted with acetone or 2,2-dimethoxypropane in a suitable solvent in the presence of a catalyst, giving a compound (20).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc. among which acetone is preferred. A preferred solvent is one of subjected to drying treatment.

Useful catalysts are halogenated hydrogens such as hydrogen chloride, organic sulfonic acids such as p-toluenesulfonic acid, methanesulfonic acid, etc., organic carboxylic acids such as acetic acid, oxalic acid, etc., Lewis acids such as ferric chloride, aluminum chloride, zinc chloride, etc., alkali earth metal salts such as cupric sulfate, cupric chloride, etc.

As to the proportions of the compounds used in the reaction, it is suitable to use 1 to 20 mole equivalents of acetone or 2,2-dimethoxypropane and 0.01 to 10 mole equivalents of the catalyst, per mole of the compound (19). The reaction advantageously proceeds if the reaction temperature is in the range of approximately 0° C. to the boiling point of the solvent, preferably 0° to 50° C. and the reaction time is in the range of 0.5 to 72 hours, preferably 1 to 48 hours.

The compound (20) prepared by the reaction can be used in the next step after isolation, when so required, <Step 15>

The compound (20) obtained in the step 14 is reacted with a suitable silylating reagent in a suitable solvent in the presence of a basic compound, giving a compound (21).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds including tertiary amines such as triethylamine, pyridine, etc., and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., alkali metals such as sodium, potassium, etc., and hydrides of alkali metals such as sodium hydride, etc.

Useful silylating reagents are, for example, trimethylsilyl chloride, trietylsilyl chloride, isopropyldimethylsilyl chloride, t-butyldimethylsilyl chloride, triisopropylsilyl chloride, dimethylphenylsilyl chloride, t-butyldimethylsilyl trifuoromethanesulfonate, etc.

As to the proportions of the compounds used in the reaction, it is suitable to use 1 to 4 mole equivalents of the silylating reagent and 1 to 4 mole equivalents of the basic compound, per mole of the compound (20). The reaction advantageously proceeds if the reaction temperature is in the range of approximately $-20°$ C. to the boiling point of the solvent, preferably $-10$ to 100° C. and the reaction time is in the range of 1 to 200 hours, preferably 5 to 130 hours.

The compound (21) prepared by the reaction can be used in the next step after isolation, when so required.

<Step 16>

The compound (21) obtained in the step 15 is reacted with an acidic compound in a in a suitable solvent, giving a compound (22).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful acidic compounds are inorganic acids such as hydrogen halides, e.g. hydrogen chloride, hydrogen bromide, etc., hydrochloric acid, sulfuric acid etc., organic acids such as carboxylic acids, e.g. acetic acid, oxalic acid, etc., sulfonic acids such as p-toluenesulfonic acid, benzenesulfonic acid, methanesulfonic acid, etc., Lewis acids such as zinc chloride, ferric chloride, boron chloride, etc. and acidic cation exchange resins such as Dowex 50W, etc.

As to the proportions of the compounds used in the reaction, it is suitable to use 0.1 to 20 mole equivalents, preferably 1 to 5 mole equivalents, of the acidic compound, per mole of the compound (21). The reaction advantageously proceeds if the reaction temperature is in the range of approximately 0° C. to the boiling point of the solvent, preferably room temperature to 100° C. and the reaction time is in the range of 0.5 to 24 hours, preferably 1 to 12 hours.

The compound (22) prepared by the reaction can be used in the next step isolation, when so required.
<Step 17>

The compound (22) obtained in the step 16 is reacted with a reactive derivative of sulfonic acid in a suitable solvent in the presence of a basic compound, giving a compound (23).

Solvents useful in the reaction are not critical and can be suitably selected from solvents Which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds including tertiary amines such as triethylamine, pyridine, etc. and secondary amines e.g. piperidine, etc., and inorganic basic compounds including hydroxides of alkali metals, e.g. sodium hydroxide, potassium hydroxide, etc., carbonates of alkali metals, e.g. sodium carbonate, potassium carbonate, etc., hydrogencarbonates of alkali metals, e.g. sodium hydrogencarbonate, potassium hydrogencarbonate, etc., alkali metals, e.g. sodium, potassium, etc., and hydrides of alkali metals such as sodium hydride, etc.

Useful reactive derivatives of sulfonic acids are, for example, methanesulfonyl chloride, methanesulfonic anhydride, trifluoromethanesulfonic anhydride, 4-chlorobenzenesulfonyl chloride, p-toluenesulfonyl chloride, p-toluenesulfonic anhydride, etc.

As to the proportions of the compounds used in the reaction, it is suitable to use 1 to 4 mole equivalents of the reactive derivative of sulfonic acid and 1 to 20 mole equivalents of the basic compound, per mole of the compound (22). The reaction advantageously proceeds if the reaction temperature is in the range of approximately −20° C. to the boiling point of the solvent, preferably −10° C. to room temperature and the reaction time is in the range of 0.5 to 24 hours.

The compound (23) prepared by the reaction can be used in the next step after isolation, when so required.
<Step 18>

The compound (23) obtained in the step 17 is reacted with 4-acetoxyazetidin-2-one in a suitable solvent in the presence of a basic compounds and a catalyst, giving a compound (24).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds such as tertiary amines e.g. triethylamine, pyridine, etc., and secondary amines e.g. piperidine, etc., and inorganic basic compounds including hydroxides of alkali metals, e.g. sodium hydroxide, potassium hydroxide, etc., carbonates of alkali metals, e.g. sodium carbonate, potassium carbonate, etc., hydrogencarbonates of alkali metals, e.g. sodium hydrogencarbonate, potassium hydrogencarbonate, etc., alkali metals, e.g. sodium, potassium etc., and hydrides of alkali metals, e.g. sodium hydride, etc.

Useful catalysts are, for example, zinc acetate, palladium acetate, etc.

As to the proportions of the compounds used in the reaction, it is suitable to use 1 to 10 mole equivalents, preferably 1 to 5 mole equivalents, of the basic compound, 0.01 to 5 mole equivalents, preferably 0.1 to 2 mole equivalents, of the catalyst and 1 to 5 mole equivalents, preferably 1 to 3 mole equivalents, of 4-acetoxyazetidin-2-one, per mole of the compound (23). The reaction advantageously proceeds if the reaction temperature is in the range of approximately 0° C. to the boiling point of the solvent, preferably 0° to 50° C. and the reaction time is in the range of 1 to 48 hours.

The compound (24) prepared by the reaction can be used in the next step after isolation, when so required.
<Step 19>

The compound (24) obtained in the step 18 is reacted with a halogenated alkali metal in a suitable solvent, giving a compound (25).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful halogenated alkali metals are lithium bromide, sodium bromide, potassium bromide, sodium iodide, potassium iodide, etc.

As to the proportions of the compounds used in the reaction, it is suitable to use 1 to 20 mole equivalents, preferably 1 to 10 mole equivalents, of the halogenated alkali metal, per mole of the compound (24). The reaction advantageously proceeds if the reaction temperature is in the range of approximately room temperature to the boiling point of the solvent and the reaction time is in the range of 1 to 24 hours, preferably 1 to 15 hours.

The compound (25) prepared by the reaction can be used in the next step after isolation, when so required.
<Step 20>

The compound (25) obtained in step 19 is reacted with a basic compound in a suitable solvent, giving compounds (26) and (27).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds such as triethylamine, pyridine, piperidine, 1,8-diazabicyclo[5.4.0]undec-7-ene, etc. and inorganic basic compounds including hydroxides of alkali metals such as sodium hydroxide, potassium hydroxide, etc., carbonates of alkali metals such as sodium carbonate, potassium carbonate, cesium carbonate, etc., hydrogencarbonates of alkali metals such as sodium hydrogencarbonate, potassium hydrogencarbonate, cesium hydrogencarbonate, etc., alkali metals such as sodium, potassium, etc., and hydrides of alkali metals such as sodium hydride, etc. silver 2,2-dimethyl-6,6,7,7,8,8,8-heptafluoro-3,5-octanedionate, etc., and alcolates of alkali metals such as sodium methoxide, potassium t-butoxide, etc.

As to the proportions of the compounds used in the reaction, it is suitable to use 1 to 10 mole equivalents, preferably 1 to 5 mole equivalents, of the basic compound, per mole of the compound (25). The reaction advantageously proceeds if the reaction temperature is in the range of approximately 0° C. to the boiling point of the solvent, preferably room temperature to 100° C. and the reaction time is in the range of 0.5 to 50 hours, preferably 1 to 30 hours.

The compounds (26) and (27) prepared by the reaction can be used in the next step after isolation, when so required.
<Step 21>

The compound (26) obtained in step 20 is reacted with a deprotective reagent for the substituted silyl protective group in a suitable solvent, giving compound (28).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol etc., and aprotic polar solvents such as acetonitrile, N,N-dimethylformamide, dimethylsulfoxide, hexamethylphosphoric triamide, etc. These solvents can be used singly or in mixture with one another.

Examples of deprotective reagents for the substituted silyl protective group are inorganic acids such as hydrogen halides, e.g. hydrogen chloride, hydrogen bromide, hydrogen fluoride, etc., hydrochloric acid and sulfuric acid, etc., organic acids such as carboxylic acids, e.g. acetic acid, oxalic acid, etc., sulfonic acids, e.g. such as p-toluenesulfonic acid, benzenesulfonic acid, methanesulfonic acid, etc., Lewis acids, e.g. zinc chloride, ferric chloride, boron chloride, etc., and acidic cation exchange resins, e.g. Dowex 50W, etc., and organic fluorinated compound, e.g. tetrabutylammmoniun fluoride, etc.

As to the proportions of the compounds used in the reaction, it is suitable to use 0.1 to 10 mole equivalents, preferably 1 to 5 mole equivalents, of the deprotective reagent, per mole of compound (26). The reaction advantageously proceeds if the reaction temperature is in the range of approximately 0° C. to the boiling point of the solvent, preferably, room temperature to 100° C. and the reaction time is in the range of 0.5 to 24 hours, preferably 1 to 10 hours.

The compound (28) prepared by the reaction can be used in the next step after isolation, when so required.
<Step 22>

The compound (28) obtained in the step 21 is reacted with a reactive derivative of sulfonic acid in a suitable solvent in presence of a basic compound, giving a compound (29).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds including tertiary amines such as triethylamine, pyridine, etc., and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc., alkali metals such as sodium, potassium, etc., and hydrides of alkali metals such as sodium hydride, etc.

Useful reactive derivatives of sulfonic acids are, for example, methanesulfonyl chloride, methanesulfonic anhydride, trifluoromethanesulfonic anhydride, 4-chlorobenzenesulfonyl chloride, p-toluenesulfonyl chloride, p-toluenesulfonic anhydride, etc.

As to the proportions of the compounds used in the reaction, it is suitable to use 1 to 4 mole equivalents of the reactive derivative of sulfonic acid and 1 to 20 mole equivalents of the basic compound, per mole of the compound (28). The reaction advantageously proceeds if the reaction temperature is in the range of approximately 0° C. to the boiling point of the solvent, preferably 0° C. to room temperature and the reaction time is in the range of 0.5 to 8 hours, preferably 1 to 5 hours.

The compound (29) prepared by the reaction can be used in the next step after isolation, when so required.
<Step 23>

The compound (29) obtained in the step 22 is reacted with the reagent for azidation in a suitable solvent, giving compounds (30) and (31).

Solvents useful in the reaction are not critical and can be suitably selected from solvents which do not participate in the reaction. Useful solvents include, for example, hydrocarbons such as hexan, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol etc., and aprotic polar solvents such as acetonitrile, N,N-dimethylformamide, dimethylsulfoxide, hexamethylphosphoric triamide, etc. These solvents can be used singly or in mixture with one another.

Examples of useful reagents for azidation are alkali metal azides such as lithium azide, sodium azide, potassium azide, etc., and silyl azide derivatives such as trimethylsilyl azide, etc.

As to the proportions of the compounds used in the reaction, it is suitable to use 1 to 10 mole equivalents, preferably 1 to 5 mole equivalents, of the reagent for azidation, per mole of the compound (29). The reaction advantageously proceeds if the reaction temperature is in the range of approximately 0° C. to the boiling point of the solvent, preferably room temperature to 100° C. and the reaction time is in the range of 0.5 to 24 hours, preferably 1 to 10 hours.

The compounds (30) and (31) prepared by the reaction can be used in the next step after isolation, when so required.
<Step 24 and 25>

The compounds (30) and (31) prepared in the step 23 are subjected to catalytic reduction in a suitable solvent in the presence of a catalyst, giving a compounds (32) and (33), respectively.

Useful solvents are not specifically limited insofar as they do not participate in the reaction. Examples of such solvents are tetrahydrofuran, dioxane, methanol, ethanol, ethyl acetate, N,N-dimethylformamide, acetic acid, water, etc. These solvents can be used singly or in mixture with one another.

Useful catalysts include, for example, metals of the VIII group supported by various carriers, such as palladium-carbon, palladium-alumina, palladium asbestos, palladium-barium carbonate, palladium black, palladium-calcium carbonate, palladium-barium sulfate, platinum-carbon, platinum black, platinum-calcium carbonate, etc., and oxides of the VIII group metals such as palladium oxide, platinum oxide, etc.

As to the proportions of the compounds used in the reaction, it is suitable to use 0.1 to 10 mole equivalents of the catalyst, per mole of the compound (30) or (31). The reaction advantageously proceeds if the conditions are as follows: the hydrogen pressure is in the range of atmospheric pressure to 100 atm., preferably atmospheric pressure to 10 atm., the reaction temperature is in the range of approximately 0° C. to 100° C., preferably room temperature to 50° C., and the reaction time is in the range of 10 minutes to 48 hours, preferably 0.5 to 24 hours.

The foregoing reaction scheme shows the steps for preparing two types of optical active compounds. Further two types of optically active compounds can be produced by repeating the reactions in the step 21 and the subsequent steps using the compound (27) and the resulting compounds. When the reactions in the step 8 and the successive steps are made using as the starting material 1,2-O-isopropylidene-D-ribofuranose, 1,2-O-isopropylidene-L-ribofuranose, 1,2-O-isopropylidene-L-xylofuranose in place of 1,2-O-isopropylidene-D-xylofuranose (13), 12 types of optically active compounds can be prepared. Namely all of 16 types of optically active compounds can be prepared.

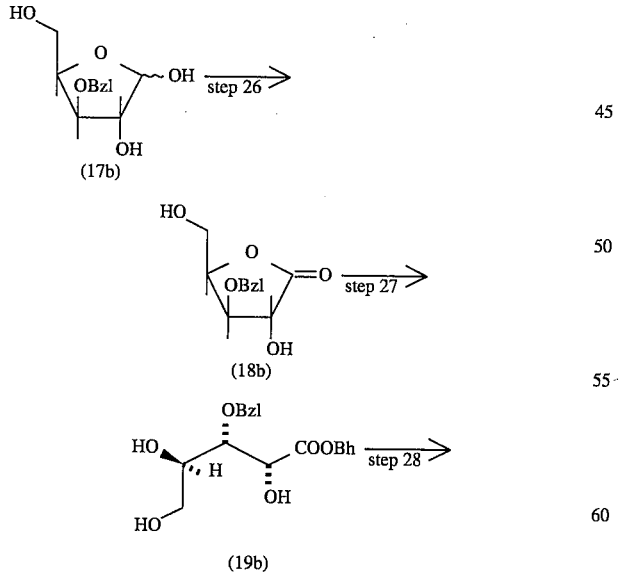

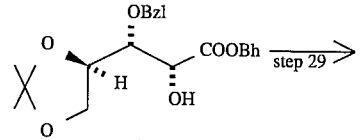

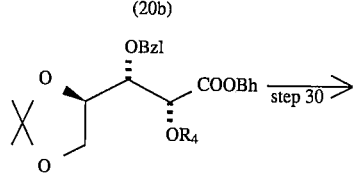

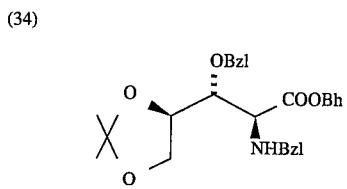

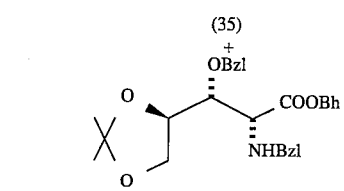

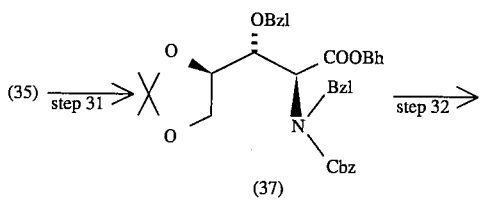

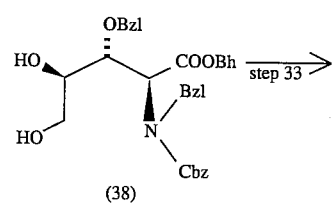

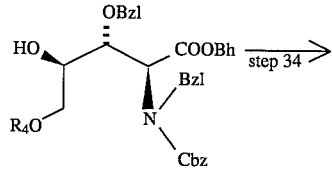

-continued
<Process C>

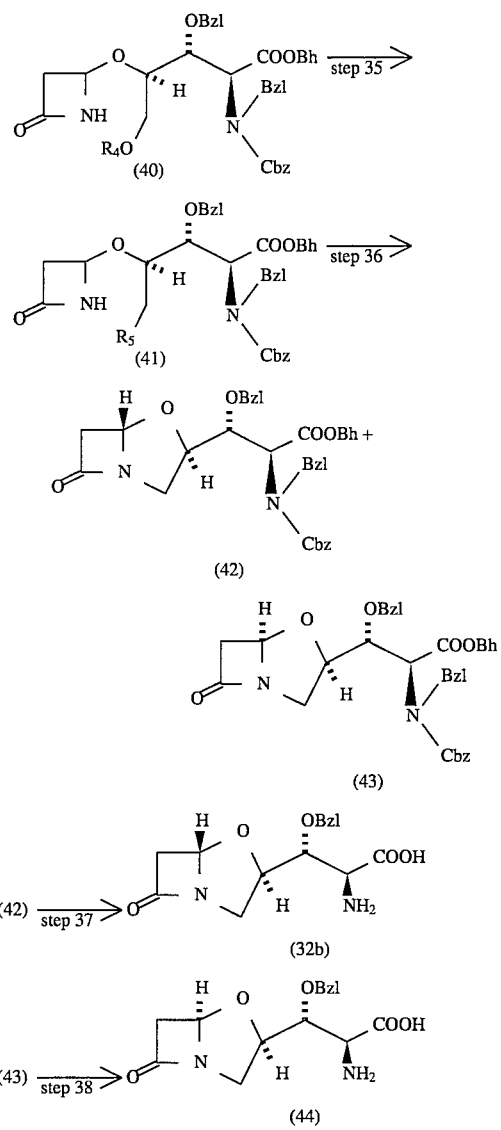

wherein $R_4$ and $R_6$ are as defined above, $R_5$ is a halogen atom, Bzl is a benzyl group, Bh is a benzhydryl group and Cbz is a benzyloxycarbonyl group.

The steps in the Reaction Schem illustrated above are executed as described below in detail.

<Step 26>

A known compound (17b) (Bull. Chem. Soc. Jap., 40., 2150 (1967)) is reacted in the same manner as in the step 12, giving a compound (18b).

The compound (18b) prepared by the reaction can be used in the next step after isolation, when so required.

<Step 27>

The compound (18b) prepared in the step 26 is reacted in the same manner as in the step 13, giving a compound (19b).

The compound (19b) prepared by the reaction can be used in the next step after isolation, when so required.

<Step 28>

The compound (19b) prepared in the step 27 is reacted in the same manner as in the step 14, giving a compound (20b).

The compound (20b) prepared by the reaction can be used in the next step after isolation, when so required.

<Step 29>

The compound (20b) obtained in the step 28 is reacted with a reactive derivative of sulfonic acid in a suitable solvent in the presence of a basic compound, giving a compound (34).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamde, etc. These solvents can be used singly or in mixture with one another.

Examples of useful basic compounds are organic basic compounds including tertiary amines such as triethylamine, pyridine, etc. and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc., alkali metals such as sodium, potassium, etc., and hydrides of alkali metals such as sodium hydride, etc.

Useful reactive derivatives of sulfonic acids are, for example, methanesulfonyl chloride, methanesulfonic anhydride, trifluoromethanesulfonic anhydride, 4-chlorobenzenesulfonyl chloride, p-toluenesulfonyl chloride, p-toluenesulfonic anhydride, etc.

As to the proportions of the compounds used in the reaction, it is suitable to use 1 to 4 mole equivalents of the reactive derivative of sulfonic acid and 1 to 20 mole equivalents of the basic compound, per mole of the compound (20b). The reaction advantageously proceeds if the reaction temperature is in the range of approximately 0° C. to the boiling point of the solvent, preferably 0° C. to room temperature and the reaction time is in the range of 0.5 to 8 hours, preferably 1 to 5 hours.

When required, the compound (34) prepared by the reaction is isolated from the reaction product before use in the next step.

<Step 30>

The compound (34) obtained in the step 29 is reacted with benzylamine in a suitable solvent in the presence or the absence of a basic compound, giving a compound (35) and a compound (36).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds including tertiary amines such as triethylamine, pyridine, etc. and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogenacarbonate, etc., alkali metals such as sodium, potassium, etc., and hydrides of alkali metals such as sodium hydride, etc.

As to the proportions of the compounds used in the reaction, it is suitable to use 1 to 20 mole equivalents of the benzylamine and 1 to 10 mole equivalents of the basic compound, per mole of the compound (34). The reaction advantageously proceeds if the reaction temperature is in the range of approximately 0° C. to the boiling point of the solvent, preferably approximately room temperature, and the reaction time is in the range of 1 to 48 hours, preferably 1 to 30 hours.

The compounds (35) and (36) prepared by the reaction are isolated from the reaction product before use in the next step, when so required. It is desirable to use isolated compounds in the next step.

<Step 31>

The compound (35) obtained in the step 30 is reacted with benzyl chloroformate in a suitable solvent in the presence of a basic compound, giving a compound (37).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic tertiary amines such as pyridine, triethylamine, etc., hydroxides of alkali metals such as sodium hydroxide, potassium hydroxide, etc., carbonates of alkali metals such as sodium carbonate, potassium carbonate, etc. and hydrogencarbonates of alkali metals such as sodium hydrogencarbonate, potassium hydrogencarbonate, etc.

As to the proportions of the compounds used in the reaction, it is suitable to use 1 to 10 mole equivalents, preferably 1 to 5 mole equivalents, of the benzyl chloroformate and 1 to 20 mole equivalents, preferably 2 to 15 mole equivalents, of the basic compound, per mole of the compound (35). The reaction advantageously proceeds if the reaction temperature is in the range of approximately 0° C. to the boiling point of the solvent, preferably 0° to 40° C. and the reaction time is in the range of 1 to 48 hours, preferably 1 to 24 hours.

When required, the compound (37) prepared by the reaction is isolated from the reaction-product before use in the next step.

<Step 32>

The compound (37) obtained in the step 31 is reacted with an acidic compound in a suitable solvent, giving a compound (38).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful acidic compounds are hydrogen halides such as hydrogen chloride, hydrogen bromide, etc., inorganic acids such as hydrochloric acid, sulfuric acid, etc., organic acids, e.g. carboxylic acids such as acetic acid, oxalic acid, etc. and sulfonic acids such as p-toluenesulfonic acid, etc., Lewis acids such as zinc chloride, ferric chloride, boron chloride, etc. and acidic cation exchange resins such as Dowex 50W, etc.

As to the proportions of the compounds used in the reaction, it is suitable to use 0.1 to 20 mole equivalents, preferably 1 to 5 mole equivalents, of the acidic compound, per mole of the compound (37). The reaction advantageously proceeds if the reaction temperature is in the range of approximately 0° C. to the boiling point of the solvent, preferably room temperature to 100° C. and the reaction time is in the range of 0.5 to 24 hours, preferably 1 to 12 hours.

When required, the compound (38) prepared by the reaction is isolated from the reaction product before use in the next step.

<Step 33>

The compound (38) obtained in the step 32 is reacted with a reactive sulfonic acid derivative in a suitable solvent in the presence of a basic compound, giving a compound (39).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds including tertiary amines such as triethylamine, pyridine, etc. and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc., alkali metals such as sodium, potassium, etc., and hydrides of alkali metals such as sodium hydride, etc.

Useful reactive sulfonic acid derivatives are, for example, methanesulfonyl chloride, methanesulfonic anhydride, trifluoromethanesulfonic anhydride, 4-chlorobenzenesulfonyl chloride, p-toluenesulfonyl chloride, p-toluenesulfonic anhydride, etc.

As to the proportions of the compounds used in the reaction, it is suitable to use 1 to 4 mole equivalents of the reactive sulfonic acid derivative and 1 to 20 mole equivalents of the basic compound, per mole of the compound (38). The reaction advantageously proceeds if the reaction temperature is in the range of approximately −20° C. to the boiling point of the solvent, preferably −10° C. to room temperature and the reaction time is in the range of 0.5 to 24 hours.

When required, the compound (39) prepared by the reaction is isolated from the reaction product before use in the next step.

<Step 34>

The compound (39) prepared in the step 33 is reacted with 4-acetoxyazetidin-2-one in a suitable solvent in the presence of a basic compound and a catalyst, giving a compound (40).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., and aprotic polar solvents such as acetonitrile, N,N-dimethylformamide, dimethylsulfoxide, hexamethylphosphoric triamide, etc. These solvents can be used singly or in mixture with one another. Among them, solvents treated for drying are preferred.

Examples of useful basic compounds are organic basic compounds including tertiary amines such as triethylamine, pyridine, etc. and secondary amines such as piperidine, etc., and inorganic basic compounds including hydroxides of alkali metals such as sodium hydroxide, potassium hydroxide, etc., carbonates of alkali metals such as sodium carbonate, potassium carbonate, etc., hydrogencarbonates of alkali metals such as sodium hydrogencarbonate, potassium hydrogencarbonate, etc., alkali metals such as sodium, potassium, etc., and hydrides of alkali metals such as sodium hydride, etc.

Useful catalysts are, for example, zinc acetate, palladium acetate, etc.

As to the proportions of the compounds used in the reaction, it is suitable to use 1 to 10 mole equivalents, preferably 1 to 5 mole equivalents, of the basic compound, 0.01 to 5 mole equivalents, preferably 0.1 to 2 mole equivalents, of the catalyst and 1 to 5 mole equivalents, preferably 1 to 3 mole equivalents, of the 4-acetoxyazetidin-2-one, per mole of the compound (39). The reaction advantageously proceeds if the reaction temperature is in the range of approximately 0° C. to the boiling point of the solvent, preferably 0° C. to 50° C. and the reaction time is in the range of 1 to 48 hours.

When required, the compound (40) prepared by the reaction is isolated from the reaction product before use in the next step.

<Step 35>

The compound (40) prepared in the step 34 is reacted with a halogenated alkali metal in a suitable solvent, giving a compound (41).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful halogenated alkali metals are lithium bromide, sodium bromide, potassium bromide, sodium iodide, potassium iodide, etc.

As to the proportions of the compounds used in the reaction, it is suitable to use 1 to 20 mole equivalents, preferably 1 to 10 mole equivalents, of the halogenated alkali metal, per mole of the compound (40). The reaction advantageously proceeds if the reaction temperature is in the range of approximately room temperature to the boiling point of the solvent and the reaction time is in the range of 1 to 24 hours, preferably 1 to 15 hours.

When required, the compound (41) prepared by the reaction is isolated from the reaction product before use in the next step.

<Step 36>

The compound (41) prepared in the step 35 is reacted with a basic compound in a suitable solvent, giving a compound (42) and a compound (43).

Solvents useful in the reaction are not critical and can be suitably selected from solvents which do not participate in the reaction. Useful solvents include, for example, hydrocarbons such as hexane, benzene, etc., ethers such as diethyl ether, tetrahydrofuran, dioxane, etc., halogenated hydrocarbons such as dichloromethane, chloroform, etc., alkyl ketones such as acetone, etc., esters such as ethyl acetate, etc., alcohols such as methanol, ethanol, etc., and aprotic polar solvents such as acetonitrile, N,N-dimethylformamide, dimethylsulfoxide, hexamethylphosphoric triamide, etc. These solvents can be used singly or in mixture with one another.

Examples of useful basic compounds are organic basic compounds such as triethylamine, pyridine, piperidine, 1,8-diazabicyclo[5.4.0]undec-7-ene, etc., and inorganic basic compounds including hydroxides of alkali metals such as sodium hydroxide, potassium hydroxide, etc., carbonates of alkali metals such as sodium carbonate, potassium carbonate, cesium carbonate, etc., hydrogencarbonates of alkali metals such as sodium hydrogencarbonate, potassium hydrogencarbonate, cesium hydrogencarbonate, etc., alkali metals such as sodium, potassium, etc., hydrides of alkali metals such as sodium hydride, etc., silver compounds such as silver trifluoromethanesulfonate, silver 2,2-dimethyl-6,6,7,7,8,8,8-heptafluoro-3,5-octanedionate, etc., and alcolates of alkali metals such as sodium methoxide, potassium t-butoxide, etc.

As to the proportions of the compounds used in the reaction, it is suitable to use 1 to 10 mole equivalents, preferably 1 to 5 mole equivalents, of the basic compound, per mole of the compound (41). The reaction advantageously proceeds if the reaction temperature is in the range of approximately 0° C. to the boiling point of the solvent, preferably room temperature to 100° C. and the reaction time is in the range of 0.5 to 50 hours, preferably 1 to 30 hours.

When required, the compounds (42) and (43) prepared by the reaction are isolated from the reaction product before use in the next step.

<Step 37 and Step 38>

In the steps 37 and 38, the compounds (42) and (43) prepared in the step 36 are subjected to catalytic reduction in a suitable solvent in the presence of a catalyst, giving a compound (32b) and a compound (44), respectively.

Useful solvents are not specifically limited insofar as they do not participate in the reaction. Examples of such solvents are tetrahydrofuran, dioxane, methanol, ethanol, ethyl acetate, N,N-dimethylformamide, acetic acid, water, etc. These solvents can be used singly or in mixture with one another.

Useful catalysts include, for example, metals of the VIII group supported by various carriers, such as palladium-carbon, palladium-alumina, palladium-asbestos, palladium barium carbonate, palladium-barium sulfate, palladium black, palladium-calcium carbonate, platinum-carbon, platinum black, platinum-calcium carbonate, etc., and oxides of the VIII group metals such as palladium oxide, platinum oxide, etc.

As to the proportions of the compounds used in the reaction, it is suitable to use 0.1 to 10 mole equivalents of the catalyst per mole of the compound (42) or (43). The reaction advantageously proceeds if the hydrogen pressure is in the range of atmospheric pressure to 100 atm., preferably atmospheric pressure to 10 atm., the reaction temperature is in the range of approximately 0° to 100° C., preferably room temperature to 50° C., and the reaction time is in the range of 10 minutes to 48 hours, preferably 0.5 to 24 hours.

The process C includes processes for preparing two types of optically active compounds. Further two types of optically active compounds can be produced by repeating the reactions in the step 31 and the subsequent steps using the compound (36) and the resulting compounds. When the reactions in the step 26 and the successive steps are conducted using as the starting material 3-O-benzyl-D-ribofuranose, 3-O-benzyl-L-ribofuranose or 3-O-benzyl-L-xylofuranose in place of 3-O-benzyl-D-xylofuranose (17b), 12 types of optically active compounds can be prepared. Thus, all of 16 types of optically active compounds can be prepared.

The basic group-containing compound of the present invention obtained by the reactions can be converted to the form of a salt of basic group by conventional methods, for example, by reacting the compound with said inorganic acid or organic acid in a suitable solvent at around room temperature. The acidic group-containing compound of the present invention prepared by reaction can be converted to the form of a salt of acidic group by conventional methods, for example, by reacting the compound with said alkali metal, alkaline earth metal or amine in a suitable solvent at around room temperature.

The compound of the present invention prepared by the above procedure can be separated from the reaction product by conventional methods of separation, followed by purification. Useful separation and purification methods include chromatography, recrystallization, distillation under a reduced pressure, etc.

The compound and a salt thereof according to the present invention can be formulated by per se conventional methods into pharmaceutical composition using a suitable carrier. Useful carriers include a variety of carriers conventionally used in preparing pharmaceutical preparations, such as excipients, fillers, extenders, binders, disintegrating agents, coloring agents, savor corrigents, lubricants, surfactants and the like.

The compound of the present invention can be administered to mammals including humans to treat malignant tumor. Administration unit forms of pharmaceutical compositions are not specifically limited and can be varied and selected so as to meet various therapeutical purposes. Typical examples of the forms are parenteral forms such as injection, suppositories, ophthalmic solutions, collunariums, ointments, plasters, aerosols, etc., and oral forms such as tablets, coated tablets, powders, granules, particles, capsules, solutions, pills, suspensions, emulsions, syrups, etc.

The compound of the present invention can be made into these pharmaceutical preparations by methods known in the art. For the manufacture of oral solid preparations such as tablets, powders, granules, etc., a wide variety of carriers can be used. Thus, use can be made of, for example, vehicles or excipients such as lactose, sucrose, sodium chloride, glucose, urea, starch, calcium carbonate, kaolin, crystalline cellulose, gum arabic, etc., binders such as simple syrup, glucose solution, starch solution, gelatine solution, polyvinyl alcohol, polyvinyl ether, polyvinyl pyrrolidone, carboxymethyl cellulose, hydroxypropyl cellulose, hydroxypropyl starch, methyl cellulose, ethyl cellulose, shellac, water, ethanol, propanol, potassium phosphate, etc., disintegrating agents, such as dry starch, sodium alginate, powdered agar, powdered laminaran, sodium hydrogencarbonate, calcium carbonate, polyoxyethylene sorbitan fatty acid esters, sodium lauryl sulfate, stearic acid monoglyceride, starch, lactose, etc., antidisintegrators such as sucrose, stearic acid, cacao butter, hydrogenated oils, etc., absorption promoters such as quarternary ammonium bases, sodium lauryl sulfate, etc., wetting agents or humectants such as glycerol, starch, etc., adsorbents such as starch, lactose, kaolin, bentonite, colloidal silica, etc., lubricants such as purified talc, stearic acid salts, powdered boric acid, polyethylene glycol, etc., and savor corrigents such as sucrose, orange peels, citric acid, tartaric acid, etc. When necessary, the tablets may further be provided with a conventional coating to give, for example, sugar-coated tablets, gelatincoated tablets, enteric-coated tablets, film-coated tablets, or double-coated or multi-coated tablets.

For the manufacture of pills, a wide variety of carriers can be used. Examples are vehicles or excipients such as glucose, lactose, starch, cacao butter, hardened vegetable oils, kaolin and talc, binders such as powdered gum arabic, powdered gum tragacanth, gelatin and ethanol, and disintegrating agents such as laminaran and agar.

For the manufacture of capsules, the compound of the invention is admixed with various carriers given above and the mixture is encapsulated into a hard capsules, soft capsules, etc.

For the manufacture of suppositories, a wide variety of carriers are used in mixture with a suitable absorption promotor. Examples of useful carriers are polyethylene glycol, cacao butter, lanolin, higher alcohols, higher alcohol esters, gelatin, semisynthetic glycerides, and Witepsol (trademark, a product of Dynamite Nobel Co., Ltd.).

In preparing injections, various carriers can be used which include, for example, diluents such as water, aqueous solutions of lactic acid, ethyl alcohol, macrogol, propylene glycol, ethoxylated isostearyl alcohol, polyoxylated isostearyl alcohol, polyoxyethylene sorbitan fatty acid esters, etc., pH modifiers and buffers such as sodium citrate, sodium acetate, sodium phosphate, etc., and stabilizers such as sodium pyrosulfite, ethylenediaminetetraacetic acid, thioglycolic acid, thiolactic acid, etc. In this case, the pharmaceutical preparations may contain sodium chloride, glucose or glycerol in an amount sufficient to give isotonic solutions. It is possible to add conventional solubilizing agents, soothing agents or local anesthetics, etc. The compound is admixed with these carriers and the mixture is made into an injection for a subcutaneous, intramuscular or intravenous use in a manner known per se. Liquid preparations may be aqueous or oily suspensions, solutions, syrup or elixir. They are formulated in the conventional manner using usual additives.

In shaping into the form of ointments such as pastes, creams or gels, diluents such as white petrolatum, paraffins, glycerol, cellulose derivatives, polyethylene glycols, silicones, bentonite, Japan wax, octyl dodecyl alcohol, etc. As preservatives, there can be mentioned methyl p-hydroxybenzoate, ethyl p-hydroxybenzoate, propyl p-hydroxybenzoate, etc.

For the preparation of plasters, said ointment, cream, gel or paste of the drug is applied to support commonly employed in the art in the conventional manner. Suitable examples of supports are woven or non-woven fabrics of cotton, rayon, chemical fibers or the like and films or foamed sheets of soft vinyl chloride, polyethylene, polyurethane or the like.

Furthermore, when necessary, the pharmaceutical preparations may contain coloring agents, preservatives, perfumes, flavors, sweetners and the like as well as other drugs.

The proportion of the compound of the invention in these pharmaceutical preparations is not critical but may suitably be selected from a wide range. Generally, however, the proportion is recommendably selected within the range of about 1 to about 70% by weight.

The route of administration of the pharmaceutical preparations of this invention is not critical and may be, for example, intestinal, oral, rectal, stomatic or percutaneous, but is selected according to the dosage form, the patient's age, sex and other factors and the severity of the disease to be treated. Thus, for instance, when they are provided in the form of tablets, pills, powders, solutions, suspensions, emulsions, granules or capsules, the preparations are administered orally. Injectable solutions are administered intravenously, either alone or in admixture with conventional fluids for parenteral infusion containing glucose, amino acids and so on. When necessary, these solutions may also be administered as they are by intraarterial, intramuscular, intradermal, subcutaneous or intraperitoneal route. Suppositories are administered rectally. Ointments are applied to the skin, oral mucosa, etc.

While the dosage of the above pharmaceutical preparations is dependent on the method of administration, the patient's age, sex, other background factors, severity of the disease and so on, it is generally recommended to administer about 1 to about 5000 mg, preferably about 10 to about 2000 mg of the compound of the invention, per day for a human adult. The preparation is preferably administered in a single dose or in two to four divided doses per day.

The present invention will be described below in more detail with reference to Examples, Formulation Examples and Test Examples.

Synthesis of present compounds by process A

Reference Example 1

Synthesis of benzyl (triphenylphosphoranylidene)acetate

A 22.9 g quantity of benzyl bromoacetate was dissolved in 100 ml of dry benzene. A 26.2 g quantity of triphenylphosphine was added thereto at room temperature and stirred overnight. The precipitated solids were collected by filtration, washed with benzene and dissolved in 250 ml of dichloromethane. A 14 ml quantity of triethylamine was added with ice-cooling and stirred with ice-cooling for 30 minutes and at room temperature for a further 30 minutes. The reaction mixture was transferred to a separating funnel, washed with water and dried over magnesium sulfate. The solvent was distilled off and diethyl ether was added to the residue. The resulting precipitate was collected by filtration to provide the title compound as white crystals (yield 41%).

$^1$H-NMR (CDCl$_3$) δ: 3.46 (br.s, 1H), 5.02 (br.s, 2H), 7.36–7.68 (m, 20H)

EXAMPLE 1

Synthesis of benzyl E-3-[(3'R,5'S)-7'-oxo-1'-aza-4'-oxabicyclo[3.2.0]hept-3'-yl]acrylate (2) and benzyl Z-3-[(3'R,5'S)-7'-oxo-1'-aza-4'-oxabicyclo[3.2.0]hept-3'-yl]acrylate (3)

A 355 µl quantity of anhydrous trifluoroacetic acid was added dropwise to a solution of 276 mg of 2-hydroxymethylclavam (1) and 301 µl of dimethyl sulfoxide in 8 ml of dichloromethane in a nitrogen atmosphere at −78° C. and allowed to react for 0.5 hour. A 0.8 ml quantity of triethylamine was added dropwise and stirred for 15 minutes. A 790 mg quantity of benzyl (triphenylphosphoranylidene)acetate was added and the temperature was gradually elevated to room temperature. The reaction mixture was diluted with ethyl acetate, washed with water and a saturated saline solution and dried over magnesium sulfate. After distilling off the solvent, the residue was subjected to silica gel column chromatography and eluted with hexane-ethyl acetate, giving 216 mg of the title compound (2) as an oil (yield 41%) and 80 mg of the title compound (3) as an oil (yield 15%).

Compound (2)

$[\alpha]_D^{23}$=−48.0° (C 0.5, CDCl$_3$)

IR (Neat) νmax (cm$^{-1}$): 1781, 1716, 1165

$^1$H-NMR (CDCl$_3$) δ: 2.74 (dd, J=6.8, 11.5 Hz, 1H), 2.90 (d, J=16.1 Hz, 1H), 3.34 (dd, J=2.3, 15.9 Hz, 1H), 4.10 (dd, J=6.7, 11.7 Hz, 1H), 4.80–4.90 (m, 1H), 5.20 (s, 2H), 5.40 (d, J=2.7 Hz, 1H), 6.16 (dd, J=1.5, 15.6 Hz, 1H), 6.87 (dd, J=5.2, 15.6 Hz, 1H), 7.37 (s, 5H)

Compound (3)

$[\alpha]_D^{23}$=−48.0° (C 0.5, CDCl$_3$)

$^1$H-NMR (CDCl$_3$) δ: 2.64 (dd, J=6.8, 11.7 Hz, 1H), 2.87 (d, J=15.9 Hz, 1H), 3.30 (dd, J=2.8, 16.5 Hz, 1H), 4.33 (dd, J=6.8, 11.8 Hz, 1H), 5.16 (s, 2H), 5.40 (d, J=2.7 Hz, 1H), 5.68 (ddd, J=1.8, 6.9, 13.7 Hz, 1H), 5.92 (dd, J=1.7, 11.6 Hz, 1H), 6.33 (dd, J=6.8, 11.6 Hz, 1H), 7.37 (s, 5H)

EXAMPLE 2

Synthesis of benzyl(2R,3R)-2,3-dihydroxy-3-[(3'R,5'S)-7'-oxo-1'-aza-4'-oxabicylo[3.2.0]hept-3'-yl]propionate (4) and benzyl(2S,3S)-2,3-dihydroxy-3-[(3'R,5'S)-7'-oxo-1'-aza-4'-oxabicyclo[3.2.0]hept-3'-yl]propionate (5)

A 216 mg quantity of the compound (2) obtained in Example 1 was dissolved in acetone (5 ml) and water (1 ml). A 185 mg quantity of N-methylmorphorine N-oxide and 1.0 ml of osmium tetroxide (2.5% t-butanol solution) were added at room temperature and stirred for 1 hour. The mixture was ice-cooled and a saturated aqueous solution of sodium hydrogensulfite was added. The precipitated solids were filtered off, and the filtrate was extracted with chloroform and dried over magnesium sulfate. After vacuum distillation for removal of the solvent, the residue was subjected to silica gel column chromatography and eluted gradiently with hexane-ethyl acetate, giving 100 mg of the title compound (4) as white crystals (yield 41%) and 70 mg of the title compound (5) as an oil (yield 29%).

Compound (4)

Melting point: 110.8°–111.5° C.

$[\alpha]_D^\leq$=−76.0° (C 0.5, CHCl$_3$)

IR (Nujol) νmax (cm$^{-1}$): 3385, 1791, 1756

$^1$H-NMR (CDCl$_3$) δ: 2.30 (br.d, 1H), 2.84 (d, J=16.7 Hz, 1H), 3.14 (br.s, 1H), 3.28 (dd, J=2.9, 16.0 Hz, 1H), 3.96 (br.t, 1H), 4.06 (dd, J=6.5, 12.1 Hz, 1H), 4.31 (dd, J=6.7, 14.2 Hz, 1H), 4.44 (br.s, 1H), 5.27 (s, 2H), 5.31 (d, J=2.6 Hz, 1H), 7.37 (s, 5H)

Compound (5)

$[\alpha]_D^{23}$=−68.0° (C 0.5, CHCl$_{13}$)

IR (Neat) νmax (cm$^{-1}$): 3740, 1777, 1750, 1121

$^1$H-NMR (CDCl$_3$) δ: 2.68 (d, J=8.2 Hz, 1H), 2.82 (d, J=16.6 Hz, 1H), 2.96 (dd, J=6.8, 11.1 Hz, 1H), 3.17–3.30 (m, 2H), 3.84–3.89 (m, 1H), 3.98 (dd, J=6.8, 11.6 Hz, 1H), 4.26–4.30 (m, 1H), 5.24 (d, J=2.5 HZ, 1H), 5.28 (d, J=3.6 Hz, 2H), 7.38 (s, 5H)

EXAMPLE 3

Synthesis of benzyl (2S,3R)-2,3-dihydroxy-3-[(3'R,5'S)-7'-oxo-1'-aza-4'-oxabicylo[3.2.0]hept-3'-yl]propionate (6) and benzyl(2R,3S)-2,3-dihydroxy-3-[(3'R,5'S)-7'-oxo-1'-aza-4'-oxabicyclo[3.2.0]hept-3'-yl]propionate (7)

The same procedure as in Example 2 was conducted except that 80 mg of the compound (3) obtained in Example 1 was used in place of the compound (2) used in Example 2. This procedure gave 10.2 mg of the title compound (6) as white crystals (yield 11%) and 9.1 mg of the title compound (7) as white crystals (yield 10%).

Compound (6)
Melting point: 97.5°–100.0° C.
$[\alpha]_D^{22} = -72.8°$ (C 0.19, CDCl$_3$)
IR (Nujol) νmax (cm$^{-1}$): 3425, 1790, 1711, 1216
$^1$H-NMR (CDCl$_3$) δ: 2.72 (d, J=7.7 Hz, 1H), 2.76 (d, J=16.2 Hz, 1H), 3.00 (d, J=8.1 Hz, 1H), 3.01 (dd, J=6.6, 11.9 Hz, 1H), 3.25 (dd, J=2.3, 16.1 Hz, 1H), 3.69–3.77 (m, 1H), 3.88 (dd, J=6.8, 11.5 Hz, 1H), 4.27–4.37 (m, 1H), 5.26 (s, 2H), 5.34 (d, J=2.6 Hz, 1H), 7.38 (s, 5H)

Compound (7)
Melting point: 114.5°–115.5° C.
$[\alpha]_D^{23} = -60.0°$ (C0.27, CDCl$_3$)
IR (Nujol) νmax (cm$^{-1}$): 3380, 1792, 1725, 1219
$^1$H-NMR (CDCl$_3$) δ: 2.39 (d, J=8.2 Hz, 1H), 2.66 (d, J=16.2 Hz, 1H), 2.99 (dd, J=6.0, 11.8 Hz, 1H), 3.10 (dd, J=4.4, 15.8 Hz, 1H), 3.86–3.96 (m, 1H), 3.98 (dd, J=6.8, 11.8 Hz, 1H), 4.30–4.41 (m, 1H), 4.42 (dd, J=3.6, 4.4 Hz, 1H), 4.91 (d, J=2.6 Hz, 1H), 5.18 (d, J=11.9 Hz, 1H), 5.33 (d, J=11.9 Hz, 1H), 7.38 (s, 5H)

EXAMPLE 4

Synthesis of benzyl 2(R)-(4''-chlorobenzenesulfonyloxy)-3(S)-hydroxy-3-[(3'R,5'S)-7'-oxo-1'-aza-4'-oxabicyclo[3.2.0]hept-3'-yl]propionate

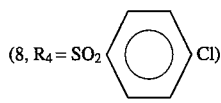

(8, R$_4$ = SO$_2$-C$_6$H$_4$-Cl)

A 41 μl quantity of triethylamine and 51 mg of 4-chlorobenzene sulfonyl chloride were added to a solution of 90 mg of the compound (4) obtained in Example 2 in 5 ml of dichloromethane at room temperature and stirred for 15 hours. The reaction mixture was subjected to silica gel column chromatography and eluted with hexane-ethyl acetate, giving 66 mg of the title compound as an oil (yield 47%).

$[\alpha]_D^{22} = -48.0°$ (C 0.17, CDCl$_3$)
IR (Neat) νmax (cm$^{-1}$): 3475, 1764, 1184
$^1$H-NMR (CDCl$_3$) δ: 2.17 (d, J=8.42 Hz, 1H), 2.73 (d, J=16.6 Hz, 1H), 2.96 (dd, J=6.1, 11.8 Hz, 1H), 3.25 (dd, J=2.4, 16.0 Hz, 1H), 4.00–4.21 (m, 3H), 5.16 (s, 2H), 5.26 (d, J=2.3 Hz, 2H), 7.30–7.40 (m, 5H)

EXAMPLE 5

Synthesis of benzyl 2(R)-azido-3(R)-hydroxy-3-[(3'R,5'S)-7'-oxo-1'-aza-4'-oxabicyclo[3.2.0]hept-3'-yl]propionate (9) and benzyl 2(S)-azido-3(R)-hydroxy-3-[(3'R,5'S)-7'-oxo-1'-aza-4'-oxabicyclo[3.2.0]hept-3'-yl]propionate (10)

A 23 mg quantity of sodium azide was added to a solution of 66 mg of the compound

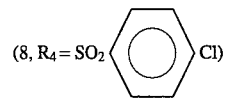

(8, R$_4$ = SO$_2$-C$_6$H$_4$-Cl)

obtained in Example 4 in 5 ml of dimethyl sulfoxide. After stirring at 60°–70° C. for 3.5 hours, the reaction mixture was dissolved in ethyl acetate, washed with water and a saturated saline solution and dried over magnesium sulfate. After vacuum distillation for removal of the solvent, the residue was subjected to silica gel column chromatography and eluted with hexane-ethyl acetate, giving 21 mg of the title compound (9) as white crystals (yield 46%) and 5 mg of the title compound (10) as an oil (yield 11%).

Compound (9)
Melting point: 91°–92.1° C.
$[\alpha]_D^{22} = +12.0°$ (C 0.33, CDCl$_3$)
IR (Nujol) νmax (cm$^{-1}$): 3415, 2135, 1801, 1726
$^1$H-NMR (CDCl$_3$) δ: 2.41 (d, J=7.7 Hz, 1H), 2.71 (d, J=16.2 Hz, 1H), 2.96 (dd, J=6.1, 11.7 Hz, 1H), 3.15 (dd, J=2.8, 16.7 Hz, 1H), 3.94–4.10 (m, 2H), 4.25–4.35 (m, 2H), 5.03 (d, J=2.6 Hz, 1H), 5.22 (d, J=12.0 Hz, 1H), 5.32 (d, J=12.1 Hz, 1H), 7.39 (s, 5H)

Compound (10)
$[\alpha]_D^{22} = -96.0°$ (C 0.33, CDCl$_3$)
IR (Neat) νmax (cm$^{-1}$): 3415, 2135, 1801, 1726
$^1$H-NMR (CDCl$_3$) δ: 2.30 (d, J=7.4 Hz, 1H), 2.82 (d, J=16.6 Hz, 1H), 2.99 (dd, J=6.6, 12.0 Hz, 1H), 3.28 (dd, J=2.3, 16.2 Hz, 1H), 4.03–4.13 (m, 2H), 4.22–4.32 (m, 2H), 5.28 (d, J=3.1 Hz, 1H), 5.29 (s, 2H), 7.39 (s, 5H)

EXAMPLE 6

Synthesis of benzyl 2(R)-azido-3(R)-acetoxy-3-[(3'R,5'S)-7'-oxo-1'-aza-4'-oxabicyclo[3.2.0]hept-3'-yl]propionate (11a, R'=COCH$_3$)

A 6 μl quantity of triethylamine was added to a solution of 10 mg of the compound (9) obtained in Example 5 in 10 ml of dichloromethane. A 3.8 ml quantity of acetic anhydride was added dropwise with ice-cooling and stirred for 15 hours. The reaction mixture was subjected to silica gel column chromatography and eluted with hexane-ethyl acetate, giving 6.4 mg of the title compound as an oil (yield 57%).

$[\alpha]_D^{22} = -16.3°$ (C 0 49, CDCl$_3$)
IR (Neat) νmax (cm$^{-1}$): 2115, 1783, 1748, 1219
$^1$H-NMR (CDCl$_3$) δ: 2.08 (s, 3H), 2.68 (d, J=16.2 Hz, 1H), 2.79 (dd, J=6.2, 11.9 Hz, 1H), 3.08 (dd, J=2.5, 16.5 Hz, 1H), 3.90 (dd, J=6.8, 11.9 Hz, 1H), 4.44 (d, J=3.16 Hz, 1H), 4.43–4.53 (m, 1H), 4.83 (d, J=2.5 Hz, 1H), 5.20 (d, J=12.0 Hz, 1H), 5.29–5.34 (m, 1H), 5.35 (d, J=11.8 Hz, 1H), 7.35–7.45 (m, 5H)

EXAMPLE 7

Synthesis of benzyl 2(R)-azido-3(R)-benzoyloxy-3-[(3'R, 5'S)-7'-oxo-1'-aza-4'-oxabicyclo[3.2.0]hept-3,-yl]propionate(11b, R'=COC₆H₅)

The same procedure as in Example 6 was conducted except that 89 mg of benzoyl chloride was used in place of acetic anhydride. A 110 mg of the title compound (11b, R'=COC₆H₅) was obtained as an oil from 110mg quantity of the compound (9) obtained in Example 5 (yield 49.5%).

$[\alpha]_D^{23}$=−63.4° (C 0.32, CHCl₃)

¹H-NMR(CDCl₃) δ: 2.71 (1H, d, J=16.12), 2.88–2.97 (1H, dd, J=6.27, 12.07), 3.05–3.15 (1H, dd, J=2.24, 16.02), 3.95–4.05 (1H, dd, 6.81, 11.89), 4.57–4.68 (2H, m,), 4.87 (1H, d, J=2.54), 5.19–5.41 (2H, dd, J=11.93, 31.89), 5.56–5.62 (1H, dd, J=3.04, 7.84), 7.35–7.66 (8H, m), 7.96–8.00 (2H, m).

EXAMPLE 8

Synthesis of 3(R)-acetoxy-2(R)-amino-3-[(3'R,5'S)-7'-oxo-1'-aza-4'-oxabicyclo[3.2.0]hept-3'-yl]propionic acid (12a, R'=COCH₃)

A 6.4 mg quantity of 10% palladium-carbon was added to a solution of 6.4 mg of the compound (11a, R'=COCH₃) obtained in Example 6 in methanol (4 ml) and ethyl acetate (1 ml) and shaken in a hydrogen stream at 50 psi for 1 hour. The precipitate was filtered off and the filtrate was distilled off under reduced pressure. Water/diethyl ether were added to the residue and the aqueous layer was separated and lyophilized, giving 1.7 mg of the title compound as white solids (yield 40%).

¹H-NMR (CDCl₃) δ: 2.16 (s, 3H), 2.97 (d, J=17.9 Hz, 1H), 2.99 (dd, J=6.0, 17.2 Hz, 1H), 3.40 (dd, J=2.7, 17.0 Hz, 1H), 4.11 (dd, J=6.6, 15.6 Hz, 1H), 4.15 (d, J=2.9 Hz, 1H), 4.38–4.49 (m, 1H), 5.37 (dd, J=2.6, 7.9 Hz, 1H), 5.43 (d, J=2.4 Hz, 1H).

EXAMPLE 9

Synthesis of 2(R)-amino-3(R)-benzoyloxy-3-[(3'R,5'S)-7'-oxo-1'-aza-4'-oxabicyclo[3.2.0]hept-3'-yl]propionic acid (12b, R'=COC₆H₅)

The same procedure as in Example 8 was conducted except that 130 mg of the compound (11b, R'=COC₆H₅) obtained in Example 7 was used in place of the compound (11a, R'=COCH₃) used in Example 8. This procedure gave 50 mg of the title compound (12b, R'=COC₆H₅) as solids (yield 52%).

$[\alpha]_D^{23}$=−100° (C 0.2, D₂O)

¹H-NMR(D₂O) δ: 2.84–3.50 (3H, m), 4.04–4.32 (2H, m), 4.85–4.98 (1H, dd, J=6.53, 14.45), 5.26–5.48 (1H, m), 5.58–5.70 (1H, m), 7.46–7.86 (5H, m)

Synthesis of present compounds by process B

EXAMPLE 10

Synthesis of 1,2-O-isopropylidene-5-O-triphenylmethyl-D-xylofuranose (14)

A mixture of 1,2-O-isopropylidene D-xylofuranose (13) (9.51 g), triphenylmethyl chloride (13.94 g), and pyridine (100 ml) was stirred at 100° C. for 1 hour under dried condition. Pyridine was removed in vacuo and the residue was diluted with diethyl ether, washed with 1N-hydrochloric acid, water, saturated sodium bicarbonate solution and brine successively, and then dried over magnesium sulfate. After removal of the solvent, the residue was purified by silica gel column chromatography and the title compound was obtained as foam.

Yield: 85.5%

$[\alpha]_D^{23}$=+18.0° (C 1.0, CHCl₃)

¹H-NMR(CDCl₃) δ: 1.33 (3H, s), 1.49 (3H, s), 3.14 (1H, d, J=2.6), 3.43–3.61 (2H, m), 4.25–4.27 (1H, m), 4.53 (1H, d, J=3.7), 6.01 (1H, d, J=3.7), 7.20–7.47 (15H, m)

IR (Neat) vmax (cm⁻¹): 3470, 2935

EXAMPLE 11

Synthesis of 1,2-O-isopropylidene-3-O-methyl-5-O-triphenylmethyl-D-xylofuranose (15a, R''=—CH₃)

To a solution of compound (14), obtained in the example 10 (8.37 g), in dimethyl sulfoxide (100 ml), sodium hydride (60% oil dispersion)(1.0 g) was added portionwise under room temperature. The reaction mixture was stirred under dried condition at room temperature for 3 hours. A solution of methyl iodide (1.32 ml) in dimethyl sulfoxide (5 ml) was added dropwise at room temperature and stirred overnight. The reaction mixture was diluted with diethyl ether, washed with water and brine and dried over magnesium sulfate. The residue, obtained after the removal of solvent, was purified by column chromatography and the title compound was obtained as foam.

Yield: 81.9%

$[\alpha]_D^{23}$=−51.0° (C 1.3, CHCl₃)

¹H-NMR(CDCl₃) δ: 1.32 (3H, s), 1.53 (3H, s), 3.33 (3H, s), 3.25–3.46 (2H, m), 3.78 (1H, d, J=3.1), 4.29–4.37 (1H, m), 4.54 (1H, d, J=3.8), 5.85 (1H, d, J=3.8), 7.18–7.48 (15H, m)

IR (Nujol) vmax (cm⁻¹): 2920, 1076

EXAMPLE 12

Synthesis of 3-O-benzyl-1,2-O-isopropylidene-5-O-triphenylmethyl-D-xylofuranose (15b, R=—CH₂C₆H₅)

Starting from 7.42 g of compound (14) and 4.40 g of benzyl bromide and following the procedure as described in Example 11, the title compound was obtained.

Yield: 8.84 g (98.7%)

¹H-NMR(CDCl₃) δ: 1.32 (3H, s), 1.52 (3H, s), 3.21–3.35 (1H, m), 3.51–3.58 (1H, m), 3.99 (1H, d, J=3.1), 4.35–4.45 (2H, m), 4.55–4.61 (2H, m), 5.89 (1H, d, J=3.8), 7.07–7.47 (20H, m)

EXAMPLE 13

Synthesis of 3-O-(4-fluorobenzyl)-1,2-O-isopropylidene-5-O-triphenylmethyl-D-xylofuranose (15c,

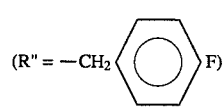

Starting from 11.2 g of compound (14) and 5.67 g of 4-fluorobenzyl bromide and following the procedure as described in Example 11, the title compound was obtained.

Yield: 13.0 g (93%)

$^1$H-NMR(CDCl$_3$) δ: 1.30 (3H, s), 1.54 (3H, s), 3.22–3.33 (1H, dd, J=2.25, 8.5), 3.50–3.60 (1H, dd, J=3.50, 9.75), 3.98 (1H, d, J=2.95), 4.34–4.45 (2H, m), 4.50–4.58 (2H, m), 5.88(1H, d, J=3.85), 6.85–7.08 (4H, m), 7.17–7.46 (15H, m).

EXAMPLE 14

Synthesis of 1,2-O-isopropylidene-3-O-(4-methoxybenzyl)-5-O-triphenylmethyl-D-xylofuranose (15d, R"=

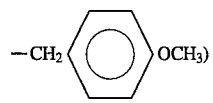

Starting from 20.0 g of compound (14) and 10.84 g of 4-methoxybenzyl bromide and following the procedure as described in Example 11, the title compound was obtained.

Yield: 25.06 g (98.1%)

$^1$H-NMR(CDCl$_3$) δ: 1.30 (3H, s), 1.51 (3H, s), 3.27 (1H, dd, J=6.6, 9.3), 3.54 (1H, dd, J=5.8, 9.3), 3.75 (3H, s), 3.96 (1H, d, J=3.1), 4.36–4.41 (2H, m), 4.46–4.55 (2H, m), 5.88 (1H, d, J=3.8), 6.75 (2H, d, J=6.6), 7.01 (2H, d, J=7.0), 7.16–7.47 (15H, m).

EXAMPLE 15

Synthesis of 3-O-cyclopropylmethyl-1,2-O-isopropylidene-5-O-triphenylmethyl-D-xylofuranose (15e, R"=

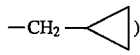

Starting from 26.0 g of compound (14) and 12.15 g of bromomethylcyclopropane and following the procedure as described in Example 11, the title compound was obtained.

Yield: 28.0 g (95.7%)

$^1$H-NMR(CDCl$_3$) δ: 0.18–0.27 (2H, m), 0.51–0.56 (2H, m), 1.00–1.07 (1H, m), 1.32 (3H, s), 1.51 (3H, s), 3.22–3.37 (3H, m), 3.47 (1H, dd, J=2.8, 3.4), 3.95 (1H, d, J=3.7), 4.30–4.42 (1H, m), 4.52 (1H, d, J=3.7), 5.89 (1H, d, J=3.7), 7.14–7.53 (15H, m).

EXAMPLE 16

Synthesis of 1,2-O-isopropylidene-3-O-methyl-D-xylofuranose (16a, R"=—CH$_3$)

Compound (15a), obtained in Example 11 (500 mg), was dissolved in 0.015N-hydrochloric acid in acetonitrile (37 ml) and stirred at room temperature for 3 hours. Saturated sodium hydrogencarbonate solution (a few ml) was added and stirred for 5 minutes at room temperature. After removal of solid by filtration, the solution was concentrated in vacuo and the residue was purified by silica gel column chromatography. The title compound was obtained as an oil.

Yield: 87.4%

$[α]_D^{23}$=−58.0° (C 1.0, CHCl$_3$)

$^1$H-NMR(CDCl$_3$) δ: 1.33 (3H, s), 1.50 (3H, s), 2.21 (1H, dd, J=4.3, 8.0), 3.44(3H, s,), 3.83 (1H, d, J=3.5), 3.,87–3.99 (1H, m), 4.26–4.32 (1H, m), 4.62 (1H, d, J=3.9), 5.96 (1H, d, J=3.9).

IR (Neat) νmax (cm$^{-1}$): 3475, 1078, 1011

EXAMPLE 17

Synthesis of 3-O-benzyl-1,2-O-isopropylidene-D-xylofuranose (16b, R"=—CH$_2$C$_6$H$_5$)

Starting from 6.34 g of compound (15b) and following the procedure as described in Example 16, the title compound was obtained.

Yield: 3.40 g (quant.)

$^1$H-NMR(CDCl$_3$) δ: 1.33 (3H, s), 1.48 (3H, s), 2.12–2.18 (1H, m), 3.81–3.99 (2H, m), 4.01 (1H, d, J=3.41), 4.25–4.32 (1H, dd, J=4.88, 8.79), 4.49 (1H, d, J=12.2), 4.63–4.65 (1H, d, J=3.42), 4.72 (1H, d, J=12.21), 5.99 (1H, d, J=3.9), 7.29–7.41 (5H, m)

EXAMPLE 18

Synthesis of 3-O-(4-fluorobenzyl)-1,2-O-isopropylidene-D-xylofuranose (16c,

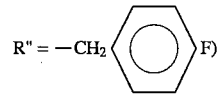

Starting from 13.0 g of compound (15c) and following the procedure as described in Example 16, the title compound was obtained.

Yield: 6.6 g (92%)

$^1$H-NMR(CDCl$_3$) δ: 1.33 (3H, s), 1.50 (3H, s), 2.05–2.12 (1H, m), 3.85–3.96 (2H, m), 4.01 (1H, d, J=3.42), 4.26–4.35 (1H, m), 4.47 (1H, d, J=11.70), 4.62–4.73 (2H, m), 6.00 (1H, d, J=3o91), 7.00–7.11 (2H, m), 7.26–7.35 (2H, m).

EXAMPLE 19

Synthesis of 1,2-O-isopropylidene-3-O-(4-methoxybenzyl)-D-xylofuranose (16d,

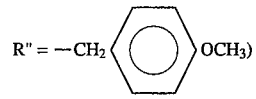

Starting from 25.5 g of compound (15d) and following the procedure as described in Example 16, the title compound was obtained.

Yield: 13.35 g (92.9%)

$^1$H-NMR(CDCl$_3$) δ: 1.33 (3H, s), 1.48 (3H, s), 2.27–2.33 (1H, m), 3.80 (3H, s), 3.84–3.97 (2H, m), 3.99(1H, d, J=3.5), 4.23–4.29 (1H, m), 4.41 (1H, d, J=11.6), 4.61–4.68 (2H, m), 5.97 (1H, d, J=3.8), 6.89 (2H, d, J=6.6), 7.24 (2H, d, J=6.7).

EXAMPLE 20

Synthesis of 3-O-cyclopropylmethyl-1,2-O-isopropylidene-D-xylofuranose (16e,

R" = —CH$_2$— 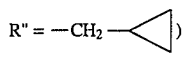 )

Starting from 28.0 g of compound (15e) and following the procedure as described in Example 16, the title compound was obtained.

Yield: 12.0 g (85.7%)

$^1$H-NMR(CDCl$_3$) δ: 0.19–0.28 (2H, m), 0.52–0.57 (2H, m), 0.99–1.07 (1H, m), 1.31 (3H, s), 1.47 (3H, s), 2.5 (1H, dd, J=4.1, 8.3), 3.26–3.35 (1H, m), 3.41–3.50 (1H, m), 3.88–3.97 (3H, m), 4.27 (1H, dd, J=4.9, 8.3), 4.52 (1H, d, J=3.9), 5.96 (1H, d, J=3.9).

EXAMPLE 21

Syntheses of 3-O-methyl-D-xylofuranose (17a, R"=CH$_3$) and 3-O-methyl-D-xylosic acid-γ-lactone (18a, R"=CH$_3$)

Compound (16a), obtained in example 16 (3.11 g), was dissolved in 50% acetic acid (100 ml) and stirred at 90° C. for 6 hours. After removal of solvent in vacuo, the title compound (17a) was obtained as a mixture. Without isolation, the residue was dissolved in 1,4-dioxane (40 ml) and water (20ml) with calcium carbonate (4.43 g). Bromine (2.0 ml) was added dropwise to this mixture at room temperature and stirred for 24 hours. The reaction mixture was diluted with ethyl acetate and washed with 5% sodium thiosulfate solution and brine and dried over magnesium sulfate. The residue, obtained after evaporation, was recrystallized from ethyl acetate-hexane, and the title compound (18a) was obtained as white solids. compound (18a)

Yield: 1.26 g (50.9%)

m.p.: 100.5°–102° C.

$[α]_D^{23}$=+56.9° (C 1.0, MeOH) $^1$H-NMR(DMSO-d$_6$) δ: 3.39 (3H, s), 3.58–3.62 (2H, m), 4.00 (1H, t, J=7.6), 4.41–4.48 (1H, m), 4.56–4.60 (1H, m), 4.99 (1H, t, J=5.3), 6.14 (1H, d, J=6.6)

IR (Nujol) νmax (cm$^{-1}$): 3435, 3385, 1765

EXAMPLE 22

Syntheses of diphenylmethyl 3-O-methyl-D-xylosate (19a, R"=—CH$_3$) and diphenylmethyl 3-O-methyl-4,5-O-isopropylidene-D-xylosate (20a, R"=—CH$_3$)

Compound (18a), obtained in example 21 (4.17 g), was suspended in water (10 ml) and 0.5N-lithium hydroxide solution was added dropwise at 5° C. and stirred for 30 minutes. Dowex 50W4 (40 g) was added to this mixture and stirred for 1 minute. After removal of the resin by filtration, the filtrate was lyophilized. Diphenyldiazomethane in acetone (5.0 g/100 ml) was added dropwise to the residue at room temperature and stirred for 2 hours. After removal of the solvent in vacuo, the residue was purified by silica gel column chromatography (CHCl$_{13}$-MeOH) and the desired triol was obtained as white solids (19a, 2.29 g). This solid was dissolved in dried acetone (50 ml) and copper (II) sulfate hexahydrate (5.48 g) was added at room temperature. The reaction mixture was stirred for 18 hours at room temperature and the solid stuff was removed by filtration. The residue, after evaporation, was purified by silica gel column chromatography and the title compound (20a) was obtained as solids.

compound (20a)

Yield: 4.59 g (46.2%)

m.p.: 132.4°–133.0° C.

$[α]_D^{23}$=+29.8° (C 0.47, CHCl$_3$)

$^1$H-NMR(CDCl$_3$) δ: 1.37 (3H, s), 1.44 (3H, s), 2.99 (1H, d, J=8.2), 3.21 (1H, s), 3.60 (1H, dd, J=1.8, 7.4), 3.82 (1H, dd, J=10.4, 10.4), 4.09 (1H, dd, J=6.4, 8.2), 4.19 (1H, dd, J=1.8, 8.1), 4.37 (1H, dd, J=7.3, 13.8), 7.03 (1H, s), 7.30–7.39 (10H, m)

IR (Nujol) νmax (cm$^{-1}$): 3395, 1760, 1137

EXAMPLE 23

Synthesis of diphenylmethyl 3-O-(4-fluorobenzyl)-4,5-O-isopropylidene-D-xylosate (20c:

R" = —CH$_2$ 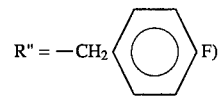 F)

by steps 11, 12, 13 and 14 from the compound (16c)

A solution of compound (16c) (6.6 g) in 60% acetic acid in water (75 ml) was heated at 90° C. for 4 hours. After concentration to dryness, the residual oil was dissolved in ethyl acetate, neutralized with sodium bicarbonate, washed with water (X2, 25 ml), dried over sodium sulfate and concentrated under vacuum. The crude compound (17c) (5.2g, 91%) was used for next reaction without purification.

Bromine (2.56 ml) was added dropwise to a mixture of compound (17c) (5.2 g), calcium carbonate (5.9 g) in 1,4-dioxane (28 ml) and water (12 ml) under stirring and ice cooling. After 18 hours stirring at room temperature, the reaction mixture was cooled down and sodium sulfite was added portionwise until the red colour of reaction mixture disappeared. Solid was filtered and the filtrate was concentrated. The residual oil was dissolved in ethyl acetate, washed with water, dried over sodium sulfate and concentrated under vacuum to give crude compound (18c) (2.7 g, 52%).

A solution of potassium hydroxide (0.5N, 26 ml) was added dropwise to a solution of compound (18c) (2.7 g) in 1,4-dioxane (13 ml) at 50° C. After 1 hour stirring at same temperature, the solvent was evaporated and the residue was dissolved in acetone and water (50 ml, 2:1). Dewex 50 was added portionwise to the solution until the pH was 3. After this the Dowex 50 was removed by filtration. To the ice cooled filtrate, diphenyldiazomethane (3.1 g) in acetone (30 ml) was added slowly. The reaction mixture was stirred at room temperature for 2 hours, acetone was removed by evaporation and residue was extracted with ethyl acetate. The organic extract was washed with water and brine, dried over sodium sulfate and concentrated under vacuum to give crude compound (19c) (3.2 g, 70%).

Copper sulfate (5.1 g) was added to a solution of compound (19c) (3.2 g) in acetone (40 ml) which was stirred at room temperature for 6 hours. Solid was removed by filtration. The filtrate was concentrated and the residue was purified over silica gel using ethyl acetate:hexane (1:4) as eluant to give the title compound (20c). Compound (20c)

Yield: 2.8 g (80%)

$^1$H-NMR(CDCl$_3$) δ: 1.37 (3H, s), 1.45 (3H, s), 3.05 (1H, d, J=8.62), 3.82–3.89 (2H, m), 4.07–4.17 (2H, m), 4.22–4.27 (1H, dd, J=1.70, 8.63), 4.36–4.47 (1H, dd, J=7.20, 13.86), 4.56–4.62 (1H, d, J=11.2), 6.82–7.01 (5H, m), 7.24–7.36 (10H, m).

EXAMPLE 24

Synthesis of diphenylmethyl 3-O-(4-methoxybenzyl)-4,5-O-isopropylidene-D-xylosate (20d,

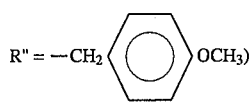

by steps 11, 12, 13 and 14 from the compound (16d).

A solution of compound (16d) (13.35 g) in 4N-HCl (51.42 ml) and THF (215 ml) was heated at 50° C. for 2.5 hours. The reaction mixture was cooled to room temperature, neutralized with sodium bicarbonate and extracted with ethyl acetate. The organic extract was dried over sodium sulfate and concentrated under vacuum. The crude compound was washed with hexane (x2, 100 ml) to give the compound (17d) (10.89 g, 93.6%). Without isolation, it was treated with bromine (5.25 ml) in the presence of calcium carbonated (11.77 g), 1,4-dioxane (74 ml) and water (24 ml). The desired compound (18d) (10.5 g, 97.2%) was obtained.

Thus obtained compound (18d) was hydrolysed with 0.5 N-KOH (96 ml) in 1,4-dioxane (51 ml) followed by acidification with dowex 50 to pH 3 and treatment with diphenyldiazomethane (11.69 g) gave crude compound (19d) (12.20 g, 67.3%). Compound (19d) was further reacted with acetone (330 ml) in the presence of copper sulfate (19.00 g) to give the title compound (20d).

Compound (20d)

Yield: 9.65 g (73.8%)

$^1$H-NMR(CDCl$_3$) δ: 1.37 (3H, s), 1.45 (3H, s), 3.12 (1H, d, J=8.6), 3.82 (3H, s), 3.80–3.88 (2H, m), 4.06–4.13 (2H, m), 4.21–4.26 (1H, dd, J=1.6, 8.6), 4.36–4.46 (1H, dd, J=7.2, 13.9), 4.52 (1H, d, J=11.2), 6.67 (1H, d, J=8.4), 6.92 (1H, dd, J=2.1, 9.5), 6.99 (1H, s), 7.24–7.34 (12H, m).

EXAMPLE 25

Synthesis of diphenylmethyl 3-O-cyclopropylmethyl-4,5-O-isopropylidene-D-xylosate (20e,

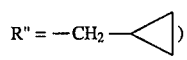

by steps 11, 12, 13 and 14 from the compound (16e)

Following the procedure as described above, and starting from compound (16e) (12 g) and 60% acetic acid in water (168 ml), the compound (17e) (7.86 g, 78.6%) was obtained. It was treated with bromine (4.94 ml) in the presence of calcium carbonate (11.23 g), 1,4-dioxane (54 ml) and water (23 ml). The desired compound (18e) (6.50 g 84%) was obtained.

Thus obtained compound (18e) was hydrolysed with 0.5 N-KOH(77 ml) in 1,4-dioxane (39 ml) followed by acidification with dowex 50 to pH 3 and treatment with diphenyldiazomethane (9.25 g) gave crude compound (19e ) (12.34 g, 98% ). Compound (19e) was further reacted with acetone (390ml ) in presence of copper sulphate (22.34 g, 140 mmol) to give the title compound (20e).

Compound (20e)

Yield: 7.45 g (56.4%)

$[α]_D^{24}$=+26° (C 2.0, CHCl$_3$)

$^1$H-NMR(CDCl$_3$) δ: 0.00–0.03 (2H, m), 0.36–0.40 (2H, m), 0.71–0.88 (1H, m), 1.44 (3H, s), 1.51 (3H, s), 2.99 (1H, dd, J=7.0, 9.9), 3.29 (1H, d, J=8.8), 3.45 (1H, dd, J=6.8, 10.0), 3.81 (1H, dd, J=1.6, 7.1), 3.96 (1H, t, J=7.8), 4.18 (1H, dd, J=1.9, 3.9), 4.31 (1H, dd, J=1.6, 8.8), 4.46 (1H, t, J=7.1), 7.10 (1H, s), 7.34–7.50 (10H, m).

EXAMPLE 26

Synthesis of diphenylmethyl 3-O-benzyl-4,5-O-isopropylidene-D-xylosate (20b, R"=—CH$_2$C$_6$H$_5$) by steps 11, 12, 13 and 14 from the compound (16b)

Following the procedures as described in Example 23, 24 and 25 and starting from the compound (16b ), the title compounds (18b), (19b) and (20b) were obtained.

Compound (18b)

m.p.: 102°–103° C.

$[α]_D^{14}$=+35.1° (C 0.114, CH$_3$OH)

IR (KBr) vmax (cm$^{-1}$): 3480, 3380, 1770

Mass m/z(EI): 238[M]$^+$, 91 (CH$_2$Ph)$^+$ $^1$H-NMR(C$_2$D$_2$Cl$_4$) δ: 7.40–7.33 (m, 5H), 4.83 (d, J=11.86 Hz, 1H), 4.73 (d, J=7.74 Hz, 1H), 4.68 (d, J=11.86 Hz, 1H), 4.58–4.55 (m, 1H), 4.42 (dd, J$_1$=7.92 Hz, J$_2$=7.92 Hz, 1H), 3.97–3.94 (dd, J$_1$=2.64 Hz, J$_2$=12.87 Hz, 1H), 3.88–3.85 (dd, J$_1$=3.0 Hz, J$_2$=12.86 Hz, 1H), 2.2 (s, 2H).

Compound (19b )

m.p.: 100.5°–101.5° C.

$[α]_D^{14}$=+20.0° (C 0.052, EtOH)

IR (film) vmax (cm$^{-1}$): 3430, 3350, 1740

Mass m/z(EI): 442 [M]$^+$, 239 [M-OCH$_2$Ph]$^+$, 167 [CHPh$_2$]$^+$, 91 [CH$_2$Ph]$^+$ $^1$H-NMR(CD$_3$ OD) δ: 7.38–7.08 (m, 15H), 6.93 (s, 1H), 4.56 (d, J=2.16 Hz, 1H), 4.52 (d, J=11.19 Hz, 1H), 4.27 (d, J=11.16 Hz, 1H), 4.00 (dd, J$_1$=2.14 Hz, J$_2$=5.81 Hz, 1H), 3.92–3.89 (q, 1H), 3.74–3.67 (m, 2H).

Compound (20b )

m.p.: 68°–69° C.

$[α]_D^{14}$=+32.1° (C 0.118, CHCl$_3$)

IR (film ) vmax (cm$^{-1}$): 3450, 1740, 1380, 1370

Mass m/z(EI): 461 [M-1]$^+$, 295 [M-CHph$_2$]$^+$, 183 [OCHph$_2$]$^+$, 167 [CHph$_2$]$^+$, 91 [CH$_2$Ph]$^+$ $^1$H-NMR(C$_2$D$_2$Cl$_4$) δ: 7.34–6.99 (m, 15H), 6.94 (s, 1H), 4.59 (d, J=11.30 Hz, 1H), 4.41–4.37 (q, 1H), 4.26 (s, 1H), 4.19 (d, J=11.29 Hz, 1H), 4.07 (dd, J$_1$=6.45 Hz, J$_2$=8.78 Hz, 1H), 3.88 (dd, J$_1$=7.20Hz, J$_2$=8.24 Hz, 1H), 3.86 (dd, J$_1$=2.42 Hz, J$_2$=7.08 Hz, 1H), 3.1 (s, 1H), 1.44(s, 3H), 1.36 (s, 3H).

EXAMPLE 27

Synthesis of diphenylmethyl 2-O-t-butyldimethylsilyl-3-O-methyl-4,5-O-isopropylidene-D-xylosate (21a, R"=—CH$_3$, R$_5$=TBDMS)

A mixture of compound (20a), obtained in Example 22 (2.23 g), imidazole(786 mg) and t-butyldimethylsilyl chloride (1.74 g) in N,N-dimethylformamide (100 ml) was stirred at 60° C. for 5 days. The reaction mixture was diluted with benzene and washed with water and brine and dried over magnesium sulfate. The residue, obtained after evaporation, was purified by silica gel chromatography and the title compound was obtained as an oil.

Yield: 2.69 g (93.1%)

$[\alpha]_D^{23}$=+26.0° (C 0.46, CHCl$_3$)

$^1$H-NMR(CDCl$_3$) δ: 0.00 (9H, s), 0.86 (6H, s), 1.28 (3H, s), 1.40 (3H, s), 3.40–3.47 (1H, m), 3.47 (3H, s), 3.74 (1H, dd, J=7.4, 7.4), 3.97–4.15 (2H, m), 4.44 (1H, d, J=4.4), 7.26 (1H, s), 7.30–7.39 (10H, m)

IR (Neat) νmax (cm$^{-1}$): 1744, 1251

EXAMPLE 28

Synthesis of diphenylmethyl 2-O-t-butyldimethylsilyl-3-O-benzyl-4,5-O-isopropylidene-D-xylosate (21b, R"=—CH$_2$C$_6$H$_5$, R$_5$=TBDMS)

Starting from 2.72 g of compound (20b) and following the procedure as described in Example 27, the title compound was obtained.

Yield: 3.10 g (91.5%)

$^1$H-NMR(CDCl$_3$) δ: 0.00 (6H, s), 0.92 (9H, s), 1.38 (3H, s), 1.48 (3H, s), 3.71 (1H, dd, J=4.8, 7.3), 3.85 (1H, t, J=7.8), 4.04–4.26 (2H, m), 4.51 (1H, d, J=4.8), 4.85 (2H, dd, J=12.0, 24.5), 7.01 (1H, s), 7.32–7.47 (15H, m).

EXAMPLE 29

Synthesis of diphenylmethyl 2-O-t-butyldimethylsilyl-3-O-(4-fluorobenzyl)-4,5-O-isopropylidene-D-xylosate (21c,

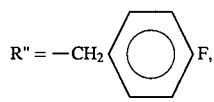

R$_5$=TBDMS)

Starting from 2.8 g of compound (20c) and following the procedure as described in Example 27, the title compound was obtained.

Yield: 3.0 g (88%)

$^1$H-NMR(CDCl$_3$) δ: 0.08 (6H, s), 0.91 (9H, s), 1.37 (3H, s), 1.47(3H, s), 3.66–3.72 (1H, dd, J=4.67, 7.33), 3.79–3.86 (1H, t), 4.03–4.10(1H, m), 4.18–4.29 (1H, m), 4.48 (1H, d, J=4.58), 4.66–4.86 (2H, dd, J=11.73, 28.04), 6.98–7.06 (3H, m), 7.30–7.39 (12H, m).

EXAMPLE 30

Synthesis of diphenylmethyl 2-O-t-butyldimethylsilyl-3-O-(4-methoxybenzyl)-4,5-O-isopropylidene-D-xylosate (21d,

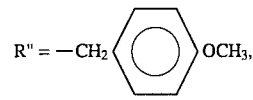

R$_5$=TBDMS)

Starting from 12.85 g of compound (20d) and following the procedure as described in Example 27, the title compound was obtained.

Yield: 11.11 g (70.2%)

$^1$H-NMR(CDCl$_3$) δ: 0.00 (6H, s), 0.91 (9H, s), 1.38 (3H, s), 1.48 (3H, s), 3.68(1H, dd, J=4.5, 7.4), 3.82 (1H, dd, J=7.5, 8.2), 3.94 (3H, s), 4.07 (1H, dd, J=6.2, 8.4), 4.24 (1H, dd, J=7.3, 13.7), 4.47 (1H, d, J=4.4), 4.62–4.80 (2H, m), 6.85 (1H, d, J=8.4), 7.00 (1H, s), 7.25–7.45 (12H, m), 7.61 (1H, d, J=2.1).

EXAMPLE 31

Synthesis of diphenylmethyl 2-O-t-butyldimethylsilyl-3-O-cyclopropylmethyl-4,5-O-isopropylidene-D-xylosate (21e,

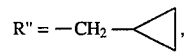

R$_5$=TBDMS

Starting from 7.45 g of compound (20e) and following the procedure as described in Example 27, the title compound was obtained.

Yield: 8.68 g (91.9%)

$[\alpha]_D^{24}$=+1° (C 2.0, CHCl$_3$)

$^1$H-NMR (CDCl$_3$) δ: 0.00 (3H, s), 0.03(3H, s), 0.13–0.17 (2H, m), 0.42–0.48 (2H, m), 0.91 (9H, s), 0.89–0.95 (1H, m), 1.28 (3H, s), 1.38(3H, s), 3.48(2H, d, J=6.8), 3.53–3.59 (1a, m), 3.95–4.15 (2H, m), 4.44 (1H, d, J=4.8), 6.94 (1H, s), 7.23–7.43 (10H, m).

EXAMPLE 32

Synthesis of diphenylmethyl 2-O-t-butyldimethylsilyl-3-O-methyl-D-xylosate (22a, R"=—CH$_3$, R$_5$=TBDMS)

Compound (21a), obtained in example 27 (2.68 g), was dissolved in acetonitrile (238 ml) and 0.015N-hydrochloric acid acetonitrile solution was added. The mixture was stirred at room temperature for 3 hours and quenched by sodium hydrogencarbonate solution (150 mg/2 ml). Solid was filtered off by filtration and the residue, obtained after evaporation, was purified by silica gel column chromatography. The title compound was obtained as solids.

Yield: 1.75 g (71.0%)

m.p.: 79°–80.5° C.

$[\alpha]_D^{24}$=+23.2° (C 0.43, CHCl$_3$)

$^1$H-NMR(CDCl$_3$) δ: 0.00 (9H, s), 0.87 (6H, s), 1.96 (1H, t, J=5.8), 2.56 (1H, d, J=4.8), 3.44 (3H, s), 3.44–3.53 (1H, m), 3.62–3.67 (2H, m) 4.52 (1H, d, J=5.2), 6.97 (1H, s), 7.30–7.36 (10H, m)

IR (Nujol) νmax (cm$^{-1}$): 3405, 1761, 1138

EXAMPLE 33

Synthesis of diphenylmethyl 3-O-benzyl-2-O-t-bytyldimethylsilyl-D-xylosate (22b, R"=—CH$_2$C$_6$H$_5$, R$_5$=TBDMS)

Starting from 3.10 g of compound (21b) by following the procedure as described in Example 32, the title compound was obtained.

Yield: 2.55 g (88.5%)

$^1$H-NMR(CDCl$_3$) δ: 0.00 (6H, s), 0.88 (9H, s), 1.98 (1H, t, J=5.8), 2.55 (1H, d, J=4.9), 3.57–3.74 (4H, m), 4.52–4.58 (2H, m), 4.77 (1H, d, J=11.2), 6.98 (1H, s,), 7.27–7.40 (15H, m).

EXAMPLE 34

Synthesis of diphenylmethyl 2-O-t-butyldimethylsilyl-3-O-(4-fluorobenzyl)-D-xylosate (22c,

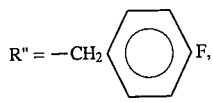

R$_5$=TBDMS)

Starting from 3.0 g of compound (21c) and following the procedure as described in Example 32, the title compound was obtained.

Yield: 1.6 g (57%)

$^1$H-NMR(CDCl$_3$) δ: 0.00 (6H, s), 0.87 (9H, s), 1.89–1.96 (1H, t, J=6.28), 2.52 (1H, d, J=4.81), 3.59–3.62 (2H, m), 3.67–3.76(2H, m), 4.47–4.55 (2H, m), 4.68 (1H, d, J=11.27), 6.93–7.02 (3H, m), 7.17–7.36 (12H, m).

EXAMPLE 35

Synthesis of diphenylmethyl 2-O-t-butyldimethylsilyl-3-O-(4-methoxybenzyl)-D-xylosate (22d,

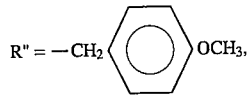

R$_5$=TBDMS)

Starting from 10.73 g of compound (21d) and following the procedure as described in Example 32, the title compound was obtained.

Yield: 7.49 g (74.7%)

[α]$_D^{22}$=−5° (C 2.0 CHCl$_3$)

$^1$H-NMR(CDCl$_3$) δ: 0.00 (6H, s), 0.88 (9H, s), 2.22 (1H, t, J=5.5), 2.67 (1H, d, J=4.8), 3.59–3.69 (2H, m), 3.71–3.73 (2H, m), 3.87 (3H, s), 4.43–4.65 (3H, m), 6.80 (1H, d, J=8.4), 6.97 (1H, s), 7.15–7.47 (12H, m).

EXAMPLE 36

Synthesis of diphenylmethyl 2-O-t-butyldimethylsilyl-3--O-cyclopropylmethyl-D-xylosate (22e,

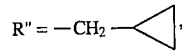

R$_5$=TBDMS)

Starting from 8.09 g of compound (21e) and following the procedure as described in Example 32, the title compound was obtained.

Yield: 6.73 g (89.9%)

$^1$H-NMR(CDCl$_3$) δ: 0.00 (3H, s), 0.02 (3H, s), 0.11–0.14 (2H, m), 0.46–0.51 (2H, m), 0.86 (9H, s), 0.88–1.08 (1H, m), 2.18 (1H, t, J=5.4), 2.68 (1H, d, J=4.6), 3.24–3.30 (1H, m), 3.50–4.65 (5H, m), 4.53 (1H, d, J=6.0), 6.96 (1H, s), 7.25–7.41 (10H, m).

EXAMPLE 37

Synthesis of diphenylmethyl 2-O-t-butyldimethylsilyl-3-O-methyl-5-O-tosyl-D-xylosate (23a, R"=—CH$_3$, R$_4$=Ts, R$_5$=TBDMS)

Compound (22a), obtained in Example 32 (1.74 g), was dissolved in pyridine (20 ml) and p-toluenesulfonyl chloride (1.01 g) was added portionwise at −10° C. The reaction mixture was stirred at room temperature for 24 hours under dried atmosphere. Pyridine was removed by evaporation and the residue was washed successively with 1N-hydrochloric acid, water, saturated sodium hydrogencarbonate solution and brine, and then dried over magnesium sulfate. The residue, obtained after evaporation, was purified by silica gel column chromatography and the title compound was obtained as an oil.

Yield: 1.56 g (67.1%)

[α]$_D^{23}$=+20.3° (C 0.39, CHCl$_3$)

$^1$H-NMR(CDCl$_3$) δ: 0.00 (9H, s), 0.84 (6H, s), 2.44 (3H, s), 2.54 (1H, d, J=5.6), 3.34 (3H, s), 3.54 (1H, dd, J=3.2, 5.3), 3.90–4.14 (2H, m), 4.49 (1H, d, J=5.2), 6.94 (1H, s), 7.29–7.33 (12H, m), 7.77 (1H, d, J=8.3).

IR (Neat) νmax (cm$^{-1}$): 3525, 1735

EXAMPLE 38

Synthesis of diphenylmethyl 3-O-benzyl-2-O-t-butyldimethylsilyl-5-O-tosyl-D-xylosate (23b, R"=—CH$_2$C$_6$H$_5$, R$_4$=Ts, R$_5$=TBDMS)

Starting from 2.05 g of compound (22b) and following the procedure as described in Example 37, the title compound was obtained.

Yield: 2.50 g (89.9%)

$^1$H-NMR(CDCl$_3$) δ: 0.00 (3H, s), 0.02 (3H, s), 0.90 (9H, s), 2.45 (3H, s), 2.64 (1H, d, J=5.7), 3.78–3.82 (1H, m), 3.99–4.10 (3H, m), 4.47–4.59 (2H, m), 4.73 (1H, d, J=11.3), 7.00 (1H, s), 7.22–7.39 (12H, m), 7.79 (2H, d, J=8.3).

EXAMPLE 39

Synthesis of diphenylmethyl 2-O-t-butyldimethylsilyl-3-O-(4-fluorobenzyl)-5-O-tosyl-D-xylosate (23c,

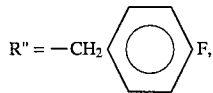

R$_4$=Ts, R$_5$=TBDMS)

Starting from 1.6 g of compound (22c) and following the procedure as described in Example 37, the title compound was obtained.

Yield: 1.7 g (86%)

$^1$H-NMR(CDCl$_3$) δ: 0.00 (6H, s), 0.83 (9H, s), 2.42 (3H, s), 2.51 (1H, s, br), 3.71–3.75 (1H, m), 3.92–3.96 (3H, m), 4.39 (1H, d, J=11.10), 4.50 (1H, d, J=5.21), 4.60 (1H, d, J=11.12), 6.89–7.10 (3H, m), 7.12–7.17 (2H, m), 7.24–7.32 (12H, m), 7.13 (2H, d, J=8.28).

EXAMPLE 40

Synthesis of diphenylmethyl 2-O-t-butyldimethylsilyl-3-O-(4-methoxybenzyl)-5-O-tosyl-D-xylosate (23d,

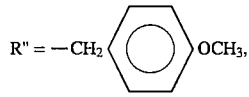

R$_4$=Ts, R$_5$=TBDMS)

Starting from 6.00 g of compound (22d) and following the procedure as described in Example 37, the title compound was obtained.

Yield: 6.15 g (80.7%)

$[α]_D^{22}$=+6° (C 2.0, CHCl$_3$)

$^1$H-NMR(CDCl$_3$) δ: 0.00 (6H, s), 0.89 (9H, s), 2.48 (3H, s), 2.56 (1H, d, J=5.5), 3.76–3.80 (1H, m), 3.94 (3H, s), 3.96–4.07 (3H, m), 4.36–4.63(3H, m), 6.85 (1H, d, J=8.4), 7.00 (1H, s), 7.15–7.74 (12H, m), 7.8 (2H, d, J=8.3).

EXAMPLE 41

Synthesis of diphenylmethyl 2-O-t-butyldimethylsilyl-3-O-cyclopropylmethyl-5-O-tosyl-D-xylosate (23e,

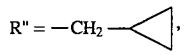

R$_4$=Ts, R$_5$=TBDMS)

Starting from 6.20 g of compound (22e) and following the procedure as described in Example 37, the title compound was obtained.

Yield: 6.70 g (82.7%)

$[α]_D^{22}$=+10° (C 0.2, CHCl$_3$)

$^1$H-NMR(CDCl$_3$) δ: 0.00 (3H, s), 0.34 (3H, s), 0.06–0.09 (2H, m), 0.42–0.49 (2H, m), 0.86 (9H, s), 0.81–0.99 (1H, m), 2.45 (3H, s), 2.62 (1H, d, J=6.0), 3.12–3.21 (1H, m), 3.43–3.52 (1H, m), 3.62–3.67 (1H, m), 3.85–3.99(1H, m), 4.09–4.19 (1H, m), 4.50 (1H, d, J=5.4), 6.96 (1H, s), 7.28–7.41 (12H, m), 7.78 (2H, d, J=8.4).

EXAMPLE 42

Synthesis of diphenylmethyl 2-O-t-butyldimethylsilyl-3-O-methyl-4-O-(3'-oxo-2'-azacyclobutyl)-5-O-tosyl-D-xylosate (24a, R"=—CH$_3$, R$_4$=Ts, R$_5$=TBDMS)

A mixture of compound (23a), obtained in example 37 (1.55 g), 4-acetoxyazetidin-2-one (651 mg), triethylamine (702 μl) and palladium (II) acetate (112 mg) in benzene (50 ml) was stirred at room temperature under nitrogen atmosphere for 24 hours. Solid stuff was removed by filtration and the filtrate was washed with water and brine and dried over magnesium sulfate. The residue, obtained by evaporation, was purified by silica gel column chromatography and the title compound was obtained as an oil.

Yield: 920 mg (53.4%)

$^1$H-NMR(CDCl$_3$) δ: 0.04 (9H, s), 0.88 (6H, s), 2.50 (3H, s), 2.60–3.04 (2H, m), 3.35 (3H, s), 3.46–3.57 (1H, m), 3.17–3.87 (1H, m), 4.10–4.37 (2H, m), 4.48–4.51 (1H, m), 4.85–4.92 (1H, m), 6.97 (1H, s), 7.30–7.38 (12H, m), 7.80 (2H, d, J=8.2).

IR (Neat ) νmax (cm$^{-1}$): 3360, 1769

EXAMPLE 43

Synthesis of diphenylmethyl 3-O-benzyl-2-O-t-butyldimethylsilyl-4-O-(3'-oxo-2'-azacyclobutyl)-5-O-tosyl-D-xylosate (24b, R"=—CH$_2$C$_6$H$_5$, R$_4$=Ts, R$_5$=TBDMS)

Starting from 1.96 g of compound (23b) and following the procedure as described in Example 42, the title compound was obtained.

Yield: 1.45 g (67.5%)

$^1$H-NMR(CDCl$_3$) δ: 0.00 (3H, s), 0.02 (3H, s), 0.88 (9H, s), 2.47 (3H, s), 2.56–3.01 (2H, m), 3.70–3.83 (2H, m), 4.03–4.32 (2H, m), 4.44–4.71 (3H, m), 4.83–4.85 (1H, m), 6.23–6.48 (1H, m), 6.97 (1H, s), 7.20–7.36 (12H, m), 7.77 (2H, d, J=8.4).

EXAMPLE 44

Synthesis of diphenylmethyl 2-O-t-butyldimethylsilyl-3-O-(4-fluorobenzyl)-4-O-(3'-oxo-2'-aza cyclobutyl)-5-O-tosyl-D-xylosate (24c,

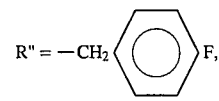

R$_4$=Ts, R$_5$=TBDMS)

Starting from 1.7 g of compound (23c) and following the procedure as described in Example 42, the title compound was obtained.

Yield: 1.1 g (59%)

$^1$H-NMR(CDCl$_3$) δ: 0.00 (6H, s), 0.83 (9H, s), 2.45 (3H, d, J=4.45), 2.52–3.00 (2H, m), 3.6–3.78 (2H, m), 3.93–4.25 (3H, m), 4.30–4.80 (3H, m), 6.03 (1H, s), 6.90–7.02 (3H, m), 7.08–7.17 (2H, m), 7.23–7.37 (12H, m), 7.36–7.78 (2H, m).

EXAMPLE 45

Synthesis of diphenylmethyl 2-O-t-butyldimethylsilyl-3-O-(4-methoxybenzyl)-4-O-(3'-oxo-2'-azacyclobutyl)-5-O-tosyl-D-xylosate (24d,

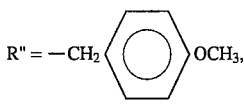

$R_4$=Ts, $R_5$=TBDMS)

Starting from 7.15 g of compound (23d) and following the procedure as described in Example 42, the title compound was obtained.

Yield: 5.02 g (64.1%)

$[\alpha]_D^{22}$=+5.5° (C 2.0, CHCl$_3$)

$^1$H-NMR(CDCl$_3$) δ: 0.02 (6H, s), 0.89 (9H, s), 2.51 (3H, s), 2.53–3.07 (2H, m), 3.66–3.84 (2H, m), 3.96 (3H, s), 3.99–4.64 (5H, m), 4.87–4.87 (1H, m), 6.11–6.33 (1H, m), 6.84–6.90 (1H, m), 6.97 (1H, d, J=2.0), 7.14–7.46 (15H, m), 7.76–7.81 (2H, dd, J=2.0, 8.4).

EXAMPLE 46

Synthesis of diphenylmethyl 2-O-t-butyldimethylsilyl-3-O-cyclopropylmethyl-4-O-(3'-oxo-2'-azacyclobutyl)-5-O-tosyl-D-xylosate (24e,

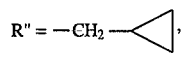

$R_4$=Ts, $R_5$=TBDMS)

Starting from 6.88 g of compound (23e) and following the procedure as described in Example 42, the title compound was obtained.

Yield: 5.35 g (70.4%)

$[\alpha]_D^{22}$=+9° (C 2.0, CHCl$_3$)

$^1$H-NMR(CDCl$_3$) δ: 0.00 (3H, m), 0.04 (3H, m), 0.07–0.15 (2H, m), 0.45–0.56 (2H, m), 0.89 (9H, s), 2.51 (3H, s), 2.59–2.76 (1H, m), 2.92–3.03 (1H, m), 3.17–3.28 (1H, m), 3.43–3.68 (2H, m), 3.80–3.88(1H, m), 4.14–4.23 (1H, m), 4.33–4.51 (2H, m), 4.83–4.92 (1H, m), 6.29–6.34 (1H, m), 7.32–7.46 (12H, m), 7.82 (2H, d, J=8.3).

EXAMPLE 47

Synthesis of diphenylmethyl 2-O-t-butyldimethylsilyl-3-O-methyl-4-O-(3'-oxo-2'-azacyclobutyl)-5-iodo-D-xylosate (25a, R"=—CH$_3$, $R_5$=TBDMS, $R_6$=I)

A mixture of compound (24a), obtained in example 42 (400 mg) and sodium iodide (470 mg) in acetone (25 ml) was refluxed for 24 hours. Solvent was removed in vacuo and the residue was dissolved in ethyl acetate. This solution was washed with 5% sodium thiosulfate solution, water and brine and dried over magnesium sulfate. The residue, obtained after evaporation, was purified by silica gel column chromatography and the title compound was obtained as an oil.

Yield: 250 mg (62.0%)

$^1$H-NMR(CDCl$_3$) δ: 0.00 (9H, s), 0.88 (6H, s), 2.74–3.16 (4H, m), 3.48 (3H, s), 3.62–3.65 (1H, m), 4.45–4.48 (1H, m), 4.79–4.88 (1H, m), 6.94 (1H, s), 7.26–7.36 (10H, m).

IR (Neat) vmax (cm$^{-1}$): 3295, 1769

EXAMPLE 48

Synthesis of diphenylmethyl 3-O-benzyl-2-O-t-butyldimethylsilyl-5-bromo-4-O-(3'-oxo-2'-azacyclobutyl)-D-xylosate (25b, R"=—CH$_2$C$_6$H$_5$, $R_5$=TBDMS, $R_6$=Br)

Starting from 1.45 g of compound (24b) and following the procedure as described in Example 47, the title compound was obtained.

Yield: 1.06 g (82.9%)

$^1$H-NMR(CDCl$_3$) δ: 0.00 (3H, s), 0.02 (3H, s), 0.89 (9H, s), 2.52–3.01 (2H, m), 3.32–3.87 (4H, m), 4.52–4.63 (2H, m), 4.74–4.85 (2H, m), 6.11–6.37 (1H, m), 6.94 (1H, s), 7.26–7.39 (10H, m).

EXAMPLE 49

Synthesis of diphenylmethyl 2-O-t-butyldimethylsilyl-3-O-(4-fluorobenzyl)-4-O-(3'-oxo-2'-azacyclobutyl) -5-bromo-D-xylosate (25c,

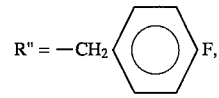

$R_5$=TBDMS, $R_6$=Br)

A mixture of compound (24c) (1.1 g) and LiBr (0.76 g) in HMPA (10 ml) was heated at 65°–70° C. for 1 hour. After cooling the reaction mixture, it was extracted with ethyl acetate. The organic extract was washed with water and brine, dried over sodium sulfate and concentrated under vacuum. The crude residue was purified on silica gel using ethyl acetate:hexane (1:3) as eluant.

Yield: 0.8 g (82%)

$^1$H-NMR(CDCl$_3$) δ: 0.00 (6H, s), 0.87 (9H, s), 2.53–3.05 (2H, m), 3.25–3.39 (1H, m), 3.50–3.83 (3H, m), 4.46–4.84 (4H, m), 6.05 (1H, br, d), 6.91–7.04 (3H, m), 7.20–7.36 (12H, m).

EXAMPLE 50

Synthesis of diphenylmethyl 2-O-t-butyldimethylsilyl-3-O-(4-methoxybenzyl)-4-O-(3'-oxo-2'-azacyclobutyl)-5-bromo-D-xylosate (25d,

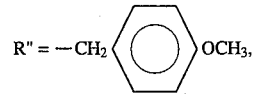

$R_5$=TBDMS, $R_6$=Br)

Starting from compound (24d) (5.0 g) and LiBr (3.44 g) in HMPA (120 ml) and following the procedure as described in Example 49, the title compound was obtained.

Yield: 3.89 g (88.0%)

[α]$_D^{22}$=−4° (C 2.0, CHCl$_3$)

$^1$H-NMR(CDCl$_3$) δ: 0.02 (6H, s), 0.88 (9H, s), 2.53–3.05 (2H, m), 3.28–3.85 (4H, m), 3.89 (3H, s), 4.47–4.86 (4H, m), 6.19–6.41 (1H, m), 6.83 (1H, dd, J=2.6, 8.4), 6.93 (1H, s), 7.18–7.52 (13H, m).

EXAMPLE 51

Synthesis of diphenylmethyl 2-O-t-butyldimethylsilyl-3-O-cyclopropylmethyl-4-O-(3'-oxo-2'-azacyclobutyl)-5-bromo-D-xylosate (25e,

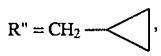

R$_5$=TBDMS R$_6$=Br)

Starting from compound (24e) (5.35 g) and LiBr (4.0 g) in HMPA (125 ml) and following the procedure as described above, the title compound was obtained.

Yield: 4.21 g (90%)

[α]$_D^{22}$=+5° (C 2.0, CHCl$_3$)

$^1$H-NMR(CDCl$_3$) δ: 0.00 (3H, m), 0.5 (3H, m), 0.11–0.20 (3H, m), 0.40–0.54 (2H, m), 0.83 (9H, s), 0.87–1.13 (1H, m), 2.57–3.03 (2H, m), 3.23–3.84 (6H, m), 4.44–4.47 (1H, m), 4.74–4.87 (1H, m), 6.27–6.32(1H, m), 6.88 (1H, s), 7.25–7.39 (10H, m).

EXAMPLE 52

Syntheses of diphenylmethyl 3-[(3'R,5'S)-7'-oxo-1'-aza-4,-oxabicyclo[3.2.0]hept-3'-yl]-2(R)-t-butyldimethylsilyloxy-3(S)-methoxypropionate (26a, R"=—CH$_3$, R$_5$=TBDMS) and its cis (3'R, 5'R) isomer (27a, R"=—CH$_3$, R$_5$=TBDMS)

To a solution of compound (25a), obtained in Example 47 (720 mg), in dimethyl sulfoxide (10 ml), cesium carbonate (734 mg) was added and stirred at room temperature for 1 hour. The reaction mixture was diluted with ethyl acetate and washed with water and brine, and then dried over magnesium sulfate. After removal of solvent, the residue was purified by silica gel column chromatography and the title compounds were obtained as an oil individually. compound (26a) (upper)

Yield: 250 mg (43.2%)

[α]$_D^{23}$=−34.7° (C 0.35, CDCl$_3$)

$^1$H-NMR(CDCl$_3$) δ: 0.00 (9H, s), 0.87 (6H, s), 2.60 (1H, d, J=16.1), 2.84 (1H, dd, J=6.2, 11.2), 3.08 (1H, dd, J=2.3, 16.1), 3.30 (1H, dd, J=3.6, 5.9), 3.52 (3H, s), 3.83 (1H, dd, J=7.1, 11.2), 4.26–4.35.(1H, m), 4.51 (1H, d, J=5.9), 5.12 (1H, d, J=2.5), 6.97 (1H, s), 7.28–7.36 (10H, m).

IR (Neat) vmax (cm$^{-1}$): 1785, 1744, 1130 compound (27a) (lower)

Yield: 260 mg (45%)

[α]$_D^{23}$=+32.5° (C 0.31, CDCl$_3$)

$^1$H-NMR(CDCl$_3$) δ: 0.00 (9H, s), 0.86 (6H, s), 2.78 (1H, d, J=16.0), 2.95–3.12 (2H, m), 3.33 (1H, dd, J=4.1, 6.1), 3.49 (1H, dd, J=5.3, 11.2), 4.21–4.29 (1H, m), 4.47 (1H, d, J=6.2), 5.10 (1H, d, J=2.4), 6.96 (1H, s), 7.79–7.37 (10H, m).

IR (Neat) vmax (cm$^{-1}$): 1785, 1744, 1136

EXAMPLE 53

Syntheses of diphenylmethyl 3-[(3'R,5'S)-7'-oxo-1'-aza-4'-oxabicyclo[3.2.0]hept-3'-yl]-3(S)-benzyloxy-2(R)-t-butyldimethylsilyloxypropionate (26b, R"=—CH$_2$C$_6$H$_5$, R$_5$=TBDMS) and its cis(3'R, 5'R) isomer (27b, R"=—CH$_2$C$_6$H$_5$, R$_5$=TBDMS)

Starting from 7.89 g of compound (25b) and following the procedure as described in Example 52, the title compounds were obtained.

compound (26b) (upper)

Yield: 3.42 g (49.4%)

$^1$H-NMR(CDCl$_3$) δ: 0.00 (6H, s), 0.88 (9H, s), 2.57 (1H, d, J=16.1), 2.76 (1H, dd, J=5.4, 11.1), 3.02 (1H, dd, J=2.5, 16.1), 3.49 (1H, dd, J=3.0, 6.08), 3.76 (1H, dd, J=7.3, 11.1), 4.37–4.45 (1H, m), 4.57–4.66 (2H, m), 4.91 (1H, d, J=11.7), 5.06 (1H, d, J=2.3), 7.00 (1H, s), 7.24–7.39 (15H, m).

compound (27b) (lower)

Yield: 1.2 g (17.3%)

$^1$H-NMR(CDCl$_3$) δ: 2.72 (1H, d, J=15.92), 2.96–3.11 (2H, m), 3.56–3.64 (2H, m), 4.37–4.46 (1H, m), 4.54 (1H, d, J=5.37), 4.7 (2H, d, J=6.37), 5.06 (1H, d, J=2.21) 7.04 (1H, s ), 7.30–7.41 (15H, m).

EXAMPLE 54

Syntheses of diphenylmethyl 3-[(3'R,5'S)-7'-oxo-1'-aza-4'-oxabicyclo[3.2.0]hept-3'-yl]-2(R)-t-butyldimethylsilyloxy-3(S)-(4"-fluorobenzyl)oxypropionate (26c,

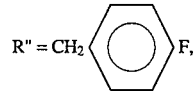

R$_5$=TBDMS) and its cis(3'R, 5'R) isomer (27c,

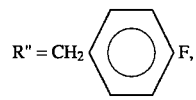

R$_5$=TBDMS)

A mixture of compound (25c ) (800 mg ) and cesium carbonate (420 mg) in DMSO (30 ml) was stirred at room temperature for 6 hours. The resulting mixture was diluted with ethyl acetate, washed with water and brine, dried over sodium sulfate and concentrated under vacuum. The residue was purified on silica gel using ethyl acetate:hexane (1:6) as eluant to give a trans compound (26c) and later fraction to give a cis compound (27c).

compound (26c) (upper)

Yield: 0.27 g (38%)

$^1$H-NMR(CDCl$_3$) δ: 0.00 (6H, s), 0.85 (9H, s), 2.60 (1H, d, J=16.60), 2.70–2.80 (1H, dd, J=6.55, 11.40), 3.00–3.13 (1H, dd, J=2.45.11.25), 3.47–3.54 (1H, dd, J=2.70, 5.25), 3.74–3.85 (1H, dd, J=6.90, 11.45), 4.36–4.46 (1H, m), 4.54–4.65 (2H, m), 4.85 (1H, d, J=11.25), 5.08 (1H, d, J=2.52), 6.97–7.09 (3H, m), 7.22–7.39 (12H, m).

EXAMPLE 55

Syntheses of diphenylmethyl 3-[(3'R,5'S)-7'-oxo-1'-aza-4'-oxabicyclo[3.2.0]hept-3'-yl]-2(R)-t-butyldimethylsilyloxy-3(S)-(4"-methoxybenzyl)oxypropionate (26d,

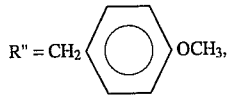

$R_5$=TBDMS) and its cis(3'R, 5'R) isomer (27d,

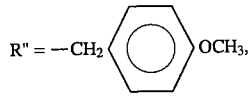

$R_5$=TBDMS)

Starting from 3.75 g of compound (25d) and following the procedure as described in Example 54, the title compounds were obtained.

compound (26d) (upper)
Yield: 1.21 g (36.6%)
$[\alpha]_D^{22}$=−29° (C 2.0, CHCl$_3$)
$^1$H-NMR(CDCl$_3$) δ: 0.01 (6H, s), 0.88 (9H, s), 2.56–2.79 (2H, m), 3.02–3.11 (1H, m), 3.46–3.50 (1H, m), 3.73–3.83 (1H, m), 3.91 (3H, s), 4.35–4.43 (1H, m), 4.54 (2H, dd, J=3.5, 9.5), 4.77 (1H, d, J=11.5), 5.08 (1H, d, J=2.4), 6.85 (1H, d, J=8.3), 6.99 (1H, s), 7.19–7.51 (12H, m).

compound (27d) (lower)
Yield: 1.0 g (30.2%)
$^1$H-NMR(CDCl$_3$) δ: 0.00 (6H, s), 0.85 (9H, s), 2.68 (1H, d, J=16.1), 2.92–2.96 (2H, m), 3.37–3.55 (2H, m), 3.88 (3H, s), 4.31–4.70 (4H, m), 5.03 (1H, d, J=2.0), 6.83 (1H, d, J=8.3), 6.94 (1H, s), 7.23–7.37 (12H, m), 7.54 (1H, d, J=2.0).

EXAMPLE 56

Syntheses of diphenylmethyl 3-[(3'R,5'S)- 7'-oxo-1'-aza-4'-oxabicyclo[3.2.0]hept-3'-yl]-2(R)-t-butyldimethylsilyloxy-3(S)-cyclopropyl-methyloxypropionate (26e,

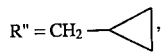

$R_5$=TBDMS) and its cis(3'R, 5'R) isomer (27e,

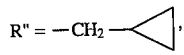

$R_5$=TBDMS)

Starting from 4.07 g of compound (25e) and following the procedure as described in Example 54, the title compounds were obtained.

compound (26e) (upper)
Yield: 1.02 g (29.5%)
$[\alpha]_D^{21}$=−50° (C 2.0, CHCl$_3$)
$^1$H-NMR(CDCl$_3$) δ: 0.00 (3H, s), 0.04(3H, s), 0.17–0.19 (2H, m), 0.45–0.53 (2H, m), 0.85 (9H, s), 0.90–1.16 (1H, m), 2.56 (1H, d, J=16.1), 2.85–3.07 (2H, m), 3.28–3.50 (2H, m), 3.65–3.84 (2H, m), 4.29–4.37 (1H, m), 4.49 (1H, d, J=6.2), 5.09 (1H, d, J=2.4), 6.97 (1H, s), 7.25–7.41 (10H, m).

compound (27e) (lower)
Yield: 0.73 g (21.0%)
$[\alpha]_D^{21}$=+17° (C 2.0, CHCl$_3$)
$^1$H-NMR(CDCl$_3$) δ: 0.00 (3H, m), 0.02 (3H, m), 0.15–0.27 (2H, m), 0.46–0.53 (2H, m), 0.86 (9H, s), 2.74 (1H, d, J=15.9), 2.98–3.06 (2H, m), 3.42–3.55 (3H, m), 3.70 (1H, dd, J=5.8, 11.0), 4.30–4.39 (1H, m), 4.49 (1H, d, J=4.3), 5.04 (1H, d, J=2.8), 6.97 (1H, s), 7.27–7.44 (10H, m).

EXAMPLE 57

Synthesis of diphenylmethyl 3-[(3'R,5'S)-7'-oxo-1'-aza-4'-oxabicyclo[3.2.0]hept-3'-yl]-2(R)-hydroxy-3(S)-methoxypropionate (28a, R"=—CH$_3$)

To a solution of compound (26a), obtained in Example 52 (250 mg), in tetrahydrofuran (10 ml), and acetic acid (23 μl), 1N-tetrabutylammonium fluoride in tetrahydrofuran (588 μl) was added dropwise and the reaction mixture was stirred at room temperature for 3 hours. The reaction mixture was directly purified by silica gel column chromatography and the title compound was obtained as solids.

Yield: 170 mg (87.3%)
m.p.: 104.5°–106.5° C.
$[\alpha]_D^{22}$=−28.9° (C 0.35, CDCl$_3$)
$^1$H-NMR(CDCl$_3$) δ: 2.77 (1H, d, J=16.1), 2.90–3.21 (3H, m), 3.27 (1H, dd, J=2.6, 5.6), 3.97 (1H, dd, J=6.7, 11.5), 4.37 (1H, dd, J=2.5, 6.9), 4.55 (1H, dd, J=6.9, 12.6), 5.20 (1H, d, J=2.6), 7.04 (1H, s), 7.32–7.36 (10H, m).
IR (Nujol) νmax (cm$^{-1}$): 3480, 1803, 1740

EXAMPLE 58

Synthesis of diphenylmethyl 3-[(3'R,5'S)-7'-oxo-1'-aza-4'-oxabicyclo[3.2.0]hept-3'-yl]-2(R)-hydroxy-3(S)-benzyloxypropionate (28b, R"=—CH$_2$C$_6$H$_5$)

Starting from 3.42 g of compound (26b) and following the procedure as described in Example 57, the title compound was obtained.

Yield: 1.70 g (62%)
$^1$H-NMR(CDCl$_3$) δ: 2.70 (1H, d, J=16.31), 2.91–3.00 (1H, dd, J=6.44, 11.36), 3.05–3.15 (2H, m), 3.77–3.81 (1H, m), 3.86–3.96 (1H, dd, J=7.00, 11.36), 4.41–4.47 (3H, m), 4.54–4.63 (1H, m), 5.11 (1H, d, J=2.5), 7.02 (1H, s), 7.09–7.32 (15H, m).

EXAMPLE 59

Synthesis of diphenylmethyl 3-[(3'R,5'S)-7'-oxo-1'-aza-4'-oxabicyclo[3.2.0]hept-3'-yl]-2(R)-hydroxy-3(S)-(4"-fluorobenzyl)oxypropionate (28c,

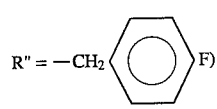

Starting from 270 mg of compound (26c) and following the procedure as described in Example 57, the title compound was obtained.

Yield: 200 mg (91%)

$^1$H-NMR(CDCl$_3$) δ: 2.74 (1H, d, J=16.67), 2.90–2.99 (1H, dd, J=6.58, 11.49), 3.08–3.20 (2H, m), 3.77–3.81 (1H, dd, J=2.72, 5.28), 3.90–4.00 (1H, dd, J=6.91, 11.43), 4.31–4.59 (4H, m), 5.16 (1H, d, J=2.56), 6.88–7.08 (3H, m), 7.25–7.32 (12H, m).

EXAMPLE 60

Synthesis of diphenylmethyl 3-[(3'R,5'S)-7'-oxo-1'-aza-4'-oxabicyclo[3.2.0]hept-3'-yl]-2(R)-hydroxy-3(S)-(4"-methoxybenzyl)oxypropionate (28d,

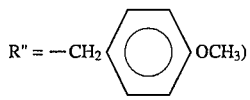

Starting from 1.2 g of compound (26d) and following the procedure as described in Example 57, the title compound was obtained.

Yield: 880 mg (90.0%)

$[α]_D^{22}$=-23° (C 2.0, CHCl$_3$)

$^1$H-NMR(CDCl$_3$) δ: 2.74 (1H, d, J=16.1), 2.93 (1H, dd, J=6.8, 11.5), 3.10–3.20 (2H, m), 3.75–3.79 (1H, m), 3.86 (3H, s), 3.95 (1H, dd, J=6.9, 11.5), 4.27 (1H, d, J=11.2), 4.37–4.44 (2H, m), 4.57 (1H, dd, J=6.8, 12.2), 5.16 (1H, d, J=2.4), 6.75 (1H, d, J=8.4), 6.98 (1H, d, J=2.0), 7.02 (1H, s), 7.26–7.43 (12H, m).

EXAMPLE 61

Synthesis of diphenylmethyl 3-[(3'R,5'S)-7'-oxo-1'-aza-4'-oxabicyclo[3.2.0]hept-3'-yl]-2(R)-hydroxy-3(S)-cyclopropylmethyloxypropionate (28e,

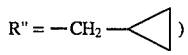

Starting from 1.0 g of compound (26e) and following the procedure as described in Example 57, the title compound was obtained.

Yield: 641 mg (81.4% )

$[α]_D^{22}$=-55° (C 2.0, CHCl$_3$)

$^1$H-NMR(CDCl$_3$) δ: 0.03–0.05 (2H, m), 0.34–0.44 (2H, m), 0.74–0.96 (1H, m), 2.74 (1H, d, J=16.1), 2.96–3.30 (5H, m), 3.69–3.71 (1H, m), 3.95 (1H, dd, J=6.9, 11.4), 4.36 (1H, d, J=2.5), 4.60 (1H, dd, J=6.8, 11.9), 5.19 (1H, d, J=2.5), 7.03 (1H, s), 7.22–7.45 (10H, m).

EXAMPLE 62

Synthesis of diphenylmethyl 3-[(3'R,5'S)-7'-oxo-1'-aza-4'-oxabicyclo[3.2.0]hept-3'-yl]-2(R)-trifluoromethanesulfonyloxy-3(S)-methoxypropionate (29a, R"=—CH$_3$, R$_4$=SO$_2$CF$_3$)

To a solution of compound (28a), obtained in Example 57 (160 mg), pyridine (48 μl) in dichloromethane (10 ml), trifluoromethanesulfonic anhydride (79 μl) was added dropwise at –40° C. and the reaction mixture was stirred for 30 minutes. The reaction mixture was washed with water and brine and dried over magnesium sulfate. The residue, obtained after evaporation, was purified by silica gel column chromatography, and the title compound was obtained as an oil.

Yield: 200 mg (100%)

$[α]_D^{22}$=-31.2° (C 0.38, CDCl$_3$)

$^1$H-NMR(CDCl$_3$) δ: 2.66 (1H, d, J=16.1), 2.89 (1H, dd, J=6.4, 11.7), 3.16 (1H, dd, J=2.0, 15.6), 3.50 (3H, s), 3.56 (1H, dd, J=2.4, 6.8), 3.85 (1H, dd, J=7.3, 11.2), 4.29–4.37 (1H, m), 5.21 (1H, d, J=2.4), 5.38 (1H, d, J=6.4), 7.01 (1H, s), 7.35 (10H, s).

IR (Neat) νmax (cm$^{-1}$): 1703, 1751, 1418, 1209

EXAMPLE 63

Synthesis of diphenylmethyl 3-[(3'R,5'S)-7'-oxo-1'-aza-4'-oxabicyclo[3.2.0]hept-3,-yl]-2(R)-trifluoromethanesulfonyloxy-3(S)-benzyloxypropionate (29b, R"=—CH$_2$C$_6$H$_5$, R$_4$=SO$_2$CF$_3$)

Starting from 1.70 g of compound (28b) and following the procedure as described in Example 62, the title compound was obtained.

Yield: 1.75 g (80.6%)

$^1$H-NMR(CDCl$_3$) δ: 2.56–2.74 (2H, m), 3.04–3.13 (1H, dd, J=2.29, 16.13), 3.67–3.80 (2H, m), 4.30–4.38 (1H, m), 4.47 (1H, d, J=11.29), 4.81 (1H, d, J=11.30), 5.13 (1H, d, J=2.41), 5.44 (1H, d, J=6.32), 7.02 (1H, s), 7.21–7.37 (15H, m).

EXAMPLE 64

Synthesis of diphenylmethyl 3-[(3'R,5'S)-7'-oxo-1'-aza-4'-oxabicyclo[3.2.0]hept-3'-yl]-2(R)-trifluoromethanesulfonyloxy-3(S)-(4"-fluorobenzyl)oxy-propionate (29c,

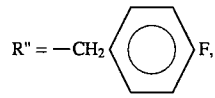

R$_4$=SO$_2$CF$_3$)

Starting from 200 mg of compound (28c) and following the procedure as described in Example 62, the title compound was obtained.

Yield: 200 mg (80%)

$^1$H-NMR(CDCl$_3$) δ: 2.60–2.77 (2H, m), 3.08–3.17 (1H, dd, J=2.46, 11.23), 3.72–3.81 (2H, m), 4.30–4.40 (1H, m), 4.44 (1H, d, J=11.14), 4.75 (1H, d, J=11.22), 5.15 (1H, d, J=2.46), 5.42 (1H, d, J=6.31), 6.96–7.05 (3H, m), 7.17–7.34 (12H, m).

EXAMPLE 65

Synthesis of diphenylmethyl 3-[(3'R,5'S)-7'-oxo-1'-aza-4'-oxabicyclo[3.2.0]hept-3'-yl]-2(R)-trifluoromethanesulfonyloxy-3(S)-(4"-methoxybenzyl)oxy-propionate (29d,

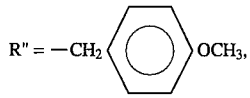

$R_4=SO_2CF_3$)

Starting from 870 mg of compound (28d) and following the procedure as described in Example 62, the title compound was obtained.

Yield: 320 mg (29%)

$[\alpha]_D^{21}=-30°$ (C 2.0, CHCl$_3$)

$^1$H-NMR(CDCl$_3$) δ: 2.59–2.76 (2H, m), 3.12 (1H, dd, J=2.5, 16.2), 3.71–3.80 (2H, m), 3.89 (3H, s), 4.30–4.41 (2H, m), 4.69 (1H, d, J=11.2), 5.15 (1H, d, J=2.4), 5.40–5.43 (1H, d, J=6.2), 6.83 (1H, d, J=8.4), 7.02 (1H, s), 7.13–7.42 (13H, m).

EXAMPLE 66

Synthesis of diphenylmethyl 3-[(3'R,5'S)-7'-oxo-1'-aza-4'-oxabicyclo[3.2.0]hept-3'-yl]-2(R)-trifluoromethanesulfonyloxy-3(S)-cyclopropylmethyloxypropionate (29e,

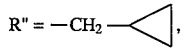

$R_4=SO_2CF_3$)

Starting from 570 mg of compound (28e) and following the procedure as described in Example 62, the title compound was obtained.

Yield: 400 mg (54.1%)

$[\alpha]_D^{22}=-39°$ (C 2.0, CHCl$_3$)

$^1$H-NMR(CDCl$_3$) δ: 0.16–0.21 (2H, m), 0.48–0.56 (2H, m), 0.92–1.07 (1H, m), 2.64 (1H, d, J=16.2), 2.95 (1H, dd, J=5.3, 11.0), 3.14 (1H, dd, J=2.3, 6.2), 3.28 (1H, dd, J=7.1, 10.2), 3.63 (1H, dd, J=6.8, 10.2), 3.70 (1H, dd, J=2.4, 6.8), 3.83 (1H, dd, J=7.3, 11.2), 4.32–4.38 (1H, m), 5.23 (1H, d, J=2.3), 5.39 (1H, d, J=6.7), 7.01 (1H, s), 7.26–7.40 (10H, m).

EXAMPLE 67

Synthesis of diphenylmethyl 3-[(3'R,5'S)-7'-oxo-1'-aza-4'-oxabicyclo[3.2.0]hept-3'-yl]-2(S)-azido-3(R)-methoxypropionate (30a, R"=—CH$_3$)

To a solution of compound (29a), obtained in Example 62 (200 mg), in N,N-dimethylformamide (20ml), sodium azide (78 mg) was added at 5° C. and the mixture was stirred for 1 hour. The reaction mixture was diluted with ethyl acetate, washed with water and brine, and then dried over magnesium sulfate. The residue, obtained after evaporation, was purified by silica gel column chromatography and the title compound was obtained as an oil.

Yield: 140 mg (67.6%)

$[\alpha]_D^{22}=-81.6°$ (C 0.39, CDCl$_3$)

$^1$H-NMR (CDCl$_3$) δ: 2.77 (1H, d, J=16.1), 2.88 (2H, dd, J=6.3, 11.2), 3.22 (1H, dd, J=2.9, 16.6), 3.29 (3H, s), 3.54(1H, dd, J=3.4, 7.3), 3.92 (1H, dd, J=7.0, 11.4), 4.20 (1H, d, J=7.3), 4.46–4.54 (1H, m), 5.31 (1H, d, J=2.5), 6.99 (1H, s), 7.30–7.39 (10H, m).

IR (Neat) vmax (cm$^{-1}$): 2115, 1783, 1742

EXAMPLE 68

Synthesis of diphenylmethyl 3-[(3'R,5'S)-7'-oxo-1'-aza-4'-oxabicyclo[3.2.0]hept-3'-yl]-2(S)-azido-3(R)-benzyloxypropionate (30b, R"=—CH$_2$C$_6$H$_5$)

Starting from 1.75 g of compound (29b) and following the procedure as described in Example 67, the title compound was obtained.

Yield: 1.3 g (90.3%)

$^1$H-NMR(CDCl$_3$) δ: 2.71–2.84 (2H, m), 3.14–3.23 (1H, dd, J=2.34, 16.11), 3.79–3.86 (2H, m), 4.28 (1H, d, J=7.00), 4.40–4.57 (3H, m), 5.29 (1H, d, J=2.55), 6.97 (1H, s), 7.14–7.37 (15H, m).

EXAMPLE 69

Synthesis of diphenylmethyl 3-[(3'R,5'S)-7'-oxo-1'-aza-4'-oxabicyclo[3.2.0]hept-3'-yl)-2(S)-azido-3(R)-(4"-fluorobenzyl)oxypropionate (30c,

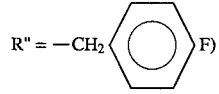

Starting from 200 mg of compound (29c) and following the procedure as described in Example 67, the title compound was obtained.

Yield: 90 mg (54%)

$^1$H-NMR(CDCl$_3$) δ: 2.72–2.86 (2H, m), 3.17–3.28 (1H, dd, J=2.46, 11.23), 3.79–3.93 (3H, m), 4.25 (1H, d, J=7.11), 4.45 (1H, d, J=5.77), 4.5–4.6 (1H, m), 5.28(1H, d, J=2.45), 6.90–7.07 (3H, m), 7.26–7.34 (12H, m).

EXAMPLE 70

Synthesis of diphenylmethyl 3-[(3'R,5'S)-7'-oxo-1'-aza-4'-oxabicyclo[3.2.0]hept-3'-yl)-2(S)-azido-3(R)-(4"-methoxybenzyl)oxypropionate (30d,

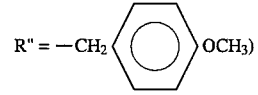

Starting from 320 mg of compound (29d) and following the procedure as described in Example 67, the title compound was obtained.

Yield: 260 mg (97.8%)

$[\alpha]_D^{22}=-56°$ (C 2.0, CHCl$_3$)

$^1$H-NMR(CDCl$_3$) δ: 2.72–2.84 (2H, m), 3.21 (1H, dd, J=2.5, 16.6), 3.75–3.92 (2H, m), 3.88 (3H, s), 4.25 (1H, d, J=7.1), 4.38 (2H, dd, J=11.1, 16.2), 4.50–4.58 (1H, m), 5.29

(1H, d, J=2.3), 6.77 (1H, d, J=8.5), 6.98 (1H, s), 7.05 (1H, dd, J=2.0, 8.4), 7.26–7.35 (12H, m).

IR (Nujol) νmax (cm$^{-1}$): 2110, 1782, 1742

EXAMPLE 71

Synthesis of diphenylmethyl 3-[(3'R,5'S)-7'-oxo-1'-aza-4'-oxabicyclo[3.2.0]hept-3'-yl)-2(S)-azido-3(R)-cyclopropylmethyloxypropionate (30e,

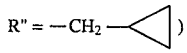

Starting from 400 mg of compound (29e) and following the procedure as described in Example 67, the title compound was obtained.

Yield: 300 mg (92.4%)

$[\alpha]_D^{22}$=−81° (C 2.0, CHCl$_3$)

$^1$H-NMR(CDCl$_3$) δ: 0.00–0.11 (2H, m), 0.38–0.50 (2H, m), 0.74–0.97 (1H, m), 2.76 (1H, d, J=16.3), 2.93 (1H, dd, J=6.0, 11.4), 3.15–3.27 (3H, m), 3.65–3.70 (1H, m), 3.92 (1H, dd, J=7.1, 11.3), 4.22 (1H, d, J=7.6), 4.49–4.58 (1H, m), 5.34 (1H, d, J=2.5), 6.98 (1H, s), 7.26–7.40 (10H, m).

EXAMPLE 72

Synthesis of 3-[(3'R,5'S)-7'-oxo-1'-aza-4'-oxabicyclo[3.2.0]hept-3'-yl]-2(S)-amino-3(R)-methoxypropionic acid (32a, R"=—CH$_3$)

To a solution of compound (30a), obtained in Example 67 (140 mg), in methanol (20 ml), 10% palladium on activated carbon (70 mg) was added and shaken in a hydrogen atmosphere at 52 psi for 30 minutes. Catalyst was removed by filtration and the filtrate was evaporated. The residue was partitioned between water and ethyl acetate. Water layer was lyophilized and the title compound was obtained as white powder.

Yield: 60 mg (79.0%)

$[\alpha]_D^{22}$=−75.8° (C 0.32, H$_2$O)

$^1$H-NMR(D$_2$O) δ: 2.92 (1H, d, J=16.7), 3.08 (1H, dd, J=6.0, 11.4), 3.36 (1H, dd, J=2.2, 16.8), 3.52 (3H, s), 3.78 (1H, dd, J=1.9, 4.6), 4.02 (1H, dd, J=7.1, 11.4), 4.25 (1H, d, J=4.6), 4.56–4.62 (1H, m), 5.45 (1H, d, J=2.5).

IR (Nujol) νmax (cm$^{-1}$): 3365, 1774, 1647

EXAMPLE 73

Synthesis of 3-[(3'R,5'S)-7'-oxo-1'-aza-4'-oxabicyclo[3.2.0]hept-3'-yl]-2(S)-amino-3(R)-benzyloxypropionic acid (32b, R"=—CH$_2$C$_6$H$_5$)

Starting from 0.90 g of compound (30b) and following the procedure as described in Example 72, the title compound was obtained.

Yield: 0.40 g (72.0%)

$[\alpha]_D^{29}$=−114° (C 0.08, CH$_3$OH)

IR (film) νmax (cm$^{-1}$): 3400, 3250, 1780, 1625

Mass m/z (FAB) : 307 [M+1]$^+$ $^1$H-NMR(D2O) δ: 7.50–7.40 (m, 5H), 5.46 (d, J=2.42 Hz, 1H), 4.85 (d, J=11.50 Hz, 1H), 4.63 (d, J=11.50 Hz, 1H), 4.63–4.60 (m, 1H), 4.27 (d, J=4.36 Hz, 1H), 4.02 (d, J=3.75 Hz, 1H), 3.91 (dd, J$_1$=7.22 Hz, J$_2$=11.41 Hz, 1H), 3.32 (dd, J$_1$=2.15 Hz, J$_2$=16.65 Hz, 1H), 2.93 (dd, J$_1$=5.60 Hz, J$_2$=11.50 Hz, 1H), 2.89 (d, J=16.70 Hz, 1H). CDλ$_{max}^{CH_3OH}$ (cotton effect): 226 nm(−).

EXAMPLE 74

Synthesis of 3-[(3'R,5'S)-7'-oxo-1'-aza-4'-oxabicyclo[3.2.0]hept-3'-yl]-2(S)-amino-3(R)-(4"-fluorobenzyl)oxy-propionic acid (32c,

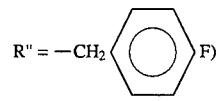

A mixture of compound (30c) (90 mg) and 10% Pd/C (90 mg) in ethyl acetate:methanol (1:1,5 ml) was hydrogenated at 50 psi hydrogen pressure for ½ hour. The mixture was filtered through celite. The celite was washed thoroughly with water. The combined water layer was freeze dried and the crude compound was purified on ODS column using water and acetonitrile as gradient eluant from 2% to 50% acetonitrile. The purity of the fraction was checked by HPLC. The pure fractions were, combined and freeze dried, gave the title compound.

Yield: 40 mg (70%)

$[\alpha]_D^{22}$=−120° (C 0.5, H$_2$O)

m.p. >200° (dec.)

$^1$H-NMR(D$_2$O) δ: 2.66–2.80 (2H, m), 3.09–3.22(1H, dd, J=2.40, 11.25), 3.68–3.88 (3H, m), 4.10 (1H, d, J=6.31), 4.36–4.48 (2H, m), 5.27 (1H, d, J=2.45), 6.95–7.06 (2H, m), 7.26–7.38 (2H, m).

EXAMPLE 75

Synthesis of 3-[(3'R,5'S)-7'-oxo-1'-aza-4'-oxabicyclo[3.2.0]hept-3'-yl]-2(S)-amino-3(R)-(4"-methoxybenzyl)oxypropionic acid (32d,

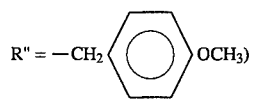

Starting from compound (30d) (260 mg) and 10% Pd/C (100 mg) in methanol/ethyl acetate (1:5, 20 ml), the title compound was obtained by following the procedure as described in Example 74.

Yield: 130 mg (78.8%)

$[\alpha]_D^{24}$=−80° (c 0.1, H$_2$O)

$^1$H-NMR(D$_2$O) δ: 2.81–2.91 (2H, m), 3.31 (1H, d, J=16.7), 3.85 (3H, s), 3.82–4.01 (2H, m), 4.26 (1H, d, J=4.4), 4.52–4.66 (3H, m), 5.43 (1H, d, J=2.0), 7.05 (2H, d, J=8.4), 7.43 (2H, d, J=8.8).

EXAMPLE 76

Synthesis of 3-[(3'R,5'S)-7'-oxo-1'-aza-4'-oxabicyclo[3.2.0]hept-3'-yl]-2(S)-amino-3(R)-cyclopropylmethyloxypropionic acid (32e,

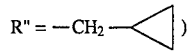
R" = —CH$_2$—⊲ )

Starting from compound (30e) (300 mg) and 10% Pd/C (100 mg) in methanol/ethyl acetate (1:5, 20 ml ), the title compound was obtained by following the procedure as described in Example 74.

Yield: 107 mg (61.3%)

$[\alpha]_D^{22}$=−90° (C 0.1, H$_2$O)

$^1$H-NMR(D$_2$O) δ: 0.29–0.33 (2H, m), 0.57–0.65 (2H, m), 1.10–1.14 (1H, m), 2.93 (1H, d, J=16.6), 3.16 (1H, dd, J=5.9, 11.0), 3.31–3.50 (2H, m), 3.63 (1H, dd, J=7.1, 10.9), 4.02–4.07 (2H, m), 4.28 (1H, d, J=4.7), 4.56–4.64 (1H, m), 5.5 (1H, d, J=2.5).

In the process B, Bh is a benzhydryl group, TBDMS is a t-butyldimethylsilyl group and Ts is a p-toluenesulfonyl group.

Synthesis of present compounds by process C

EXAMPLE 77

Synthesis of 3-O-benzyl-D-xylosic acid γ-lactone (18b)

A 40.9 g quantity of 3-O-benzyl-D-xylofuranose (17b) was dissolved in 240 ml of 1,4-dioxane and 100 ml of water. A 50 g quantity of calcium carbonate was added to the solution and 22 ml of bromine was added dropwise with stirring. The stirring was continued for 36 hours and sodium sulfite was added until the red color of the bromine was removed. After filtering off the salt precipitated, the filtrate was concentrated, and the residue was dissolved in ethyl acetate, washed with water and dried over sodium sulfate. The ethyl acetate solution was evaporated to dryness and the residue was recrystallized from cyclohexane, giving 21.7 g of white crystalline title compound (18b) (yield 53.4%).

Melting point: 102°–103° C.

$[\alpha]_D^{14}$=+35.1° (C 0.114 CH$_3$OH)

IR (KBr) vmax (cm$^{-1}$): 3480, 3380, 1770

Mass m/z (EI): 238 [M]$^+$, 91 [CH$_2$Ph]$^+$ $^1$H-NMR (C$_2$D$^2$Cl$_4$) δ: 7.40–7.33 (m, 5H), 4.83 (d, J=11.86 Hz, 1H), 4.73 (d, J=7.74 Hz, 1H), 4.68 (d, J=11.86 Hz, 1H), 4.58–4.55 (m, 1H), 4.42 (dd, J$_1$=7.92 Hz, J$_2$=7.92 Hz, 1H), 3.97–3.94(dd, J$_1$=2.64 Hz, J$_2$=12.87 Hz, 1H), 3.88–3.84 (dd, J$_1$=3.0 Hz, J$_2$=12.86 Hz, 1H), 2.2 (s, 2H)

EXAMPLE 78

Synthesis of diphenylmethyl 3-O-benzyl-D-xylosate (19b)

A 16 g quantity of the compound (18b) prepared in Example 77 was dissolved in 75 ml of 1,4-dioxane. A 320 ml quantity of 0.1N-potassium hydroxide was added dropwise to the solution with stirring at 50° C. The stirring was continued for two more hours. After distilling off the solvent, the syrupy residue was dissolved in acetone and 40 g of Dowex 50W (H$^+$) was added thereto with stirring. The Dowex 50W was filtered off five minutes later. Diphenyldiazomethane was added to the filtrate with stirring. After 4 hours of reaction, the reaction mixture was concentrated. The obtained oily residue was subjected to silica gel column chromatography and eluted gradiently with cyclohexane-ethyl acetate, giving 19.5 g of white crystalline title compound (19b) (yield 68.7%).

Melting point: 100.5°–101.5° C.

$[\alpha]_D^{14}$=+20.0° (C 0.052, EtOH)

IR (film) vmax (cm$^{-1}$): 3430, 3350, 1740

Mass m/z (EI): 422[M]$^+$, 239 [M-OCH$_2$Ph]$^+$, 167 [CHPh$_2$]$^+$, 91[CH$_2$Ph]$^+$ $^1$H-NMR (CD$_3$OD) δ: 7.38–7.08 (m, 15H), 6.93 (s, 1H), 4.56 (d, J=2.16 Hz, 1H), 4.52 (d, J=11.19 Hz, 1H), 4.27 (d, J=11.16 Hz, 1H), 4.00 (dd, J$_1$=2.14 Hz, J$_2$=5.81 Hz, 1H), 3.92–3.89 (q, 1H), 3.74–3.67 (m, 2H)

EXAMPLE 79

Synthesis of diphenylmethyl 3-O-benzyl-4,5-O-isopropylidene-D-xylosate (20b)

A 13 g quantity of the compound (19b) prepared in Example 78 was dissolved in 200 ml of anhydrous acetone. A 20 g quantity of anhydrous copper sulfate was added to the solution. The mixture was stirred at room temperature for 40 hours. After filtering off the precipitate, the filtrate was concentrated. The obtained oily residue was subjected to silica gel column chromatography and eluted with cyclohexane-ethyl acetate, giving 11 g of white crystalline title compound (20b) (yield 77.3%).

Melting point: 68°–69° C.

$[\alpha]_D^{14}$=+32.1° (C 0 118, CHCl$_3$)

IR (film) vmax (cm$^{-1}$): 3450, 1740, 1380, 1370

Mass m/z (EI): 461 [M-1]$^+$, 295[M-CHPh$_2$]$^+$, 18310CHPh$_2$]$^+$, 167[CHPh$_2$]$^+$, 91[CH$_2$Ph]$^+$ $^1$H-NMR (C$_2$D$_2$C$_{14}$) δ: 7.34–6.99 (m, 15H), 6.94 (s, 1H), 4.59 (d, J=11.30 Hz, 1H), 4.41–4.37 (q, 1H), 4.26 (s, 1H), 4.19 (d, J=11.29 Hz, 1H), 4.07 (dd, J$_1$=6.45 Hz, J$_2$=8.78 Hz, 1H), 3.88 (dd, J$_1$=7.20 Hz, J$_2$=8.24 Hz, 1H), 3.86 (dd, J$_1$=2.42 Hz, J$_2$=7.08 Hz, 1H), 3.1 (s, 1H), 1.44 (s, 3H), 1.36 (s, 3H)

EXAMPLE 80

Synthesis of diphenylmethyl 2-O-trifluoromethanesulfonyl-3-O-benzyl-4,5-O-isopropylidenepentanoate (34, R$_4$=SO$_2$CF$_3$)

A 4 g quantity of the compound (20b) prepared in Example 79 was dissolved in 100 ml of dichloromethane and 8 ml of pyridine was added to the solution. A 3 ml quantity of trifluoromethanesulfonic anhydride was added while being stirred with ice-cooling, followed by 4 hours of reaction. The reaction mixture thus obtained was used without isolation in Example 81 which followed.

IR (film) vmax (cm$^{-1}$): 3400, 1745, 1380, 1350

Mass m/z (EI): 579 [M-CH$_3$]$^+$, 427[M-CHPh$_2$]$^+$, 167 [CHPh2]$^+$, 91[CH$_2$Ph]$^+$

EXAMPLE 81

Synthesis of diphenylmethyl 2-deoxy-2-benzylamino-3-O-benzyl-4,5-O-diisopropylidene-D-erythropentanoate (35) and diphenylmethyl 2-deoxy-2-benzylamino-3-O-benzyl-4,5-O-isopropylidene-D-threopentanoate (36)

The reaction mixture prepared in Example 80 was added to a solution of 15 ml of benzylamine in 120 ml of dichloromethane. The mixture was reacted with stirring for 5 hours. The reaction mixture was washed with water, dried over sodium sulfate and concentrated. The resulting oily residue was subjected to silica gel column chromatography and eluted with cyclohexane-ethyl acetate (9:1), giving 2.79 g of white crystalline title compound (35) (yield 58.4%) and 1.34 g of white crystalline title compound (36) (yield 28.2%).

Compound (35)

Melting point: 89°–90° C.

$[\alpha]_D^{21}=-16.2°$ (C 0.136, CHCl$_3$)

IR (film) vmax (cm$^{-1}$): 3320, 1740, 1380, 1370

Mass m/z (CI): 552 [M+1]$^+$, 167[CHPh$_2$]$^+$, 91[CH$_2$Ph]$^+$ $^1$H-NMR (C$_2$D$_2$Cl$_4$) δ: 7.34–7.14 (m, 20H), 1H), 6.92 (s, 1H), 4.77 (d, J=11.50 Hz, 1H), 4.51 (d, J=11.50 Hz, 1H), 4.19 (q, 1H), 4.00 (dd, J$_1$=6.34 Hz, J$_2$=8.46 Hz, 1H), 3.67 (dd, J$_1$=8–24 Hz, J$_2$=8.10 Hz, 1H), 3.66 (d, J=13.54 Hz, 1H), 3.66 (dd, J$_1$=7.16 Hz, J$_2$=6.34 Hz, 1H), 3.53 (d, J=12.98, 1H), 3.41 (d, J=6.20 Hz, 1H), 2.15(s, 1H), 1.93 (s, 1H), 1.38 (s, 3H), 1.30 (s, 3H)

Compound (36)

Melting point: 84°–85° C.

$[\alpha]_D^{21}=+69.4°$ (C 0.132, CHCl$_3$)

IR (film) vmax (cm$^{-1}$): 3350, 1740, 1380, 1370

Mass m/z (CI): 552 [M+1]$^+$, 167[CHPh$_2$]$^+$, 91[CH$_2$Ph]$^+$ $^1$H-NMR (C$_2$D$_2$Cl$_4$) δ: 7.34–7.06 (m, 20H), 6.92 (s, 1H), 4.62 (d, J=11.43 Hz, 1H), 4.47 (q, 1H), 4.15 (d, J=11.44 Hz, 1H), 3.92 (d, J=12.77 Hz, 1H), 3.78 (dd, J$_1$=6.36 Hz, J$_2$=8.34 Hz, 1H), 3.77 (dd, J$_1$=8.14 Hz, J$_2$=1.98 Hz, 1H), 3.52 (dd, J$_1$=7.98 Hz, J$_2$=7.68 Hz, 1H), 3.49 (d, J=12.71 Hz, 1H), 3.22 (d, J=2.25 Hz, 1H), 2.16 (s, 1H), 1.37 (s, 3H), 1.33 (s, 3H)

EXAMPLE 82

Synthesis of diphenylmethyl 2-deoxy-2-(N-benzyloxycarbonyl-N-benzyl)amino-3-O-benzyl-4,5-O-isopropylidene-D-erythropentanoate (37)

A 5.29 g quantity of the compound (35) prepared in Example 81 was dissolved in 200 ml of diethyl ether. To the solution were added 10 g of sodium hydrogencarbonate and 100 ml of water. A 4.8 ml quantity of benzyl chloroformate was added dropwise with vigorous stirring at room temperature, followed by 20 hours of reaction. The organic layer was dried over sodium sulfate and concentrated. The obtained residue was subjected to silica gel column chromatography and eluted gradiently with cyclohexane-ethyl acetate, giving 5.22 g of white crystalline title compound (37) (yield 79.3%).

Melting point: 89°–91° C.

$[\alpha]_D^{27}=0°$ (C 0.070, CHCl$_3$)

IR (film) vmax (cm$^{-1}$): 1745, 1700, 1380, 1370

Mass m/z (CI): 686 [M+1]$^+$ Anal. Calcd. for C$_{43}$H$_{43}$O$_7$N: C, 75.30; H, 6.32; N, 2.04 Found: C, 75.31; H, 6.38; N, 1.92

EXAMPLE 83

Synthesis of diphenylmethyl 2-deoxy-2-(N-benzyloxycarbonyl-N-benzyl)amino-3-O-benzyl-D-erythropentanoate (38)

A 5.22 g quantity of the compound (37) prepared in Example 82 was dissolved in 50 ml of 1,4-dioxane. A 40 ml quantity of saturated oxalic acid was added to the solution, followed by stirring at 85° C. for 8 hours. The reaction mixture was adjusted to a pH of 7 with sodium hydrogencarbonate. After distilling off the solvent, the residue was extracted with ethyl acetate and dried over sodium sulfate. After distilling off the solvent under a reduced pressure, the residue thus obtained was subjected to silica gel column chromatography and eluted gradiently with cyclohexane-ethyl acetate, giving 4.5 g of white crystalline title compound (38) (yield 92.3%).

Melting point: 102°–104° C.

$[\alpha]_D^{27}=-22.6°$ (C 0.102, CHCl$_3$)

IR (KBr) vmax (cm$^{-1}$): 3400, 1740, 1660

Mass m/z (CI): 645 [M]$^+$ Anal. Calcd. for C$_{40}$H$_{39}$O$_7$N: C, 74.40; H, 6.09; N, 2.17 Found: C, 74.58; H, 6.39; N, 2.14

EXAMPLE 84

Synthesis of diphenylmethyl 2-deoxy-2-(N-benzyloxycarbonyl-N-benzyl)amino-3-O-benzyl-5-O-tosyl-D-erythropentanoate (39,

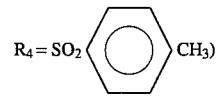
)

A 5.55 g quantity of the compound (38) prepared in Example 83 was dissolved in 30 ml of dichloromethane. A 10 ml quantity of pyridine was added to the solution and 3.78 g of p-toluenesulfonyl chloride was added while being stirred with ice-cooling. After 30 minutes, the reaction mixture was left to stand in a refrigerator for 10 hours. The reaction mixture was successively washed with cold 0.5N-hydrochloric acid, a saturated aqueous solution of sodium hydrogencarbonate and water in this order and dried over sodium sulfate. After distilling off the solvent under a reduced pressure, the residue was subjected to silica gel column chromatography and eluted gradiently with cyclohexane-ethyl acetate, giving 5.27 g of a pale yellow oily title compound (yield 76.6%).

$[\alpha]_D^{14}=-25.0°$ (C 0.092, CHCl$_3$)

IR (film) vmax (cm$^{-1}$): 3430, 1740, 1700

Mass m/z (FAB): 800 [M+1]$^+$

EXAMPLE 85

Synthesis of diphenylmethyl 2-deoxy-2-(N-benzyloxycarbonyl-N-benzyl)amino-3-O-benzyl-4-O-(3'-oxo-2'-azacyclobutyl)-5-O-tosyl-D-erythropentanoate (40,

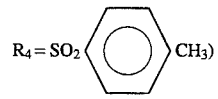
)

A 5.08 g quantity of the compound (39,

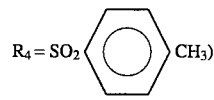
)

prepared in Example 84 was dissolved in 70 ml of anhydrous benzene. To the solution were added 0.34 g of palladium acetate, 1.5 ml of triethylamine and 1.24 g of 4-acetoxyazetidin-2-one. The mixture was stirred in a current of nitrogen gas at room temperature for 20 hours. After filtering off the precipitate, the filtrate was washed with water and dried over sodium sulfate. After distilling off the solvent under a reduced pressure, the oily residue was subjected to silica gel column chromatography and eluted gradiently with cyclohexane-ethyl acetate, giving 3.26 g of a white solid title compound (yield 60.0%).

Melting point: 69°–70.3° C.
IR (film) νmax (cm$^{-1}$): 3360, 1770, 1740, 1690
Mass m/z (FAB): 869 [M+1]$^+$

EXAMPLE 86

Synthesis of diphenylmethyl 2-deoxy-2-(N-benzyloxycarbonyl-N-benzyl)amino-3-O-benzyl-4-O-(3,-oxo-2,-azacyclobutyl)-5-deoxy-5-bromo-D-erythropentanoate (41, R$_6$=Br)

A 3.26 g quantity of the compound (40,

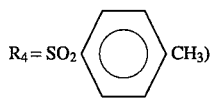

$R_4 = SO_2\langle\bigcirc\rangle CH_3$)

prepared in Example 85 was dissolved in 120 ml of tetrahydrofuran. A 2.0 g quantity of lithium bromide was added to the solution. The mixture was refluxed for 12 hours. After distilling off the solvent under a reduced pressure, the residue was dissolved in ethyl acetate, washed with water and dried over sodium sulfate. After distilling off the solvent under a reduced pressure, the residue was subjected to silica gel column chromatography and eluted gradiently with cyclohexane-ethyl acetate, giving 2.11 g of a white solid title compound (yield 72.5%).

Melting point: 50°–51° C.
IR (film) νmax (cm$^{-1}$): 3280, 1780, 1740, 1700
Mass m/z (FAB): 777 [M+1]$^+$
CD λmax (cotton effect): 214 nm (–)

EXAMPLE 87

Synthesis of diphenylmethyl 3-[(3'R,5'S)-7'-oxo-1'-aza-4'-oxabicyclo[3.2.0]hept-3'-yl]-2(S)-(N-benzyloxycarbonyl-N-benzyl)amino-3(R)-benzyloxypropionate (42) and diphenylmethyl 3-[(3'R,5'R)-7'-oxo-1'-aza-4'-oxabicyclo[3.2.0]hept-3'-yl]-2(S)-(N-benzyloxycarbonyl-N-benzyl)amino-3(R)-benzyloxypropionate (43)

(method a)

A 62.9 mg quantity of the compound (24, R$_6$=Br) prepared in Example 86, 33 mg of cesium carbonate and 1 ml of dimethyl sulfoxide were stirred at room temperature for 1.5 hours. The reaction mixture was extracted with ethyl acetate, washed with water and dried over sodium sulfate. After distilling off the solvent under a reduced pressure, the residue was subjected to preparative silica gel thin layer chromatography and developed with cyclohexane-ethyl acetate (8:2), followed by scraping for separation, giving 27.7 mg of white solid title compound (42) (yield 49.1%) and 10 mg of solid title compound (43) (yield 17.7%).

(method b)

A 330 mg quantity of the compound (41, R$_6$=Br) prepared in Example 86, 610 mg of silver 2,2-dimethyl-6,6,7,7,8,8,8-heptafluoro-3,5-octanedionate and 5 ml of N,N-dimethylformamide were stirred in a current of nitrogen gas at 70° C. for 4 hours. The subsequent procedure was carried out in the same manner (as in method a), giving 84 mg of white solid title compound (42) (yield 28.3%) and 15 mg of solid title compound (43) (yield 5.1%).

Compound (42)
Melting point: 121°–122° C.
$[\alpha]_D^{25}$=–70.76° (C 1.12 CHCl$_3$)
IR (film) νmax (cm$^{-1}$): 1800, 1740, 1700
Mass m/z (EI): 697 [M+1]$^+$, 529[M-CHPh$_2$]$^+$, 167 [Ph2CH]$^+$, 91[PhCH$_2$]$^+$
CD $\lambda_{max}^{CHOH}$ (cotton effect): 227 nm (–)

Compound (43)
Melting point: 66°–67° C.
$[\alpha]_D^{25}$=–1.81° (C 0.72, CHCl$_3$)
IR (film) νmax (cm$^{-1}$): 1820, 1740, 1700
Mass m/z (EI): 696 [M]$^+$, 529[M-CHPh$_2$]$^+$, 167[CHPh$_2$]$^+$, 91[CH$_2$Ph]$^+$
m/z (CI): 697 [M+1]$^+$
CD $\lambda_{max}^{CH_3CH}$ (cotton effect): 224 nm (+)

EXAMPLE 88

Synthesis of 3-[(3'R,5'S)-7'-oxo-1'-aza-4'-oxabicyclo[3.2.0]hept-3'-yl]-2(S)-amino-3(R)-benzyloxypropionic acid (32b)

A 0.74 g quantity of 5% palladium-carbon was added to a solution of 0.57 g of the compound (42) prepared in Example 87 in 60 ml of methanol. The mixture was shaken in a hydrogen stream at 52 psi for 11 hours. The precipitate was filtered off and the filtrate was concentrated at up to 40° C. under a reduced pressure. The residue was washed with anhydrous ether, giving 0.209 g of pale yellow powder. The obtained powder was further subjected to ODS medium-pressure column chromatography, and eluted with 40% MeOH for purification, followed by lyophilization, giving 50 mg of white powder title compound (32b) (yield 20.0%).

$[\alpha]_D^{29}$=–114° (C 0.08, CH$_3$OH)
IR (film) νmax (cm$^{-1}$): 3400, 3250, 1780, 1625
Mass m/z (FAB): 307 [M+1],
$^1$H-NMR (D$_2$O) δ: 7.50–7.40 (m, 5H), 5.46 (d, J=2.42 Hz, 1H), 4.85 (d, J=11.50 Hz, 1H), 4.63 (d, J=11.50 Hz, 1H), 4.63–4.60 (m, 1H), 4.27 (d, J=4.36 Hz, 1H), 4.02 (d, J=3.75 Hz, 1H), 3.91 (dd, J$_1$=7.22 Hz, J$_2$=11.41 Hz, 1H), 3.32 (dd, J$_1$=2.15 Hz, J$_2$=16.65 Hz, 1H), 2.93 (dd, J$_1$=5.60 Hz, J$_2$=11.50 Hz, 1H), 2.89 (d, J=16.70 Hz, 1H)
CD $\lambda_{max}^{CH_3OH}$ (cotton effect): 226 nm (–)

EXAMPLE 89

Synthesis of 3-[(3'R,5'R)-7'-oxo-1'-aza-4'-oxabicyclo[3.2.0]hept-3'-yl]-2(S)-amino-3(R)-benzyloxypropionic acid (44)

Using 0.57 g of the compound (43) prepared in Example 87, the procedure of Example 88 was repeated, giving 56 mg of white powder title compound (44) (yield 21.0%).

$[\alpha]_D^{29}$=–42.86° (C 0.06, H$_2$O)
IR (KBr) νmax (cm$^{-1}$): 3250, 1780, 1625
Mass m/z (FAB): 307 [M+1]
$^1$H-NMR (D$_2$O) δ: 7.52–7.43 (m, 5H), 5.36 (d, J=2.36 Hz, 1H), 4.79 (d, J=11.64 Hz, 1H), 4.64 (d, J=11.58 Hz, 1H), 4.80–4.60 (m, 1H), 4.24 (d, J=4.69 Hz, 1H), 4.02 (dd, J$_1$=1.15 Hz, J$_2$=4.61 Hz, 1H), 3.63 (dd, J$_1$=4.35 Hz, J$_2$=11.52 Hz, 1H), 3.29 (dd, J$_1$=1.86 Hz, J$_2$=16.45 Hz, 1H), 3.16 (dd, $J_1=7.73$ Hz, $J_2=11.22$ Hz, 1H), 2.96 (d, $J=16.44$ Hz, 1H)

CD $\lambda_{max}^{CH_3OH}$ (cotton effect): 224 nm (+)

Formulation Example 1

(Tablets)

The compound (32b), lactose and corn starch were mixed together in the following proportions, and water was added to knead the mixture. The mixture was granulated using a suitable granulator and dried at 40° C. After adjusting the granules in shape, potassium stearate was added. The coated granules were formulated with a punch into tablets.

| | |
|---|---|
| Compound (32b) | 50 mg |
| Lactose | 210 mg |
| Corn starch | 80 mg |
| Potassium stearate | 10 mg |
| Per tablet | 350 mg |

Formulation Example 2

(Capsules)

The compound (44), lactose, crystalline cellulose and corn starch were mixed together in the following proportions. After adding talc, the mixture was stirred. Using a suitable encapsulating machine, the mixture was encapsulated into hard-gelatin capsules.

| | |
|---|---|
| Compound (44) | 50 mg |
| Lactose | 100 mg |
| Crystalline cellulose | 40 mg |
| Corn starch | 55 mg |
| Talc | 5 mg |
| Per capsule | 250 mg |

Formulation Example 3

(Injection)

A 400 g quantity of glucose was added to 50 g of compound (32b). The mixture was dissolved in distilled water to make 10 l of a solution. The solution was subjected to filtration for sterilization, and charged in an amount of 10 ml per ampoule into ampoules using a suitable ampoule filling machine. After replacement by nitrogen gas, the ampoules were thermally sealed by fusion.

Formulation Example 4

(Suppository)

Witepsol W-35 (a registered trademark, a product of Dynamite Nobel Co., Ltd.) was fused at about 60° C. and maintained at about 45° C. After adding the compound (44) in the following amount, the mixture was molded into a suppository preparation (1 g each) using a suitable suppository-molding device.

| | |
|---|---|
| Compound (44) | 200 mg |
| Witepsol W-35 | 800 mg |
| Per a molding | 1000 mg |

Pharmacological Test 1 (In Vitro KB Cell Cytotoxicity Assay)

The cytotoxicity against KB cells was determined in accordance with a protein staining method (Grillis et al., Anal. Biochem., 159, 109 (1986)) using crystal violet.

Stated more specifically, KB cells were incubated in an Eagle's minimum medium containing 10% FCS in a $CO_2$ incubator at 37° C. The number of the cells was counted with a hemocytometer. A 100 µl quantity of the cell suspension, $3\times10^4$ cells/ml, was placed into each well of a 96-well plate and incubated for 24 hours. Portions (100 µl) of the drug diluted to final concentrations of 10, 1, 0.1, 0.01 and 0.001 µg/ml were added, as one dosage, to three wells, respectively. A drug-free medium was added to the wells of the control group. After incubation for 3 days, 25 µl of 25% glutaraldehyde was added and fixed for 15 minutes, followed by washing with water and drying. A 100 µl quantity of 0.05% crystal violet was added for 15 minutes of staining, followed by washing with water and drying. Extraction was performed with 100 µl of 0.05M $NaH_2PO_4$/EtOH (1:1 volume ratio). The absorbance was measured at a wavelength of 540 nm with a multi-scan spectrophotometer. The percent cell growth inhibition was calculated based on the absorbance by the following equation Percent inhibition =

$$\frac{\text{Absorbance of control group-Absorbance of test group}}{\text{Absorbance of control group}} \times 100$$

The $IC_{50}$ value (concentration of the drug for inhibiting the cell growth by 50%) was calculated through log-logit transformation of the dose-response curve and linear regression. Table 1 shows the results.

TABLE 1

| Test compound No. | $IC_{50}$ (µg/ml) |
|---|---|
| 4 | 0.07 |
| 5 | 0.3 |
| 6 | 0.09 |
| 7 | 0.09 |
| 12a | 3 |
| 12b | 0.3 |
| 32a | 0.03 |
| 32b | 0.06 |
| 32c | 0.04 |
| 32d | 0.09 |
| 32e | 0.4 |
| 42 | 3 |
| 43 | 3 |

Pharmacological Test 2 (In Vivo Antitumor Activity against Sarcoma 180)

$5\times10^6$ cells of transplantable mouse tumor, Sarcoma 180, were subcutaneously transplanted in the dorsal portion of 6-week-old male ICR mice (6–7 mice in each group). The test drug was dissolved in physiological saline containing 0.25 % Tween 80 and 3.5% dimethyl sulfoxide. The solution was intraperitoneally administered to the mice every four days, starting the administration 24 hours after the transplantation, three times in total. On the 12th day after the transplantation, the tumors were removed from the bodies and weighed. The average weight of the tumors in the test group and the corresponding weight in the control group were calculated to determine the ratio of tumor growth inhibition. Table 2 shows the results.

TABLE 2

| Test compound No. | Dosage (mg/kg/day) | Mortality in 12 days | Cell growth inhibition rate (%) |
|---|---|---|---|
| 12b | 20 | 0/7 | 31 |
| | 10 | 0/7 | 19 |

TABLE 2-continued

| Test compound No. | Dosage (mg/kg/day) | Mortality in 12 days | Cell growth inhibition rate (%) |
|---|---|---|---|
| 32b | 5 | 0/7 | 19 |
| | 1.0 | 0/6 | 38 |
| | 0.1 | 0/6 | 12 |

We claim:

1. A derivative of 3-(7'-oxo-1'-aza-4'-oxabicyclo[3.2.0]hept-3'-yl)propionic acid represented by the formula

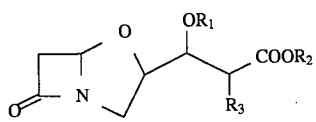

wherein $R_1$ is hydrogen or selected from the group consisting of a hydrogen atom, a lower alkyl group of one to six carbon atoms which is unsubstituted or has at least one cycloalkyl group substituent, an acyl group represented by RCO, wherein R is a straight- or branched-chain alkyl of 1–5 carbon atoms, a benzoyl group which is unsubstituted or has at least one substituent selected from the group consisting of a straight- or branched-chain lower alkyl group of one to six carbon atoms which is unsubstituted or has one to three halogen atom substituents, a straight- or branched-chain lower alkoxy group of one to six carbon atoms, a halogen atom, a nitro group, a cyano group and a lower alkoxycarbonyl group which is unsubstituted or has as a substituent at least one straight- or branched-chain lower alkoxy group of one to six carbon atoms and a benzyl group which is unsubstituted or has at least one substituent selected from the group consisting of a straight- or branched-chain lower alkyl group of one to six carbon atoms which is unsubstituted or has one to three halogen atom substituents, a straight- or branched-chain lower alkoxy group of one to six carbon atoms, a halogen atom, a nitro group, a cyano group and a lower alkoxycarbonyl group which is unsubstituted or has as a substituent at least one straight- or branched-chain lower alkoxy group of one to six carbon atoms, $R_2$ is selected from the group consisting of a hydrogen atom and a carboxyl-protecting group, and $R_3$ is selected from the group consisting of a hydroxyl group, an azido group, a benzenesulfonyloxy group which is unsubstituted or has at least one substituent selected from the group consisting of a straight- or branched-chain lower alkyl group of one to six carbon atoms which is unsubstituted or has one to three halogen atom substituents, a straight- or branched-chain lower alkoxy group of one to six carbon atoms, a halogen atom, a nitro group, a cyano group and a lower alkoxycarbonyl group which is unsubstituted or has as a substituent at least one straight- or branched-chain lower alkoxy group of one to six carbon atoms, a lower alkylsulfonyloxy group which is unsubstituted or has at least one substituent selected from the group consisting of a straight- or branched-chain lower alkoxy group of one to six carbon atoms, a halogen atom, a nitro group, a cyano group, a phenyl group and a lower alkoxycarbonyl group which is unsubstituted or has as a substituent at least one lower alkoxy group of one to six carbon atoms, a silyloxy group having three substituents, each substituent independently selected from the group consisting of a straight- or branched-chain lower alkyl group of one to six carbon atoms and a phenyl group and an amino group which is unsubstituted or has at least one substituent selected from the group consisting of 4-methoxybenzyl, 4-chlorobenzyl, benzyl and benzyloxycarbonyl, provided that where $R_1$ and $R_2$ are hydrogen atoms, $R_3$ is other than an amino group, and a pharmacologically acceptable salt thereof.

2. A method of treating a tumor in a patient in need of such treatment, the method comprising administering to the patient an antitumor-effective amount of the compound of claim 1.

3. A method according to claim 2, wherein the compound of claim 1 is administered at a daily dose of about 1 to about 5000 mg.

4. A method according to claim 2, wherein the compound of claim 1 is administered at a daily dose of about 10 to about 2000 mg.

5. A method according to claim 2, wherein the daily dose is divided into 2–4 individual doses.

6. A compound according to claim 1, wherein the pharmacologically acceptable salt is selected from the group consisting of sodium, potassium, magnesium, calcium, ammonia, methylamine, triethylamine, piperidine and pyridine.

7. The antitumor pharmaceutical composition according to claim 9, wherein the compound of claim 1 is present in a proportion of about 1 to about 70% by weight of the weight of said antitumor pharmaceutical composition.

8. A compound according to claim 1, wherein the optically active carbon [atom is] atoms on the oxazolidine ring are in the form of [3'R,5'S].

9. An antitumor pharmaceutical composition suitable for treating a tumor, comprising an antitumor-effective amount of the compound of claim 1 and a pharmaceutically acceptable carrier.

10. A compound according to claim 1, wherein $R_1$ is selected from the group consisting of an acetyl group, a benzoyl group, a methyl group, a cyclopropylmethyl group, a benzyl group, a 4-fluorobenzyl group and
a 4-methoxybenzyl group, $R_2$ is a hydrogen atom, and $R_3$ is an amino group.

11. A compound according to claim 1, wherein the compound is selected from the group consisting of
3-[(3'R,5'S)-7'-oxo-1'-aza-4'-oxabicyclo[3.2.0]hept-3'-yl]-2(R)-amino-3(R)-acetoxypropionic acid,
3-[(3'R,5'S)-7'-oxo-1'-aza-4'-oxabicyclo[3.2.0]hept-3'-yl]-2(R)-amino-3(R)-benzoyloxypropionic acid,
3-[(3'R,5'S)-7'-oxo-1'-aza-4'-oxabicyclo[3.2.0]hept-3'-yl]-2(S)-amino-3(R)-methoxypropionic acid,
3-[(3'R,5'S)-7'-oxo-1'-aza-4'-oxabicyclo[3.2.0]hept-3'-yl]-2(S)-amino-3(R)-(cyclopropylmethyloxy)propionic acid,
3-[(3'R,5'S)-7'-oxo-1'-aza-4'-oxabicyclo[3.2.0]hept-3'-yl]-2(S)-amino-3(R)-benzyloxypropionic acid,
3-[3'R,5'R)-7'-oxo-1'-aza-4'-oxabicyclo[3.2.0]hept-3'-yl]-2(S)-amino-3(R)-benzyloxypropionic acid,
3-[(3'R,5'S)-7'-oxo-1'-aza-4'-oxabicyclo[3.2.0]hept-3'-yl]-2(S)-amino-3(R)-(4-fluorobenzyloxy)propionic acid and
3-[(3'R,5'S)-7'-oxo-1'-aza-4'-oxabicyclo[3.2.0]hept-3'-yl]-2(S)-amino-3(R)-(4-methoxybenzyloxy)propionic acid.

12. A compound according to claim 1, wherein $R_1$ is selected from the group consisting of
a hydrogen atom,
a lower alkyl group of one to six carbon atoms which is unsubstituted or has at least one cycloalkyl group,
an acyl group represented by RCO, wherein R is hydrogen or a straight- or branched-chain alkyl of 1–5 carbon atoms,
a benzoyl group, and
a benzyl group which is unsubstituted or has at least one substituent selected from the group consisting of a halogen atom and a straight- or branched-chain lower alkoxy group of one to six carbon atoms, $R_2$ is selected from the group consisting of
a hydrogen atom,
a benzyl group and
a benzhydryl group, and $R_3$ is selected from the group consisting of
a hydroxyl group and
an amino group which is unsubstituted or has at least one substituent selected from the group consisting of a benzyl group and a benzyloxycarbonyl group.

* * * * *